US010696981B2

(12) United States Patent
Schultheiss

(10) Patent No.: US 10,696,981 B2
(45) Date of Patent: *Jun. 30, 2020

(54) PHACOSPORACEA RESISTANT SOYBEAN PLANTS

(71) Applicant: BASF PLANT SCIENCE COMPANY GMBH, Ludwigshafen (DE)

(72) Inventor: Holger Schultheiss, Boehl-Iggelheim (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 135 days.

This patent is subject to a terminal disclaimer.

(21) Appl. No.: 15/691,031

(22) Filed: Aug. 30, 2017

(65) Prior Publication Data

US 2018/0044696 A1 Feb. 15, 2018

Related U.S. Application Data

(63) Continuation of application No. 14/128,142, filed as application No. PCT/IB2012/053193 on Jun. 25, 2012, now Pat. No. 9,765,356.

(60) Provisional application No. 61/501,274, filed on Jun. 27, 2011.

(30) Foreign Application Priority Data

Jun. 27, 2011 (EP) ..................................... 11171484

(51) Int. Cl.
*C12N 15/82* (2006.01)
*C07K 14/415* (2006.01)
(52) U.S. Cl.
CPC ........ *C12N 15/8282* (2013.01); *C07K 14/415* (2013.01)
(58) Field of Classification Search
None
See application file for complete search history.

(56) References Cited

U.S. PATENT DOCUMENTS 6,653,533 B1 * 11/2003 Martin ................. C07K 14/415
435/419
9,765,356 B2 * 9/2017 Schultheiss ........ C12N 15/8282

FOREIGN PATENT DOCUMENTS

| CN | 101033252 A | 9/2007 |
| CN | 101665532 A | 3/2010 |
| WO | WO-1997/047183 A1 | 12/1997 |

OTHER PUBLICATIONS

Gu et al (Tomato Transcription Factors Pti4, Pti5, and Pti6 Activate Defense Responses When Expressed in *Arabidopsis*. The Plant Cell, vol. 14, 817-831, Apr. 2002) (Year: 2002).*
Zhou et al (The Pto kinase conferring resistance to tomato bacterial speck disease interacts with proteins that bind a cis-element of pathogenesis-related genes. The EMBO Journal vol. 16, 3207-3218, 1997) (Year: 1997).*
Grossi-de-Sa et al (Genetically Modified Soybean for Insect-Pests and Disease Control. Intech. 429-453, Apr. 2011). (Year: 2011).*
Berrocal-Lobo and Molina, Ethylene Response Factor 1 Mediates *Arabidopsis* Resistance to the Soilborne Fungus *Fusarium oxysporum*, MPMI, vol. 17, No. 7, (2004), pp. 763-770.
Berrocal-Lobo et al., Constitutive Expression of Ethylene-Response-Factor1 in *Arabidopsis* Confers Resistance to Several Necrotrophic Fungi, The Plant Journal, vol. 29, No. 1, (2002), pp. 23-32.
Dong et al., Studies on Methods in Cloning and Expression Quantification of Genes that Regulate Plant Disease Resistance Signal Transduction, Journal of Nanjing Agricultural University, vol. 26, No. 4, (2003), pp. 30-35.
Fourgoux-Nichol et al., Isolation of rapeseed genes expressed early and specifically during development of the male gametophyte, Plant Mol. Biol., 40(5):857-72 (1999).
Frederick et al., Polymerase Chain Reaction Assays for the Detection and Discrimination of the Soybean Rust Pathogens *Phakopsora pachyrhizi* and *P. meibomiao*, Phytopathology, vol. 92, No. 2, (2002), pp. 217-227.
Gu et al., Tomato transcription factors pti4, pti5, and pti6 activate defense responses when expressed in *Arabidopsis*, Plant Cell, 14(4):817-31 (2002).
Guo et al., Protein tolerance to random amino acid change, Proc. Natl. Acad. Sci. USA, 101(25):9205-10 (2004).
He et al., Overexpression of Pti5 in tomato potentiates pathogen-induced defense gene expression and enhances disease resistance to *Pseudomonas syringae* pv. tomato, Mol. Plant Microbe Interact., 14(12):1453-7 (2001).
Hill et al., Functional analysis of conserved histidines in ADP-glucose pyrophosphorylase from *Escherichia coli*, Biochem. Biophys. Res. Commun., 244(2):573-7 (1998).
International Preliminary Report on Patentability, issued in PCT/IB2012/053193, dated Jan. 16, 2014.
International Search Report, issued in PCT/IB2012/053193, dated Nov. 15, 2012.

(Continued)

*Primary Examiner* — Medina A Ibrahim
*Assistant Examiner* — Wayne Zhong
(74) *Attorney, Agent, or Firm* — Marshall, Gerstein & Borun LLP

(57) ABSTRACT

The present invention relates to a method of increasing resistance against fungal pathogens of the family Phacosporaceae in transgenic plants and/or plant cells. In these plants, the ethylene signaling pathway and/or activity of the ethylene signaling compounds is changed. This is achieved by priming the ethylene signaling pathway in these plants in comparison to wild type plants and/or wild type plant cells. Depending on the activating or inhibitory function of a particular signaling compound overexpression or knock-down of the cognate gene might be used.

15 Claims, 10 Drawing Sheets

Figure 1:
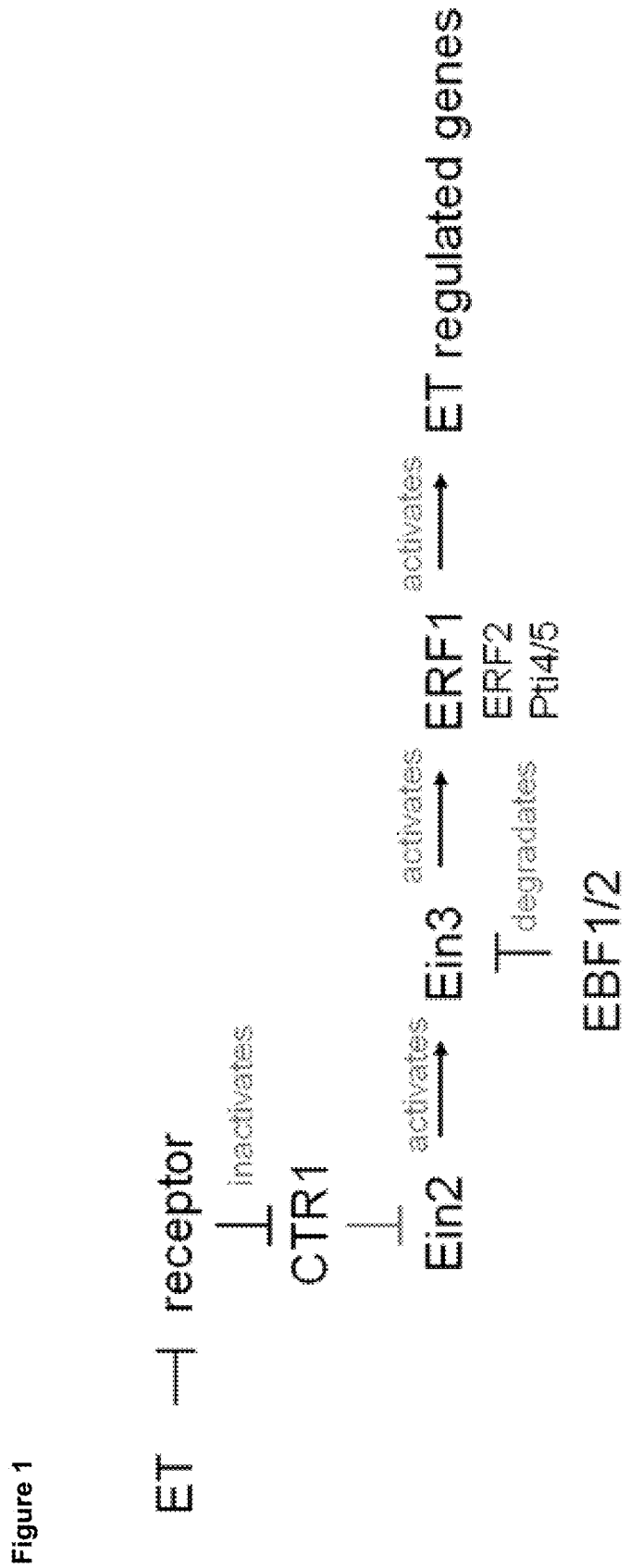

Specification includes a Sequence Listing.

(56) References Cited

OTHER PUBLICATIONS

Li et al., Production of transgenic soybean plants with two antifungal protein genes via Agrobacterium and particle bombardment, Biologia Plantarum, 48(3):367-74 (2004).

Panthee et al., Gene expression analysis in soybean in response to the causal agent of Asian soybean rust (*Phakopsora pachyrhizi* Sydow) in an early growth stage, Funct. Integr. Genomics, 7(4):291-301 (2007).

Rytter, Additional Alternative Hosts of *Phakopsora pachyrhizi*, Causal Agent of Soybean Rust, Plant Disease, vol. 68, No. 9, (1984), pp. 818-819.

\* cited by examiner

Figure 3

>SEQ1-AtERF1
ATGGATCCATTTTTAATTCAGTCCCCATTCTCCGGCTTCTCACCGGAATATTCTATCGGATC
TTCTCCAGATTCTTTCTCATCCTCTTCTTCTAACAATTACTCTCTTCCCTTCAACGAGAACGA
CTCAGAGGAAATGTTTCTCTACGGTCTAATCGAGCAGTCCACGCAACAAACCTATATTGAC
TCGGATAGTCAAGACCTTCCGATCAAATCCGTAAGCTCAAGAAAGTCAGAGAAGTCTTACA
GAGGCGTAAGACGACGGCCATGGGGGAAATTCGCGGCGGAGATAAGAGATTCGACTAGA
AACGGTATTAGGGTTTGGCTCGGGACGTTCGAAAGCGCGGAAGAGGCGGCTTTAGCCTAC
GATCAAGCTGCTTTCTCGATGAGAGGGTCCTCGGCGATTCTCAATTTTTCGGCGGAGAGA
GTTCAAGAGTCGCTTTCGGAGATTAAATATACCTACGAGGATGGTTGTTCTCCGGTTGTGG
CGTTGAAGAGGAAACACTCGATGAGACGGAGAATGACCAATAAGAAGACGAAAGATAGTG
ACTTTGATCACCGCTCCGTGAAGTTAGATAATGTAGTTGTCTTTGAGGATTTGGGAGAACA
GTACCTTGAGGAGCTTTTGGGGTCTTCTGAAAATAGTGGGACTTGGTGA

Figure 4

>SEQ2-AtERF1PRT
MDPFLIQSPFSGFSPEYSIGSSPDSFSSSSSNNYSLPFNENDSEEMFLYGLIEQSTQQT
YIDSDSQDLPIKSVSSRKSEKSYRGVRRRPWGKFAAEIRDSTRNGIRVWLGTFESAEE
AALAYDQAAFSMRGSSAILNFSAERVQESLSEIKYTYEDGCSPVVALKRKHSMRRRMT
NKKTKDSDFDHRSVKLDNVVVFEDLGEQYLEELLGSSENSGTW*

Figure 6

>SEQ3-SlPti4
ATGGATCAACAACTTCCACCAACTAACTTCCCAGTTGACTTCCCAGTTTACAGAAGAAACTC
CAGCTTCTCTAGGCTTATTCCATGCCTTACTGAGAAGTGGGGAGATCTTCCACTTAAGGTG
GACGATTCTGAGGATATGGTGATCTACGGACTTCTTAAGGATGCTCTTTCTGTTGGATGGT
CCCCATTCAACTTCACTGCTGGTGAAGTTAAGTCTGAGCCAAGGGAAGAGATTGAATCTTC
TCCAGAGTTCTCTCCATCTCCAGCTGAAACTACTGCTGCTCCAGCTGCTGAAACTCCAAAG
GGAAGGCATTATAGGGGAGTTAGACAAAGACCTTGGGGAAAGTTCGCTGCTGAAATTAGA
GATCCAGCTAAGAACGGTGCTAGAGTTTGGCTTGGAACTTATGAGACTGCTGAAGAGGCT
GCTATTGCTTATGATAAGGCCGCTTACAGAATGAGAGGATCCAAGGCTCATCTTAACTTCC
CACACAGGATTGGACTTAACGAACCAGAGCCAGTTAGAGTTACTGCTAAGAGAAGGGCTT
CTCCAGAACCAGCTTCTTCTTCTGGAAACGGATCCATGAAGAGAAGAAGAAAGGCTGTTCA
AAAGTGCGACGGTGAAATGGCTTCTAGATCTTCCGTTATGCAAGTGGGATGCCAAATTGAG
CAACTTACCGGTGTTCATCAGCTTCTCGTGATCTAA

Figure 7

>SEQ4-SlPti4PRT
MDQQLPPTNFPVDFPVYRRNSSFSRLIPCLTEKWGDLPLKVDDSEDMVIYGLLKDALSVGWSP
FNFTAGEVKSEPREEIESSPEFSPSPAETTAAPAAETPKGRHYRGVRQRPWGKFAAEIRDPAK
NGARVWLGTYETAEEAAIAYDKAAYRMRGSKAHLNFPHRIGLNEPEPVRVTAKRRASPEPASS
SGNGSMKRRRKAVQKCDGEMASRSSVMQVGCQIEQLTGVHQLLVI*

Figure 9

>SEQ5-SlPti5
ATGGTTCCAACTCCACAGTCTGATCTTCCACTCAACGAGAACGATTCTCAAGAGATGGTTC
TTTACGAGGTTTTGAACGAGGCTAACGCTCTTAACATTCCATACCTCCCACAAAGAAACCA
GCTTCTCCCTAGGAACAACATTCTTAGGCCACTTCAGTGCATTGGAAAGAAGTACAGGGGA
GTTAGAAGAAGGCCTTGGGGAAAGTATGCTGCTGAGATTAGAGATTCTGCTAGACATGGT
GCTAGAGTTTGGCTTGGAACTTTCGAAACTGCTGAAGAAGCTGCTCTTGCTTACGATAGAG
CTGCTTTCAGAATGAGAGGTGCTAAGGCTCTTTTGAACTTCCCATCCGAGATTGTGAACGC
TTCTGTGTCTGTGGATAAGCTTTCTCTTTGCTCCAACTCTTACACCACCAACAACAACTCTG
ATTCTAGCCTTAACGAGGTTTCCTCTGGAACTAACGATGTTTTCGAGTCCAGGTGCTAA

Figure 10

>SEQ6-SlPti5PRT
MVPTPQSDLPLNENDSQEMVLYEVLNEANALNIPYLPQRNQLLPRNNILRPLQCIGKKYRGVRR
RPWGKYAAEIRDSARHGARVWLGTFETAEEAALAYDRAAFRMRGAKALLNFPSEIVNASVSVD
KLSLCSNSYTTNNNSDSSLNEVSSGTNDVFESRC*

Figure 12

>SEQ7-AtERF2
ATGTACGGACAGTGCAATATAGAATCCGACTACGCTTTGTTGGAGTCGATAACACGTCACT
TGCTAGGAGGAGGAGGAGAGAACGAGCTGCGACTCAATGAGTCAACACCGAGTTCGTGTT
TCACAGAGAGTTGGGGAGGTTTGCCATTGAAAGAGAATGATTCAGAGGACATGTTGGTGTA
CGGACTCCTCAAAGATGCCTTCCATTTTGACACGTCATCATCGGACTTGAGCTGTCTTTTG
ATTTTCCGGCGGTTAAAGTCGAGCCAACTGAGAACTTTACGGCGATGGAGGAGAAACCAA
AGAAAGCGATACCGGTTACGGAGACGGCAGTGAAGGCGAAGCATTACAGAGGAGTGAGG
CAGAGACCGTGGGGAAATTCGCGGCGGAGATACGTGATCCGGCGAAGAATGGAGCTAG
GGTTTGGTTAGGGACGTTTGAGACGGCGGAAGATGCGGCTTTAGCTTACGATATAGCTGC
TTTTAGGATGCGTGGTTCCCGCGCTTTATTGAATTTTCCGTTGAGGGTTAATTCCGGTGAA
CCTGACCCGGTTCGGATCACGTCAAGAGATCTTCTTCGTCGTCGTCGTCGTCGTCCTCTT
CTACGTCGTCGTCTGAAAACGGGAAGTTGAAACGAAGGAGAAAAGCAGAGAATCTGACGT
CGGAGGTGGTGCAGGTGAAGTGTGAGGTTGGTGATGAGACACGTGTTGATGAGTTATTGG
TTTCATAA

Figure 13

>SEQ8-AtERF2PRT
MYGQCNIESDYALLESITRHLLGGGGENELRLNESTPSSCFTESWGGLPLKENDSEDMLVYGL
LKDAFHFDTSSSDLSCLFDFPAVKVEPTENFTAMEEKPKKAIPVTETAVKAKHYRGVRQRPWG
KFAAEIRDPAKNGARVWLGTFETAEDAALAYDIAAFRMRGSRALLNFPLRVNSGEPDPVRITSK
RSSSSSSSSSSSTSSSENGKLKRRRKAENLTSEVVQVKCEVGDETRVDELLVS*

PHACOSPORACEA RESISTANT SOYBEAN PLANTS

This application is a continuation of U.S. application Ser. No. 14/128,142, which is a National Stage application of International Application No. PCT/IB2012/053193, filed Jun. 25, 2012, which claims the benefit of U.S. Provisional Application No. 61/501,274, filed Jun. 27, 2011; this application also claims priority under 35 U.S.C. § 119 to European Patent Application No. 11171484.6, filed Jun. 27, 2011. The contents of all of these applications are hereby incorporated by reference herein in their entirety.

The Sequence Listing, which is a part of the present disclosure, is submitted concurrently with the specification as a text file. The name of the text file containing the Sequence Listing is "72293A_Seqlisting.txt", which was created on Aug. 29, 2017 and is 157,636 bytes in size. The subject matter of the Sequence Listing is incorporated herein in its entirety by reference.

The present invention relates to a method of increasing resistance against fungal pathogens of the family Phacosporaceae in transgenic plants and/or plant cells. In these plants, the ethylene signaling pathway and/or activity of the ethylene signaling compounds is changed. This is achieved by priming the ethylene signaling pathway in these plants in comparison to wild type plants and/or wild type plant cells. Depending on the activating or inhibitory function of a particular signaling compound overexpression or knockdown of the cognate gene might be used.

Furthermore, the invention relates to transgenic plants and/or plant cells having an increased resistance against fungal pathogens of the family Phacosporaceae, for example soybean rust and to recombinant expression vectors comprising a sequence that is identical or homologous to a sequence encoding a functional ethylene signaling compound or fragments thereof.

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally means the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms. In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular such a resistance works for different strains of the pathogen.

Immediately after recognition of a potential pathogen the plant starts to elicit defense reactions. Mostly the presence of the pathogen is sensed via so called PAMP receptors, a class of transmembrane receptor like kinases recognizing conserved pathogen associated molecules (e.g. flagellin or chitin). Downstream of the PAM P receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects). In most plant pathogen interactions ET has been shown to act synergistic to JA and antagonistic to the "biotrophic" defense of SA. For example the well-known JA marker protein PDF1.2 needs the activation of both ET and JA to be up-regulated during defense against necrotrophic pathogens. The crucial involvement of the JA/ET pathway in resistance against necrotrophic pathogens is corroborated by the fact that the overexpression of ERF1, a central protein involved in ET signaling (see FIG. 1) leads to an enhanced resistance against the necrotrophic fungi *Botrytis cinerea, Fusarium oxysporum* and *Plectosphaerella cucumerina* (Berrocal-Lobo et al. 2002, Plant Journal 29:23-32, Berrocal-Lobo and Molina 2004, MPMI 17:763ff). On the other hand priming of the ET signaling pathway by overexpression of ERF1 increases the susceptibility of *Arabidopsis* against the biotrophic pathogen *Pseudomonas syringae* (Berrocal-Lobo et al. 2002, Plant Journal 29:23-32) proving the proposed model that the JA/ET interacts negatively with the SA pathway to balance the nature of the defense reactions according to the attacking pathogen allowing the plant to tailor its defense response. Hence it was generally believed that priming of the ET signaling pathway leads to increased resistance to necrotrophic fungi but at the same time to an increased susceptibility to biotrophic pathogens.

Fungi are distributed worldwide. Approximately 100 000 different fungal species are known to date. The rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

Soybean rust has become increasingly important in recent times. The disease may be caused by the biotrophic rusts *Phakopsora pachyrhizi* (Sydow) and *Phakopsora meibomiae* (Arthur). They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant plants, four dominant genes Rpp1-4, which mediate resistance of soy to *P. pachyrhizi*, were discovered. The resistance was lost rapidly, as *P. pychyrhizi* develops new virulent races.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

Surprisingly we found that the biotrophic fungal pathogens of the family Phacosporaceae, for example soybean rust fungus can be controlled by using the ethylene mediated defense, although prior art teaches, that priming the ethylene mediated defense leads to increased susceptibility to biotrophic fungi (Berrocal-Lobo et al. 2002, Plant Journal 29:23-32). We primed the ET pathway either by overexpression of several proteins involved in ethylene signaling or by downregulation of several proteins involved in suppression of the ET signaling pathway. Generally one should expect that the priming of the ET signaling pathway should lead to enhanced susceptibility against Asian Soybean Rust (ASR), as the ET signaling pathway negatively interacts with the biotrophic defense associated SA pathway. On the other hand one should expect enhanced resistance to ASR by inhibiting the ET signaling pathway, and therefore debottlenecking the SA pathway. Surprisingly we found the ET signaling pathway itself enhances the resistance against soybean rust. Overexpression of several proteins involved in ET signaling pathway (ERF1, ERF2, Pti4, Pti5) increases the resistance of soybean against fungal pathogens of the family Phacosporaceae, for example soybean rust. Downregulation of ET signaling pathway antagonisitc proteins like CTR1 and EBF1 also increases the resistance of soybean to fungal pathogens of the family Phacosporaceae for example soybean rust. Vice versa the overexpression of ET signaling pathwayantagonisitc proteins like CTR1 and EBF1 increases the susceptibility of soybean to fungal pathogens of the family Phacosporaceae for example soybean rust. This clearly demonstrates the positive influence of the ET mediated defense pathways to the resistance of soybean against fungal pathogens of the family Phacosporaceae for example soybean rust.

The object of the present invention is to provide a method of increasing resistance against fungal pathogens of the family Phacosporaceae, preferably against fungal pathogens of the genus *Phacospora*, most preferably against *Phakopsora pachyrhizi* (Sydow) and *Phakopsora meibomiae* (Arthur), also known as soy bean rust in transgenic plants and/or transgenic plant cells by using the ethylene signaling pathway, especially by priming the ethylene signaling pathway. This may be achieved by overexpressing one or more nucleic acid of the invention in order to prime the ethylene signaling pathway or downregulating of one or more nucleic acids of the invention that would also lead to the priming of the ethylene signaling pathway or a combination of both, which in turn would lead to increased resistance to fungal pathogens of the family Phacosporaceae for example soybean rust.

The nucleic acids of the invention to be overexpressed in order to prime the ethylene signaling pathway and to achieve increased resistance to fungal pathogens of the family Phacosporaceae for example soybean rust are Pti4, Pti5, ERF1 and/or ERF2 as for example defined by any of SEQ ID NO: 1, 3, 5 or 7 or any homolog, derivative or orthologue or paralogue thereof. The priming of the ethylene signaling pathway may also be achieved by the downregulation of repressors of any of Pti4, Pti5, ERF1 and/or ERF2 such as microRNAs or ta-siRNAs targeting these genes.

The nucleic acids of the invention to be downregulated in order to prime the ethylene signaling pathway and to achieve increased resistance to fungal pathogens of the family Phacosporaceae for example soybean rust are CTR1, EBF1 and/or EBF2 as for example defined by any of SEQ ID NO: 9, 11, 13, 15, 17, 19, 21 or 23 or any fragment, homolog, derivative or orthologue or paralogue thereof. The priming of the ethylene signaling pathway may also be achieved by the overexpression of repressors of any of CTR1, EBF1 and/or EBF2 such as microRNAs or tasiRNAs targeting these genes.

A further object is to provide transgenic plants resistant against fungal pathogens of the family Phacosporaceae, preferably against fungal pathogens of the genus Phacospora, most preferably against *Phakopsora pachyrhizi* (Sydow) and *Phakopsora meibomiae* (Arthur), also known as soybean rust, a method for producing such plants as well as a vector construct useful for the above methods. This object is achieved by the subject-matter of the main claims. Preferred embodiments of the invention are defined by the features of the sub-claims.

Definitions

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

The term "priming" is to be understood as sensitization of a plant or part thereof to future attack by pests or pathogens in order to induce a resistance against such pests or pathogens. The resistance induced by priming is not based on a direct activation of a defense mechanism, but on a sensitization of the plant or tissue of the plant that results in a faster and stronger expression of defense mechanisms compared to an unprimed plant once the plant is exposed to pathogen attack. "Priming" refers herein to the sensitization of a plant or part of a plant so that is able to activate defense mechanisms faster and/or stronger when exposed to one or more biotic stresses compared to a non-primed control plant or part thereof which must rely on a direct defense response. Without limiting the scope of the invention, it is believed that priming results in an increased level of signaling factors such as transcription factor (TF) proteins or MAP Kinases and the like in the primed plant or plant tissue compared to non-primed plants or plant tissues. Upon subsequent exposure of the plant or plant tissue to stress such as pest or pathogen attack, these inactive TF proteins become active and regulate gene expression of defense genes, such that a faster and/or stronger defense response is mounted by primed plants or tissues compared to unprimed plants or tissues. Priming may for the application at hand additionally be understood as a constitutive activation of the respective defense mechanism.

The term "priming of the ethylene signaling pathway" means that the effect of priming is achieved by sensitization of the ethylene signaling pathway as shown in FIG. 1 which leads to a faster and stronger defense response of the ethylene dependent defense mechanisms of the plant or plant tissue. The sensitization of the ethylene signaling pathway may be achieved by enhancing the expression of Pti4, Pti5, ERF1 and/or ERF2 protein and/or by suppression of expression of CTR1, EBF1 and/or EBF2 protein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular homologues of a nucleic acid encompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers a replacement of nucleic acid with other nucleic acids, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

| Examples of conserved amino acid substitutions | |
|---|---|
| Residue | Conservative Substitutions |
| Ala | Ser |
| Arg | Lys |

TABLE 1-continued

Examples of conserved amino acid substitutions

| Residue | Conservative Substitutions |
|---|---|
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in sflico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms "soybean rust-resistance", "resistant to a soybean rust", "soybean rust-resistant", "rust-resistance", "resistant to a rust", "rust-resistant", "fungal-resistance", "resistant to a fungus" and/or "fungal-resistant" mean reducing or preventing an infection by Phacosporacea, in particular *Phakopsora pachyrhizi* (Sydow) and *Phakopsora meibomiae* (Arthur) also known as soybean rust or Asian Soybean Rust (ASR). The term "resistance" refers to soybean resistance. Resistance does not imply that the plant necessarily has 100% resistance to infection. In preferred embodiments, the resistance to infection by soy bean rust in a resistant plant is greater than 10%, 20%, 30%, 40%, 50%, 60%, 70%, 80%, 90%, or 95% in comparison to a wild type plant that is not resistant to soybean rust. Preferably the wild type plant is a plant of a similar, more preferably identical, genotype as the plant having increased resistance to the soybean rust, but does not comprise a recombinant nucleic acid of the invention, functional fragments thereof and/or a nucleic acid capable of hybridizing with a nucleic acid of the invention.

The terms "soybean rust-resistance", "resistant to a soybean rust", "soybean rust-resistant", "rust-resistance", "resistant to a rust", "rust-resistant", fungal-resistance, resistant to a fungus" and/or "fungal-resistant" as used herein refers to the ability of a plant, as compared to a wild type plant, to avoid infection by fungal pathogens of the family Phacosporaceae, for example of the genus Phacospora, such as *Phakopsora pachyrhizi* (Sydow) and *Phakopsora meibomiae* (Arthur), also known as soybean rust, to kill rust, to hamper, to reduce, to delay, to stop the development, growth and/or multiplication of soybean rust. The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae* PHYTOPATHOLOGY 92(2) 217-227). Preferably, the soybean rust resistance is nonhost-resistance. Nonhost-resistance means that the plants are resistant to at least 80%, at least 90%, at least 95%, at least 98%, at least 99% and preferably 100% of the strains of the soybean rust pathogen, preferably the strains of *Phakopsora pachyrhizi*.

The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term stringency conditions refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0,1×SSC, 0.1% SDS at 50° C. or 65° C., preferably 65° C. Preferably, the complementary nucleotides hybridize with a fragment or the whole nucleic acids of the invention. Preferably, the complementary polynucleotide hybridizes with parts of the nucleic acids of the invention capable to provide soybean rust resistance by overexpression or downregulation, respectively.

As used herein, the term "nucleic acid of the invention" or "amino acid of the invention" refers to a gene having at least 60% identity with any of SEQ-ID-No. 1, 3, 5, 7, 9, 11, 13, 15, 17, 19, 21 or 23 or with a sequence coding for a protein having at least 60% identity with SEQ-ID-No. 2, 4, 6, 8, 10, 12, 14, 16, 18, 20, 22 or 24 and/or functional fragments thereof. In one embodiment homologues of the nucleic acids of the invention have, at the DNA level and/or protein level, at least 70%, preferably of at least 80%, especially preferably of at least 90%, quite especially preferably of at least 95%, quite especially preferably of at least 98%, 99% or 100% identity over the entire DNA region or protein region given in a sequence specifically disclosed herein and/or a functional fragment thereof.

As used herein, the term "amino acid of the invention" refers to a protein having at least 60% identity to a sequence coding for a protein having SEQ-ID-No. 2, 4, 6, 8, 10, 12, 14, 16, 18, 20, 22 or 24 and/or a fragment thereof. In one embodiment homologues of the amino acids of the invention have at least 70%, preferably of at least 80%, especially preferably of at least 90%, quite especially preferably of at least 95%, quite especially preferably of at least 98%, 99% or 100% identity over the entire protein region given in a sequence specifically disclosed herein and/or a functional fragment thereof.

"Identity" or "homology" between two nucleic acids and/or refers in each case over the entire length of the nucleic acid of the invention.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple alignment parameter:

Gap opening penalty 10
Gap extension penalty 10
Gap separation penalty range 8
Gap separation penalty off
% identity for alignment delay 40
Residue specific gaps off
Hydrophilic residue gap off
Transition weighing 0

Pairwise alignment parameter:

FAST algorithm on
K-tuple size 1
Gap penalty 3
Window size 5
Number of best diagonals 5

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings DNA Gap Open Penalty 15.0
DNA Gap Extension Penalty 6.66
DNA Matrix Identity
Protein Gap Open Penalty 10.0
Protein Gap Extension Penalty 0.2
Protein matrix Gonnet
Protein/DNA ENDGAP −1
Protein/DNA GAPDIST 4

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid useful according to the present invention and the nucleic acids of the invention may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). At least 60% sequence identity, preferably at least 70% sequence identity, 80% 90%, 95%, 98%, 99% sequence identity, or even 100% sequence identity, with the nucleic acids having any of SEQ-ID-No. 1, 3, 5, 7, 9, 11, 13, 15, 17, 19, 21 or 23 is preferred.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the recombinant nucleic acids of the invention. In one embodiment, the seeds are true breeding for an increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C.O. Lehm), sugar pea (*Pisum sativum* L. convar. axiphium Alef emend. C.O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.)); goa bean (*Psophocarpus tetragonolobus* (L.) DC.), African yam bean (*Sphenostylis stenocarpa* (Hochst. ex A. Rich.) Harms), Egyptian black bean, dolichos bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.)).

Reference herein to an "endogenous" nucleic acid of the invention" refers to the gene in question as found in a plant in its natural form (i.e., without there being any human intervention). Recombinant nucleic acid of the invention refers to the same gene (or a substantially homologous nucleic acid/gene) in an isolated form subsequently (re) introduced into a plant (a transgene). For example, a transgenic plant containing such a transgene may, when compared to the expression of the endogenous gene, encounter a substantial increase of the transgene expression or down-regulation of the corresponding endogene respectively. The isolated gene may be isolated from an organism or may be manmade, for example by chemical synthesis. A transgenic plant according to the present invention includes a recombinant nucleic acid of the invention integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more nucleic acids of the invention, all those constructions brought about by man by gentechnological methods in which either (a) the sequences of the nucleic acids of the invention or a part thereof, or
(b) genetic control sequence(s) which is operably linked with the—nucleic acid sequence of the invention according to the invention, for example a promoter, or
(c) a) and b)

are not located in their natural genetic environment or have been modified by man by gentechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

It shall further be noted that in the context of the present invention, the term "isolated nucleic acid" or "isolated protein" may in some instances be considered as a synonym for a "recombinant nucleic acid" or a "recombinant protein", respectively and refers to a nucleic acid or protein that is not located in its natural genetic environment and/or that has been modified by gentechnical methods.

As used herein, the term "transgenic" preferably refers to any plant, plant cell, callus, plant tissue, or plant part that contains the recombinant construct or vector or expression cassette of the invention or a part thereof which is preferably introduced by non-essentially biological processes, preferably Agrobacteria transformation. The recombinant construct or a part thereof is stably integrated into a chromosome, so that it is passed on to successive generations by clonal propagation, vegetative propagation or sexual propagation. Said successive generations are also transgenic. Essentially biological processes may be crossing of plants and/or natural recombination.

A transgenic plant, plants cell or tissue for the purposes of the invention is thus understood as meaning that the recombinant construct or vector or expression cassette of the invention is integrated into the genome.

Preferably, constructs or vectors or expression cassettes of the invention are not present in the genome of the original plant or are present in the genome of the transgenic plant not at their natural locus of the genome of the original plant.

Natural locus means the location on a specific chromosome, preferably the location between certain genes, more preferably the same sequence background as in the original plant which is transformed.

Preferably, the transgenic plant, plant cell or tissue thereof expresses the constructs or expression cassettes of the invention.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), a regulatory RNA (e.g. microRNA, siRNA, ta-siRNA) or mRNA with or without subsequent translation of the latter into a protein. The process includes transcription of DNA and processing of the resulting RNA product.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a nonheterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid and/or protein which comprises merely a part of the full-length nucleic acid and/or fulllength protein but still provides the same function, i.e. soybean rust resistance when expressed or repressed in a plant respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid and/or original protein.

In one embodiment the fragment of any of the nucleic acids of the invention has an identity as defined above over a length of at least 20%, at least 30%, at least 50%, at least 75%, at least 90% of the nucleotides of the respective nucleic acid of the invention to the respective nucleic acid of the invention.

In cases where overexpression of nucleic acid of the invention is desired, the term "similar functional activity" or "similar function" means that any homologue and/or fragment provide soybean rust resistance when expressed in a plant. Preferably similar functional activity means at least 50%, at least 60%, at least 70%, at least 80%, at least 90%, at least 95%, at least 98%, at least 99% or 100% or higher of the soybean rust resistance compared with functional activity provided by the recombinant expression of any of the nucleotide sequences of the invention as defined by SEQ-ID No. 1, 3, 5, 7, 9, 11, 13, 15, 17, 19, 21 or 23 and/or recombinant protein of the invention as defined by SEQ-ID No. 2, 4, 6, 8, 10, 12, 14, 16, 18, 20, 22 or 24.

The term "increased activity" as used herein means any protein having increased activity provides an increased soybean rust resistance compared with the wildtype plant merely expressing the respective endogenous nucleic acid of the invention. As far as overexpression is concerned, for the purposes of this invention, the original wild-type expression level might also be zero (absence of expression).

"Repress" or "downregulate" or "suppress" the expression of a nucleic acid molecule in a plant cell are used equivalently herein and mean that the level of expression of the nucleic acid molecule or the level of protein activity of the protein encoded by the nucleic acid molecule in a plant, part of a plant or plant cell after applying a method of the present invention is lower than its expression in the plant, part of the plant or plant cell before applying the method, or compared to a reference plant lacking a recombinant nucleic acid molecule of the invention. The term "repressed" or "downregulated" or "suppressed" as used herein are synonymous and means herein lower, preferably significantly lower expression of the nucleic acid molecule to be expressed or activity of the protein to be expressed. As used herein, a "repression" or "downregulation" or "suppression" of the level of an agent such as a protein, mRNA or RNA means that the level is reduced relative to a substantially identical plant, part of a plant or plant cell grown under substantially identical conditions, lacking a recombinant nucleic acid molecule of the invention, for example lacking the region complementary to at least a part of the precursor molecule of the srRNA, the recombinant construct or recombinant vector of the invention. As used herein, "repression" or "downregulation" or "suppression" of the level of an agent, such as for example a preRNA, mRNA, rRNA, tRNA, snoRNA, snRNA expressed by the target gene and/or of the protein product encoded by it, means that the amount is reduced 10% or more, for example 20% or more, preferably 30% or more, more preferably 50% or more, even more preferably 70% or more, most preferably 80% or more for example 90% relative to a cell or organism lacking a recombinant nucleic acid molecule of the invention. The repression or downregulation can be determined by methods with which the skilled worker is familiar. Thus, the downregulation, repression or suppression of the nucleic acid or protein or protein activity quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a plant or plant cell. Depending on the type of the target protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

A method for increasing resistance to Phacosporacea, for example soy bean rust wherein the ethylene signaling pathway is primed in comparison to wild-type plants or wild-type plant cells by enhancing the expression of a Pti4, Pti5, ERF1 and/or ERF2 protein or a functional fragment, orthologue, paralogue or homologue thereof is one embodiment of the invention.

A method for increasing resistance to Phacosporacea, for example soy bean rust wherein the priming of the ethylene signaling pathway may be achieved by enhancing the expression of a Pti4, Pti5, ERF1 and/or ERF2 protein or a functional fragment, orthologue, paralogue or homologue thereof wherein the Pti4, Pti5, ERF1 and/or ERF2 protein is encoded by (i) a recombinant nucleic acid having at least 60% identity preferably at least 70% sequence identity, 80% 90%, 95%, 98%, 99% sequence identity, or even 100% sequence identity with SEQ ID No. 1, 3, 5 or 7, a functional fragment thereof and/or a recombinant nucleic acid capable of hybridizing under stringent conditions with such nucleic acids thereof and/or by (ii) a recombinant nucleic acid encoding a protein having at least 60% preferably at least 70% sequence identity, 80% 90%, 95%, 98%, 99% sequence identity, or even 100% sequence identity with SEQ ID No. 2, 4, 6 or 8, a functional fragment thereof, an orthologue and/or a paralogue thereof is a further embodiment of the invention.

In a further method of the invention, the priming of the ethylene signaling pathway is achieved by a method comprising the steps of (a) stably transforming a plant cell with an expression cassette comprising
  (i) a recombinant nucleic acid having at least 60% identity preferably at least 70% sequence identity, 80% 90%, 95%, 98%, 99% sequence identity, or even 100% sequence identity with SEQ-ID-No. 1, 3, 5 or 7 and/or a functional fragment thereof and/or a recombinant nucleic acid capable of hybridizing under stringent conditions with such nucleic acids thereof and/or
  (ii) a recombinant nucleic acid coding for a protein having at least 60% identity preferably at least 70% sequence identity, 80% 90%, 95%, 98%, 99% sequence identity, or even 100% sequence identity with SEQ ID No. 2, 4, 6 or 8, a functional fragment thereof, an orthologue and/or a paralogue thereof in functional linkage with a promoter;

(b) regenerating the plant from the plant cell; and
(c) expressing said recombinant nucleic acid which codes for a Pti4, Pti5, ERF1 and/or ERF2 protein in an amount and for a period sufficient to generate or to increase soybean rust resistance in said plant.

A recombinant vector construct comprising:

(a) (i) recombinant nucleic acid having at least 60% identity preferably at least 70% sequence identity, 80% 90%, 95%, 98%, 99% sequence identity, or even 100% sequence identity with SEQ ID No. 1, 3, 5 or 7, a functional fragment thereof and/or a nucleic acid capable of hybridizing under stringent conditions with such a nucleic acid and/or
  (ii) a recombinant nucleic acid coding for a protein having at least 60% identity preferably at least 70% sequence identity, 80% 90%, 95%, 98%, 99% sequence identity, or even 100% sequence identity with SEQ ID No. 2, 4, 6 or 8, a functional fragment thereof, an orthologue and/or a paralogue thereof operably linked with (b) a promoter and
(c) a transcription termination sequence is a further embodiment of the invention.

As used herein the term "target nucleic acid" preferably refers to a DNA-molecule capable to prevent the expression, reduce the amount and/or function of the plant CTR1, EBF1 and/or EBF2 gene as for example defined by SEQ ID NO: 9, 11, 13, 15, 17, 19, 21 or 23 in the plant or parts of the plant.

The term "target gene" as used herein refers to a gene the expression of which is to be downregulated or suppressed. In the frame of this application, target genes are preferably plant CTR1, EBF1 and/or EBF2 gene as for example defined by SEQ ID NO: 9, 11, 13, 15, 17, 19, 21 or 23 or homologues, paralogues or functional equivalents thereof.

The present invention provides a method for increasing resistance to fungal pathogens of the family Phacosporaceae, preferably against fungal pathogens of the genus Phacospora, most preferably against *Phakopsora pachyrhizi* (Sydow) and *Phakopsora meibomiae* (Arthur), also known as soy bean rust in plants and/or plant cells, wherein the ethylene signaling pathway is primed in comparison to wild type plants and/or wild type plant cells by downregulation or suppression of expression of a CTR1, EBF1 and/or an EBF2 protein.

In one embodiment of the invention, the CTR1, EBF1 and/or EBF2 protein is encoded by (i) a recombinant nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID No. 9, 11, 13, 15, 17, 19, 21 or 23, a functional fragment thereof and/or a recombinant nucleic acid capable of hybridizing under stringent conditions with such nucleic acids thereof and/or by (ii) a recombinant nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID No. 10, 12, 14, 16, 18, 20, 22 or 24, a functional fragment thereof, an orthologue and/or a paralogue thereof.

A method for increasing resistance to fungal pathogens of the family Phacosporaceae, preferably against fungal pathogens of the genus *Phacospora*, most preferably against *Phakopsora pachyrhizi* (Sydow) and *Phakopsora meibomiae* (Arthur), also known as soy bean rust in plants and/or plant cells, wherein the ethylene signaling pathway is primed in comparison to wild type plants and/or wild type plant cells by downregulation or suppression of expression of a CTR1, EBF1 and/or an EBF2 protein is comprising the steps of a) providing a recombinant nucleic acid comprising a target nucleic acid that is substantial identical and/or substantially complementary to at least 19 contiguous nucleotides of the target CTR1, EBF1 and/or EBF2-gene or a homolog, paralogue or ortholog thereof as defined above, b) introducing said recombinant nucleic acid into in the plant and/or part thereof is a further embodiment of the invention It is a further embodiment of the invention, that in the method as defined above, the recombinant nucleic acid is able to provide dsRNA and/or si-RNA and/or miRNA in the plant, a part thereof, once the recombinant nucleic acid is expressed, wherein at least 19, preferably at least 20, more preferably at least 21, for example 22 or 23 contiguous nucleotides of the dsRNA and/or siRNA and/or miRNA are substantially complementary to the target CTR1, EBF1 and/or EBF2-gene.

In a specific embodiment of the method of the invention as defined above, said recombinant nucleic acid comprises a promoter that is functional in the plant cell, operably linked to a target nucleic acid which is substantial identical and/or substantially complementary to at least 19, preferably at least 20, more preferably at least 21, for example 22 or 23 contiguous nucleotides of the target CTR1, EBF1 and/or EBF2-gene and which, when it is transcribed, generates RNA comprising a first strand having a sequence substantially complementary to at least 19 preferably at least 20, more preferably at least 21, for example 22 or 23 contiguous nucleotides of the target CTR1, EBF1 and/or EBF2-gene and a second strand having a sequence substantially complementary to the first strand or parts thereof, and a terminator regulatory sequence.

In another specific embodiment of the method of the invention as defined above said recombinant nucleic acid comprises a promoter that is functional in the plant cell, operably linked to a target nucleic acid which, when it is transcribed, generates RNA comprising a first strand having a sequence substantially identical or substantially complementary to at least contiguous 19 preferably at least 20, more preferably at least 21, for example 22 or 23 nucleotides of the target CTR1, EBF1 and/or EBF2-gene, and a terminator regulatory sequence.

Further embodiments of the invention are recombinant vector constructs comprising a recombinant nucleic acid comprising a promoter that is functional in the plant cell, operably linked to a target nucleic acid which is substantially identical and/or substantially complementary to at least 19 preferably at least 20, more preferably at least 21, for example 22 or 23 contiguous nucleotides of the target CTR1, EBF1 and/or EBF2-gene and a terminator regulatory sequence.

The recombinant vector constructs of the invention as defined above may further comprise a promoter that is functional in the plant cell, operably linked to a target nucleic acid which is substantial identical and/or substantially complementary to at least 19 preferably at least 20, more preferably at least 21, for example 22 or 23 contiguous nucleotides of the target CTR1, EBF1 and/or EBF2-gene and which, when it is transcribed, generates RNA comprising a first strand having a sequence substantially complementary to at least 19 preferably at least 20, more preferably at least 21, for example 22 or 23 contiguous nucleotides of the target CTR1, EBF1 and/or EBF2-gene and optionally a second strand having a sequence at substantially complementary to the first strand or parts thereof, and a terminator regulatory sequence.

The present invention provides a method for producing a plant and/or a part thereof resistant to fungal pathogens of the family Phacosporaceae for example soybean rust comprising a) providing a recombinant nucleic acid comprising a target nucleic acid that is substantial identical and/or substantial complementary to at least contiguous 19 preferably at least 20, more preferably at least 21, for example 22 or 23 nucleotides of the target sequence of the invention, b) introducing said recombinant nucleic acid into in the plant and/or parts thereof, wherein the introduction of said recombinant nucleic acid results in downregulation or repression of the expression of the respective target gene. Such target genes are preferably CTR1, EBF1 and EBF2 and homologues, paralogues or functional equivalents thereof as for example defined by SEQ ID NO: 9, 11, 13, 15, 17, 19, 21 or 23.

The present invention further provides a vector construct comprising a recombinant nucleic acid comprising a promoter that is functional in the plant cell, operably linked to a target nucleic acid which is substantial identical and/or substantial complementary, preferably identical or complementary to at least 19 preferably at least 20, more preferably at least 21, for example 22 or 23 contiguous nucleotides of the target gene of the invention and a terminator regulatory sequence as well as the use of the vector construct for the transformation of plants or parts thereof to provide plants resistant to fungal pathogens of the family Phacosporaceae for example soybean rust.

The present invention also provides a transgenic plant cell, plants or parts thereof comprising a recombinant nucleic acid comprising a target nucleic acid that is substantial identical and/or substantial complementary, preferably identical or complementary to at least contiguous 19 preferably at least 20, more preferably at least 21, for example 22 or 23 nucleotides of the target gene of the invention. Parts of plants may be plant cells, roots, stems, leaves, flowers and/or seeds.

There is general agreement that in many organisms, including fungi and plants, large pieces of dsRNA complementary to a specific gene are cleaved into 19-24 nucleotide fragments (siRNA) within cells, and that these siRNAs are the actual mediators for silencing the specific target gene. As used herein siRNA refers to 19-24 nucleotide fragments complementary to the respective target gene.

There are several possibilities to provide the siRNA: RNA-interference (RNAi), micro-RNAi (miRNA), sense RNA and/or antisense RNA for downregulation or suppression of the expression of a target gene of the invention.

As used herein, "RNAi" or "RNA interference" refers to the process of sequence-specific post-transcriptional gene silencing, mediated by double-stranded RNA (dsRNA). In the RNAi process, dsRNA comprising a first strand that is substantially complementary to at least 19 contiguous nucleotides of the target gene of the invention and a second strand that is complementary to the first strand at least partially has to be provided. For this purpose a recombinant nucleic acid is introduced into the plant, which is capable to produce such dsRNA. The target gene-specific dsRNA is produced and processed into relatively small fragments (siRNAs). miRNA refers to a similar process, except that the produced dsRNA only partially comprises regions substantially identical to the target-gene (at least 19 contiguous nucleotides).

As used herein, "antisense interference" refers to the process of sequence-specific post-transcriptional gene silencing, probably also mediated by double-stranded RNA (dsRNA). In the antisenseRNA-process, ssRNA comprising a first strand that is substantially complementary to at least 19 contiguous nucleotides of the target gene has to be provided. For this purpose recombinant nucleic acid is introduced into the plant, which is capable to produce such ssRNA. Without to be bound by the theory, it is assumed that this RNA pairs with complementary ssRNA transcribed from the original target gene.

As disclosed herein, 100% sequence identity between the target nucleic acid and the target gene is not required to practice the present invention. Preferably, the target nucleic acid comprises a 19-nucleotide portion which is substantially identical and/or substantially complementary to at least 19 contiguous nucleotides of the target gene. While a target nucleic acid comprising a nucleotide sequence identical and/or identical to a portion of the target gene and/or complementary to the whole sequence and/or a portion of the target gene is preferred for inhibition, the invention can tolerate sequence variations that might be expected due to gene manipulation or synthesis, genetic mutation, strain polymorphism, or evolutionary divergence. Thus the target nucleic acid may also encompass a mismatch with the target gene of at least 1, 2, or more nucleotides. For example, it is contemplated in the present invention that within 21 contiguous nucleotides the target nucleic acid may contain an addition, deletion or substitution of 1, 2, or more nucleotides, so long as the resulting RNA sequence still interferes with the respective target gene function.

Sequence identity between the recombinant nucleic acid useful according to the present invention and the target gene may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 80% sequence identity, 90% sequence identity, or even 100% sequence identity, between the target nucleic acid and at least 19 contiguous nucleotides of the target gene is preferred. The same preferably applies for the sequence complementarity.

When the target nucleic acid of the invention has a length longer than about 19 nucleotides, for example from about 50 nucleotides to about 500 nucleotides, the corresponding dsRNA provided therefrom will be cleaved randomly to dsRNAs of about 21 nucleotides within the plant cell: the siRNAs. Multiple specialized Dicers in plants may generate siRNAs typically ranging in size from 19nt to 24nt (See Henderson et al., 2006. Nature Genetics 38:721-725.). The cleavage of a longer dsRNA of the invention may yield a pool of 21mer dsRNAs, derived from the longer dsRNA. The siRNAs may have sequences corresponding to fragments of 19-24 contiguous nucleotides across the entire sequence of the target gene. One of skill in the art would recognize that the siRNA can have a mismatch with the target gene of at least 1, 2, or more nucleotides. Further, these mismatches are intended to be included in the present invention.

In one embodiment the target nucleic acid is substantial identical and/or substantial complementary, preferably identical or complementary over a length of at least 19, at least 50, at least 100, at least 200, at least 300, at least 400 or at least 500 nucleotides to the respective target gene. In particular, the target nucleic acid may comprise 19 to 500, preferably 50 to 500, more preferably 250 to 350 nucleotides, wherein preferably at least about 19, 20, 21, 22, 23, 24, 25, 50, 100, 200, 300, 400, consecutive bases or up to the full length of target nucleic acid are identical and/or complementary and/or identical to the target gene.

Preferably, the recombinant nucleic acid is able to provide dsRNA and/or siRNA and/or miRNA in the plant, a part thereof once the recombinant nucleic acid is expressed in the plant, wherein preferably at least 19 contiguous nucleotides of the dsRNA and/or si RNA and/or miRNA are substantially complementary to the respective target gene.

Generally, the term "substantially identical" or "substantially complementary" preferably refers to DNA and/or RNA which is at least 80% identical or complementary to 19 or more contiguous nucleotides of a specific DNA or RNA sequence of the respective target gene, more preferably, at least 90% identical to 19 or more contiguous nucleotides, and most preferably at least 95%, at least 96%, at least 97%, at least 98% or at least 99% identical or complementary or absolutely identical or absolutely complementary to 19 or more contiguous nucleotides of a specific DNA or RNA-sequence of the respective target gene. In particular the identical RNA corresponds to the coding DNA-strand of the respective target gene.

As used herein, the term "substantially identical" or "substantially complementary" as applied to DNA of the recombinant nucleic acid, the target nucleic acid and/or the target gene means that the nucleotide sequence is at least 80% identical or complementary to 19 or more contiguous nucleotides of the target gene, more preferably, at least 90% identical or complementary to 19 or more contiguous nucleotides of the target gene, and most preferably at least 95%, at least 96%, at least 97%, at least 98% or at least 99% identical or complementary or absolutely identical or absolutely complementary to 19 or more contiguous nucleotides of the target gene. The term "19 or more contiguous nucleotides of the target gene" corresponds to the target gene, being at least about 19, 20, 21, 22, 23, 24, 25, 50, 100, 200, 300, 400, 500, 1000, 1500, consecutive bases or up to the full length of the target gene.

One embodiment according to the present invention, provides a method for producing a plant and/or a part thereof resistant to a fungal pathogen of the family Phacosporaceae, for example soybean rust, wherein the recombinant nucleic acid comprises
a promoter that is functional in the plant cell, operably linked to
a target nucleic acid which is substantial identical and/or substantial complementary, or preferably identical or complementary to at least 19 preferably at least 20, more preferably at least 21, for example 22 or 23 contiguous nucleotides of the respective target gene and which, when it is transcribed, generates RNA comprising a first strand having a sequence substantially complementary to at least 19 preferably at least 20, more preferably at least 21, for example 22 or 23 contiguous nucleotides of the target gene and a second strand having a sequence substantially complementary to the first strand and/or parts thereof, and a terminator regulatory sequence.

The first strand and the second strand may at least partially form dsRNA. This technique is also referred to as RNAi.

In another embodiment the target nucleic acid comprises 19 to 24 contiguous nucleotides of the target sequence which are substantially identical and/or substantially complementary to the target gene and the remaining nucleotides of the target nucleic acid are not identical and/or not complementary to the target gene. Not-identical means an identity which is lower than 95%, lower that 90%, lower than 80%, lower than 70%, lower than 60% over the whole sequence of the target nucleic acid. Not-complementary means a complementarity which is lower than 95%, lower that 90%, lower than 80%, lower than 70%, lower than 60% over the whole sequence of the target nucleic acid. This technique is also referred to as miRNA.

One embodiment according to the present invention, provides a method for producing a plant and/or a part thereof resistant to a fungal pathogens of the family Phacosporaceae, for example soybean rust, wherein the recombinant nucleic acid comprises a promoter that is functional in the plant cell, operably linked to a target nucleic acid which, when it is transcribed, generates RNA comprising a first strand having a sequence substantially complementary, preferably complementary to at least contiguous 19 preferably at least 20, more preferably at least 21, for example 22 or 23 nucleotides of the target gene, and a terminator regulatory sequence.

Preferably, the first strand generated in the plant forms dsRNA together with a second RNA-strand generated in the plant which is complementary to the first strand. This technique is also referred to as antisense RNA.

The dsRNA of the invention may optionally comprise a single stranded overhang at either or both ends. Preferably, the single stranded overhang comprises at least two nucleotides at the 3' end of each strand of the dsRNA molecule. The double-stranded structure may be formed by a single self-complementary RNA strand (i.e. forming a hairpin loop) or two complementary RNA strands. When the dsRNA of the invention forms a hairpin loop, it may optionally comprise an intron, as set forth in US 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559.

In one embodiment the vector construct comprises a promoter that is functional in the plant cell, operably linked to a target nucleic acid which is substantial identical and/or substantial complementary to at least 19 preferably at least 20, more preferably at least 21, for example 22 or 23 contiguous nucleotides of the target gene and which, when it is transcribed, generates RNA comprising a first strand having a sequence substantially complementary to at least 19 preferably at least 20, more preferably at least 21, for example 22 or 23 contiguous nucleotides of the target gene and a second strand having a sequence at substantially complementary to the first strand or parts thereof, and a terminator regulatory sequence.

It is preferred that first strand and the second strand are capable of hybridizing to form dsRNA at least partially.

In another embodiment the vector construct comprises a promoter that is functional in the plant cell, operably linked to a target nucleic acid which, when it is transcribed, generates RNA comprising a first strand having a sequence substantially complementary or identical to at least 19 preferably at least 20, more preferably at least 21, for example 22 or 23 contiguous nucleotides of the target gene, and a terminator regulatory sequence.

It is preferred that the transcript of the first strand and at least a part of the transcript of the target gene are capable of hybridizing to form dsRNA at least partially.

In one embodiment the vector construct comprises a target nucleic acid comprising 19 to 500 nucleotides. Further variants of the target nucleic acid are defined in the section referring to the method for producing a plant.

With respect to a vector construct and/or the recombinant nucleic acid, the term “operatively linked” is intended to mean that the target nucleic acid is linked to the regulatory sequence, including promoters, terminators, enhancers and/or other expression control elements (e.g., polyadenylation signals), in a manner which allows for expression of the target nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of dsRNA desired, and the like. The vector constructs of the invention can be introduced into plant host cells to thereby produce ssRNA, dsRNA, siRNA and/or miRNA in order to prevent and/or reduce expression of the respective target gene and thereby increase resistance to fungal pathogens of the family Phacosporaceae, for example soybean rust.

In one embodiment, the vector construct comprises a promoter operatively linked to a target nucleotide that is a template for one or both strands of the ssRNA- or dsRNA molecules at least substantial complementary to 19 contiguous nucleotides of the target gene.

In one embodiment, the nucleic acid molecule further comprises two promoters flanking either end of the nucleic acid molecule, wherein the promoters drive expression of each individual DNA strand, thereby generating two complementary RNAs that hybridize and form the dsRNA. In alternative embodiments, the nucleotide sequence is transcribed into both strands of the dsRNA on one transcription unit, wherein the sense strand is transcribed from the 5' end of the transcription unit and the antisense strand is transcribed from the 3' end, wherein the two strands are separated by about 3 to about 500 base pairs, and wherein after transcription, the RNA transcript folds on itself to form a hairpin.

In another embodiment, the vector contains a bidirectional promoter, driving expression of two nucleic acid molecules, whereby one nucleic acid molecule codes for the sequence substantially identical to a portion of a target gene of the invention and the other nucleic acid molecule codes for a second sequence being substantially complementary to the first strand and capable of forming a dsRNA, when both sequences are transcribed. A bidirectional promoter is a promoter capable of mediating expression in two directions.

In another embodiment, the vector contains two promoters, one mediating transcription of the sequence substantially identical to a portion of a target gene of the invention and another promoter mediating transcription of a second sequence being substantially complementary to the first strand and capable of forming a dsRNA, when both sequences are transcribed. The second promoter might be a different promoter.

A different promoter means a promoter having a different activity in regard to cell or tissue specificity, or showing expression on different inducers for example, pathogens, abiotic stress or chemicals.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like. Promoters that express the dsRNA in a cell that is contacted by fungus are preferred. Alternatively, the promoter may drive expression of the dsRNA in a plant tissue remote from the site of contact with the fungus, and the dsRNA may then be transported by the plant to a cell that is contacted by the fungus, in particular cells of, or close by fungal infected sites.

Preferably, the expression vector of the invention comprises a constitutive promoter, root-specific promoter, a pathogen inducible promoter, or a fungal-inducible promoter. A promoter is inducible, if its activity, measured on the amount of RNA produced under control of the promoter, is at least 30%, 40%, 50% preferably at least 60%, 70%, 80%, 90% more preferred at least 100%, 200%, 300% higher in its induced state, than in its un-induced state. A promoter is cell-, tissue- or organ-specific, if its activity, measured on the amount of RNA produced under control of the promoter, is at least 30%, 40%, 50% preferably at least 60%, 70%, 80%, 90% more preferred at least 100%, 200%, 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene)

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermisspezific promotors may be selected from the group consisting of:

WIRS (=GstA1); acc. X56012; Dudler & Schweizer,
GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998),
GLP2a, acc. AJ237942, Schweizer P., Christoffel A. and Dudler R., Plant J. 20, 541 (1999); Prx7, acc. AJ003141, Kristensen B. K., Ammitzböll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);
Chitinase ChtC2-Promotor from potato (Ancillo et al., Planta. 217(4), 566, (2003));
AtProT3 Promotor (Grallath et al., Plant Physiology. 137(1), 117 (2005));
SHN-Promotors from *Arabidopsis* (AP2/EREBP transcription factors involved in cutin and wax production) (Aarón et al., Plant Cell. 16(9), 2463 (2004)); and/or
GSTA1 from wheat (Dudler et al., WP2005306368 and Altpeter et al., Plant Molecular Biology. 57(2), 271 (2005)).

Mesophyllspezific promotors may be selected from the group consisting of:

PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);
OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001); and/or
HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of

PcUbi promoter from parsley (WO 03/102198)
CaMV 35S promoter: Cauliflower Mosaic Virus 35S promoter (Benfey et al. 1989 EMBO J. 8(8): 2195-2202),
STPT promoter: *Arabidopsis thaliana* Short Triose phosphat translocator promoter (Accession NM_123979)
Act1 promoter:—*Oryza sativa* actin 1 gene promoter (McElroy et al. 1990 PLANT CELL 2(2) 163-171 a) and/or
EF1A2 promoter: *Glycine max* translation elongation factor EF1 alpha (US 20090133159).

The skilled person is aware, that the methods of the invention for upregulation of Pti4, Pti5, ERF1 and/or ERF2 as defined above and downregulation of CTR1, EBF1 and/or an EBF2 as defined above to increase Phacosporacea, for example soybean rust resistance in a plant by priming the ethylene signaling pathway may be combined and applied to one plant at a time. This means that the vector or plant or plant part of the invention may comprise one or more constructs for overexpression of at least one of Pti4, Pti5, ERF1 and/or ERF2 and at the same time one or more constructs for downregulation of at least one of CTR1, EBF1 and/or an EBF2.

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

According to the present invention the target nucleic acid is capable to reduce the protein quantity or function of any of the proteins of the invention in plant cells. In preferred embodiments, the decrease in the protein quantity or function of the target protein takes place in a constitutive or tissue-specific manner. In especially preferred embodiments, an essentially pathogen-induced decrease in the protein quantity or protein function takes place, for example by recombinant expression of the target nucleic acid under the control of a fungal-inducible promoter. In particular, the expression of the target nucleic acid takes place on fungal infected sites, where, however, preferably the expression of the target nucleic acid sequence remains essentially unchanged in tissues not infected by fungus. In preferred embodiments, the protein amount of a target protein in the plant is reduced by at least 10%, at least 20%, at least 30%, at least 40%, at least 50%, at least 60%, at least 70%, at least 80%, at least 90%, or at least 95% or more in comparison to a wild type plant that is not transformed with the target nucleic acid. Preferably the wild type plant is a plant of a similar, more preferably identical genotype as the plant transformed with the target nucleic acid.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

The transgenic plant cells may be transformed with one of the above described vector constructs. Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846, 797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of Agrobacterium (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). Agrobacterium based transformation techniques (especially for dicotyledonous plants) are well known in the art. The Agrobacterium strain (e.g., Agrobacterium tumefaciens or Agrobacterium rhizogenes) comprises a plasmid (Ti or Ri plasmid) and a T-DNA element which is transferred to the plant following infection with Agrobacterium. The T-DNA (transferred DNA) is integrated into the genome of the plant cell. The T-DNA may be localized on the Ri- or Tiplasmid or is separately comprised in a so-called binary vector. Methods for the Agrobacterium mediated transformation are described, for example, in Horsch R B et al. (1985) Science 225:1229. The Agrobacterium-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S.D. Kung and R. Wu, Academic Press, 1993, pp. 15-38; Jenes B et al. Techniques for Gene Transfer, Transgenic Plants, Vol. 1, Engineering and Utilization, edited by S.D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S.D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Harvestable parts of the transgenic plant according to the present invention are part of the invention. The harvestable parts may be seeds, roots, leaves and/or flowers comprising the SMT1-gene, the complementary SMT1-gene and/or a part thereof. Preferred parts of soy plants are soy beans comprising the transgenic SMT1-gene.

Products derived from transgenic plant according to the present invention, parts thereof or harvestable parts thereof are part of the invention. A preferred product is soybean meal or soybean oil.

The present invention also includes methods for the production of a product comprising a) growing the plants of the invention and b) producing said product from or by the plants of the invention and/or parts thereof, e.g. seeds, of these plants. In a further embodiment the method comprises the steps a) growing the plants of the invention, b) removing the harvestable parts as defined above from the plants and c) producing said product from or by the harvestable parts of the invention.

In one embodiment the method for the production of a product comprises a) growing the plants of the invention or obtainable by the methods of invention and
b) producing said product from or by the plants of the invention and/or parts, e.g. seeds, of these plants.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one ore more agricultural products to a large extent.

FIGURES

FIG. 1 shows the schematic illustration of the ET signaling pathway (taken from Adie et al. J Plant Growth Regul 2007 26:160ff, DOI 10.1007/s00344-007-0012-6). Binding of ET leads to inactivation of its receptor and in turn to the deactivation of the Raf-like kinase CTR1. This allows EIN2 to activate the Ein3 family of transcription factors. On the other hand Ein3 is regulated by EBF1 and EBF2, leading to the degradation of EIN3. Activated Ein3 up-regulates the expression of ERF1 (and his homologous/orthologous genes). ERF1 (and other ERF-like transcription factors) activate the expression of ethylene regulated defense genes (e.g. PR proteins etc.).

Figure 2:
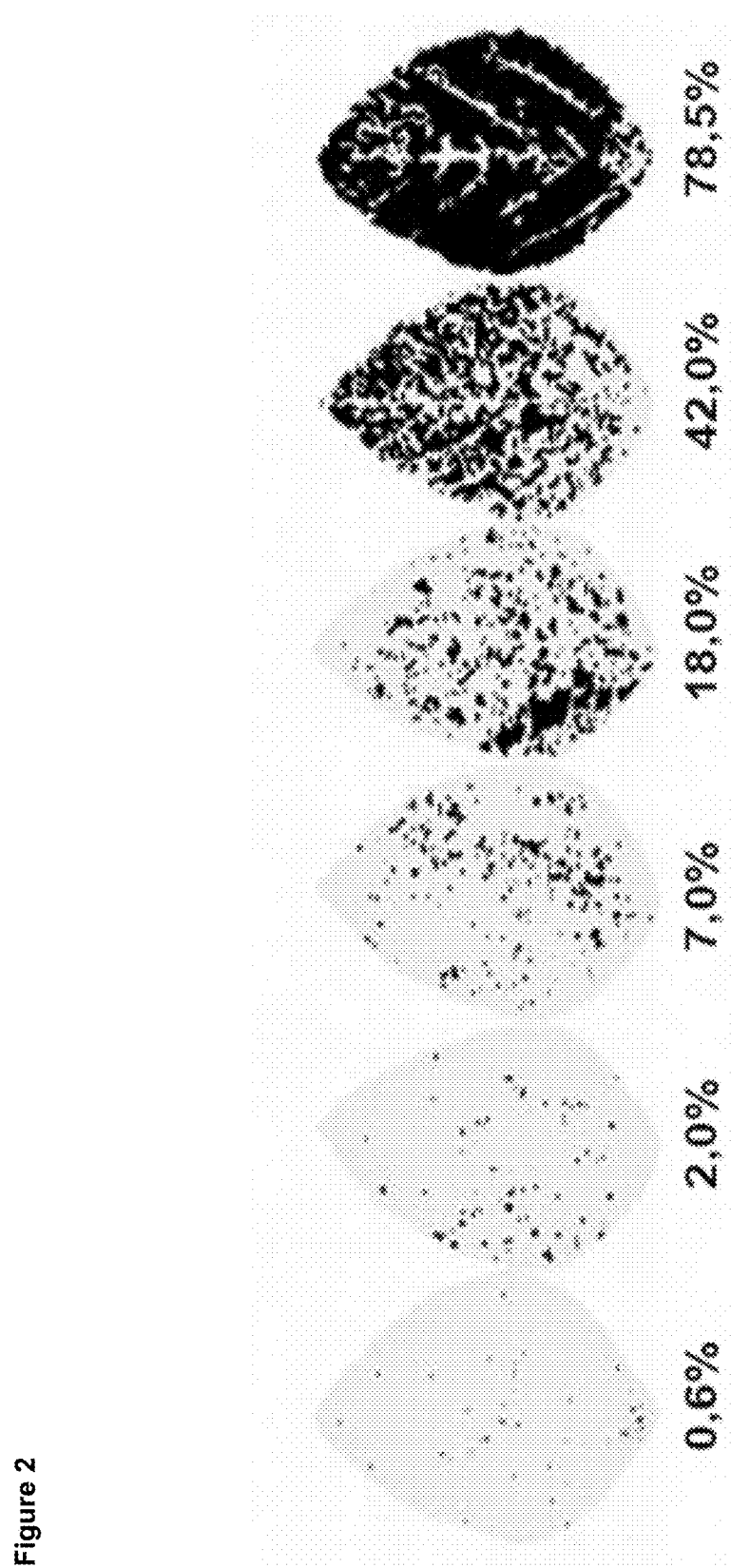
Figure 5:
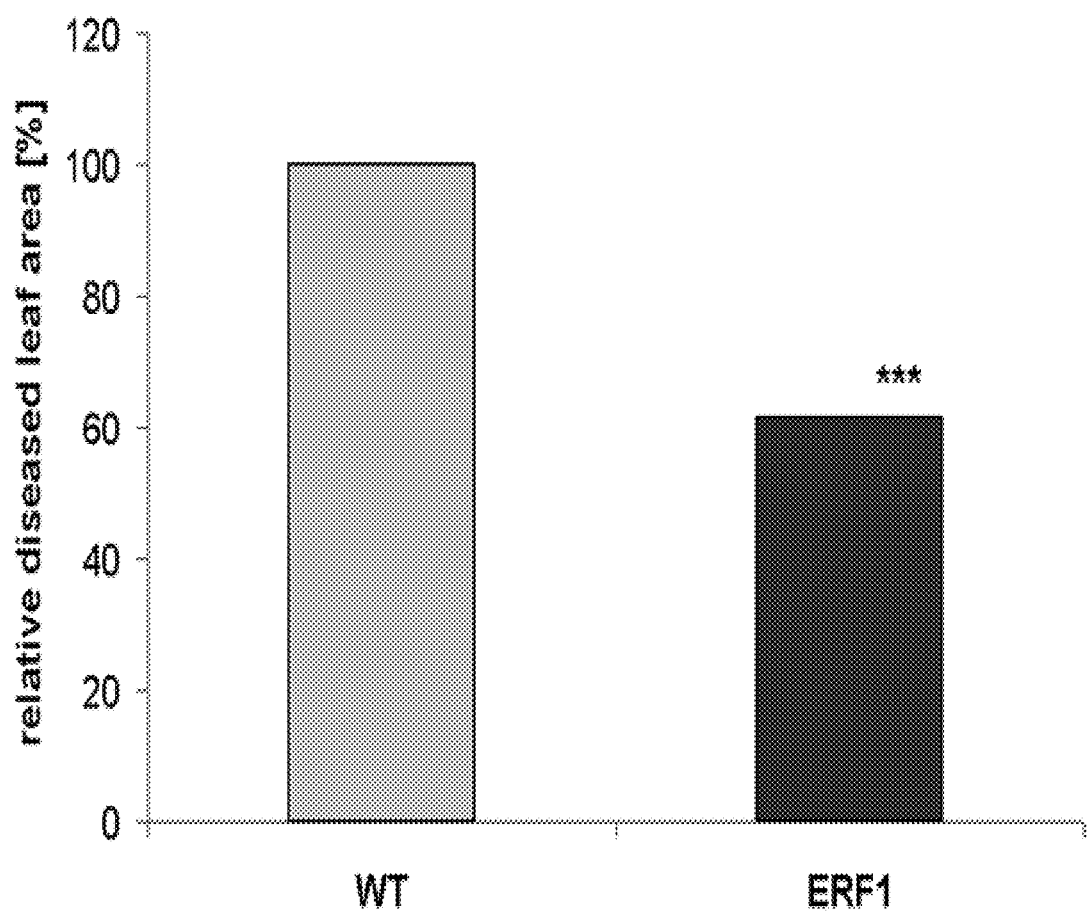
Figure 8:
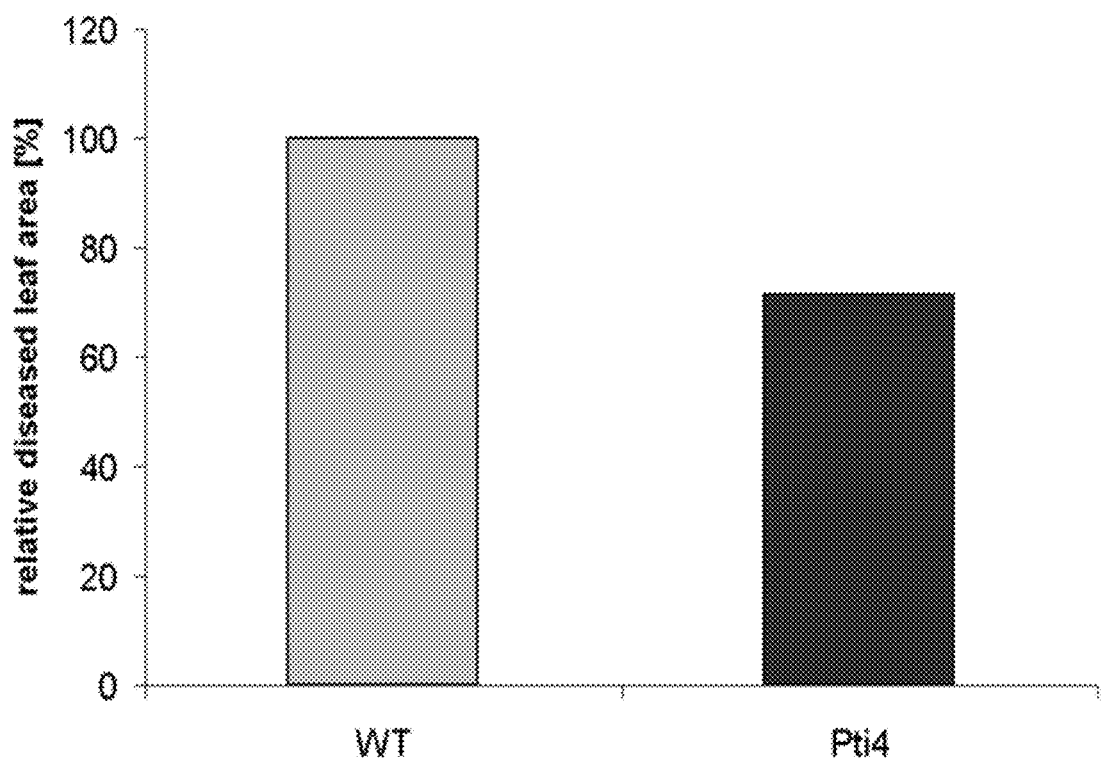
Figure 11:
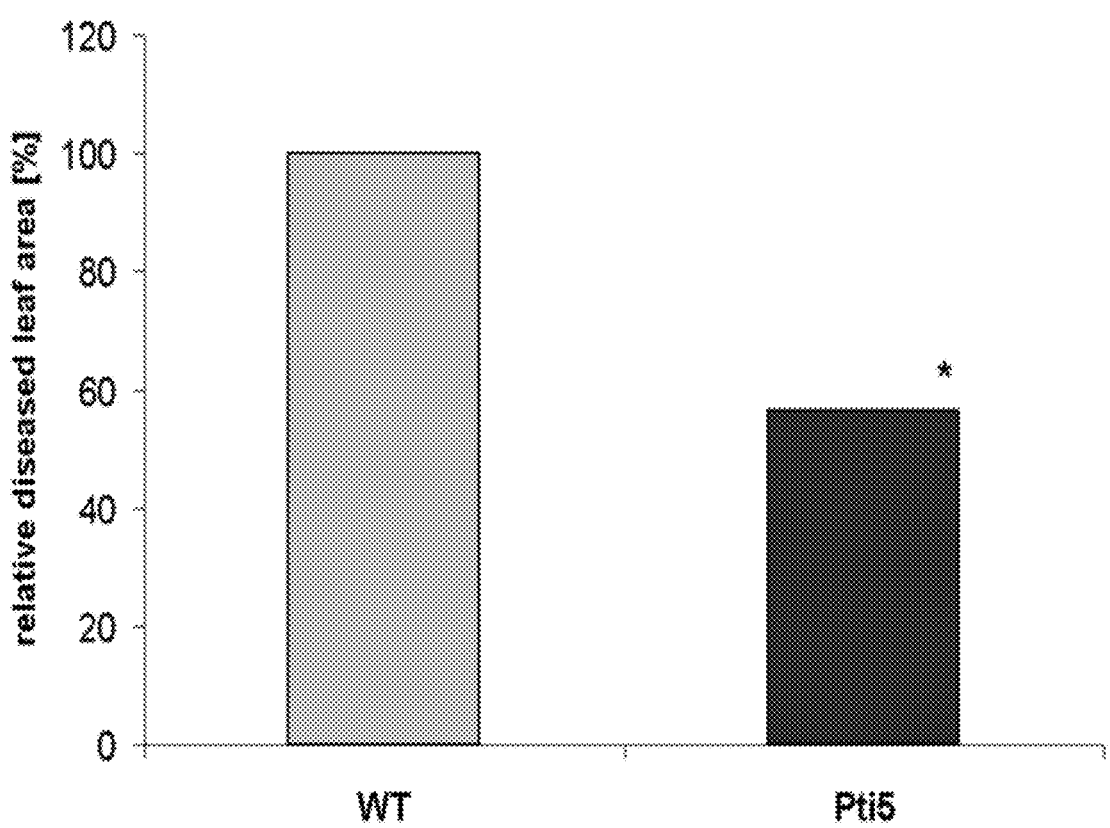

FIG. 2 shows the scoring system used to determine the level of diseased leaf area of wildtype and transgenic soy plants against the rust fungus *P. pachyrhizi.*

Figure 14:
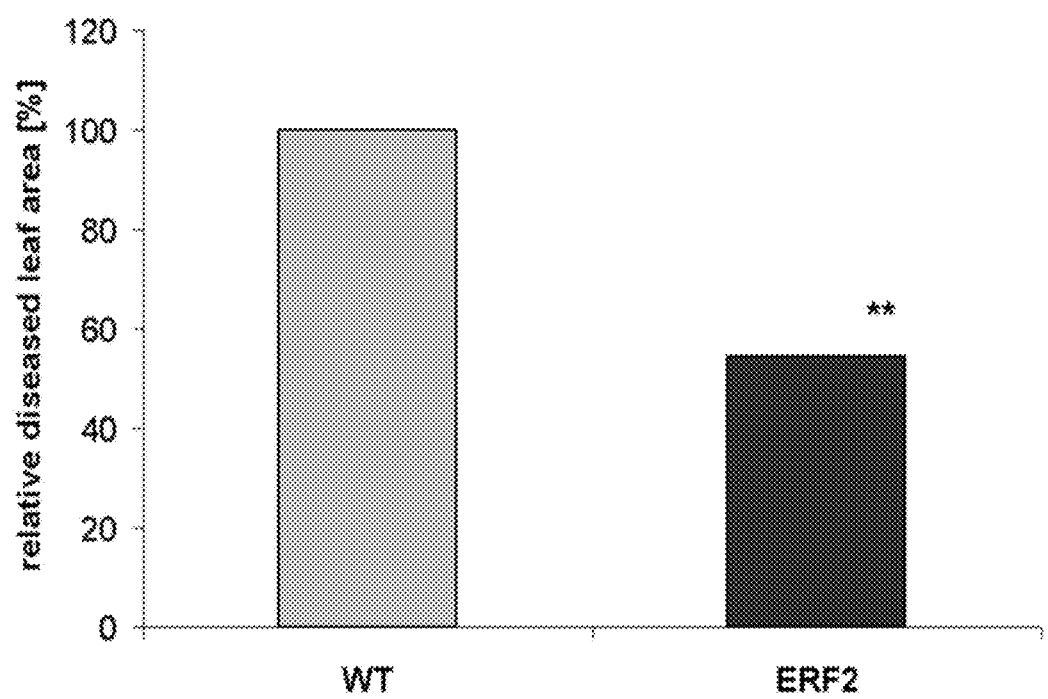

FIG. 3 shows the full-length-sequence of the ERF-1-gene from *Arabidopsis thaliana* having SEQ-ID-No. 1.

FIG. 4 shows the sequence of the ERF-1-protein (SEQ-ID-2).

FIG. 5 shows the result of the scoring of 31 transgenic soy plants expressing the ERF-1 overexpression vector construct. T0 soybean plants expressing ERF-1 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 31 soybean T0 plants expressing ERF-1 (expression checked by RT-PCR) were evaluated in parallel to non-transgenic control plants. The median of the diseased leaf area is shown in FIG. 5. Overexpression of ERF-1 significantly ($p<0.001$) reduces the diseased leaf area in comparison to non-transgenic control plants.

FIG. 6 shows the full-length-sequence of the Pti-4-gene from *Solanum lycopersicum* having SEQ-ID-No. 3.

FIG. 7 shows the sequence of the Pti-4-protein (SEQ-ID-4).

FIG. 8 shows the result of the scoring of 33 transgenic soy plants expressing the Pti-4 overexpression vector construct. T0 soybean plants expressing Pti-4 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 33 soybean T0 plants expressing Pti-4 (expression checked by RT-PCR) were evaluated in parallel to non-transgenic control plants. The median of the diseased leaf area is shown in FIG. 8. Overexpression of Pti-4 reduces the diseased leaf area in comparison to non-transgenic control plants.

FIG. 9 shows the full-length-sequence of the Pti-5-gene from *Solanum lycopersicum* having SEQ-ID-No. 5.

FIG. 10 shows the sequence of the Pti-5-protein (SEQ-ID-6).

FIG. 11 shows the result of the scoring of 34 transgenic soy plants expressing the Pti-5 overexpression vector construct. T0 soybean plants expressing Pti-5 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 34 soybean T0 plants expressing Pti-5 (expression checked by RT-PCR) were evaluated in parallel to non-transgenic control plants. The median of the diseased leaf area is shown in FIG. 11. Overexpression of Pti-5 significantly reduces ($p<0.05$) the diseased leaf area in comparison to non-transgenic control plants.

FIG. 12 shows the full-length-sequence of the ERF-2-gene from *Arabidopsis thaliana* having SEQ-ID-No. 7.

FIG. 13 shows the sequence of the ERF-2-protein (SEQ-ID-8).

FIG. 14 shows the result of the scoring of 29 transgenic soy plants expressing the ERF-2 overexpression vector construct. T0 soybean plants expressing ERF-2 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 29 soybean T0 plants expressing ERF-2 (expression checked by RT-PCR) were evaluated in parallel to non-transgenic control plants. The median of the diseased leaf area is shown in FIG. 14. Overexpression of ERF-2 significantly ($p<0.01$) reduces the diseased leaf area in comparison to non-transgenic control plants.

The full-length-sequence of the CTR-1-gene from *Arabidopsis thaliana* is defined by SEQ-ID-No. 9.

The sequence of the CTR-1-protein is defined by SEQ-ID-10.

The full-length-sequence of the EBF-1-gene from *Arabidopsis thaliana* is defined by SEQ-ID-No. 11.

The sequence of the EBF-1-protein is defined by SEQ-ID-12.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The cDNAs of all genes mentioned in this application were generated by DNA synthesis (Geneart, Regensburg, Germany).

The ERF1 cDNA was synthesized in a way that a EcoRV restriction site is located in front of the start-ATG and a SpeI restriction site downstream of the stop-codon. The synthesized cDNA were digested using the restriction enzymes EcoRV and SpeI (NEB Biolabs) and ligated in a EcoRV/SpeI digested Gateway pENTRY vector (Invitrogen, Life Technologies, Carlsbad, Calif., USA) in a way that the full-length fragment is located in sense direction between the parsley ubiquitine promoter (PcUbi) and a *Agrobacterium* tOCS terminator.

To obtain the binary plant transformation vector, a triple LR reaction (Gateway system, (Invitrogen, Life Technologies, Carlsbad, Calif., USA) was performed according to manufacturers protocol by using a pENTRY-A vector containing a parsley ubiquitine promoter, the above described pENTRY-B vector containing the cDNA and a pENTRY-C vector containing a t-StCatpA terminator. As target a binary pDEST vector was used which is composed of: (1) a Kanamycin resistance cassette for bacterial selection (2) a pVS1 origin for replication in Agrobacteria (3) a pBR322 origin of replication for stable maintenance in *E. coli* and (4) between the right and left border an AHAS selection under control of a PcUbi-promoter (FIG. 4). The recombination reaction was transformed into *E. coli* (DH5alpha), mini-prepped and screened by specific restriction digestions. A positive clone from the vector construct was sequenced and submitted soy transformation.

The Pti4, Pti5, CTR1 cDNA were synthesized in a way that an attB1-recombination site (Gateway system, (Invitrogen, Life Technologies, Carlsbad, Calif., USA) is located in front of the start-ATG and a attB2 recombination site is located directly downstream of the stop-codon. The synthesized cDNAs were transferred to a pENTRY-B vector by using the BP reaction (Gateway system, (Invitrogen, Life Technologies, Carlsbad, Calif., USA) according to the protocol provided by the supplier. To obtain the binary plant transformation vector, a triple LR reaction (Gateway system, (Invitrogen, Life Technologies, Carlsbad, Calif., USA) was performed according to manufacturers protocol by using a pENTRY-A vector containing a parsley ubiquitine promoter, the cDNAs in a pENTRY-B vector and a pENTRY-C vector containing a t-Nos terminator. As target a binary pDEST vector was used which is composed of: (1) a Kanamycin resistance cassette for bacterial selection (2) a pVS1 origin for replication in Agrobacteria (3) a pBR322 origin of replication for stable maintenance in *E. coli* and (4) between the right and left border an AHAS selection under control of a pcUbi-promoter (FIG. 4). The recombination reaction was transformed into *E. coli* (DH5alpha), mini-prepped and screened by specific restriction digestions. A positive clone from each vector construct was sequenced and submitted soy transformation.

The EFB1 and ERF2 cDNA were synthesized in a way that an EcoRV restriction site is located in front of the start-ATG and a SpeI restriction site downstream of the stop-codon. The synthesized cDNAs were digested using the restriction enzymes EcoRV and SpeI (NEB Biolabs) and ligated in a EcoRV/SpeI digested Gateway pENTRY vector (Invitrogen, Life Technologies, Carlsbad, Calif., USA) in a way that the full-length fragment is located in sense direction between the parsley ubiquitine promoter (PcUbi) and a *Agrobacterium* tOCS terminator. To obtain the binary plant transformation vector, a triple LR reaction (Gateway system, (Invitrogen, Life Technologies, Carlsbad, Calif., USA) was performed according to manufacturers protocol by using an empty pENTRY-A vector containing no sequence between the recombination sites, the above described pENTRY-B vector containing the cDNAs, and an empty pENTRY-C vector. As target a binary pDEST vector was used which is composed of: (1) a Kanamycin resistance cassette for bacterial selection (2) a pVS1 origin for replication in Agrobacteria (3) a pBR322 origin of replication for stable maintenance in *E. coli* and (4) between the right and left border an AHAS selection under control of a pcUbi-promoter (FIG. 4). The recombination reaction was transformed into *E. coli* (DH5alpha), mini-prepped and screened by specific restriction digestions. A positive clone from each vector construct was sequenced and submitted soy transformation.

Example 3 Soy Transformation

The expression vector constructs (see example 2) were transformed into soy.

3.1 Sterilization and Germination of Soy Seeds

Virtually any seed of any soy variety can be employed in the method of the invention. A variety of soycultivar (including Jack, Williams 82, and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 pEinstein/m2s) at 25 degree C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings (Method A, see example 3.3. and 3.3.2) or leaf explants (Method B, see example 3.3.3), the seedlings were then ready for transformation.

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract. 10 g Bacto Peptone. 5 g NaCl. Adjust pH to 7.0, and bring final volume to 1 liter with H2O, for YEP agar plates add 20 g Agar, autoclave) and incubating at 25.degree C. until colonies appeared (about 2 days). Depending on the selectable marker genes present on the Ti or Ri plasmid, the binary vector, and the bacterial chromosomes, different selection compounds were be used for *A. tumefaciens* and *rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25.degree. C.) until an OD.sub.600 between 0.8-1.0 is reached (approximately 2 d). Working glycerol stocks (15%) for transformation are prepared and one-ml of *Agrobacterium* stock aliquoted into 1.5 ml Eppendorf tubes then stored at −80.degree C.

The day before explant inoculation, 200 ml of YEP were inoculated with 5 .mu.l to 3 ml of working *Agrobacterium* stock in a 500 ml Erlenmeyer flask. The flask was shaked overnight at 25.degree. C. until the OD.sub.600 was between 0.8 and 1.0. Before preparing the soyexplants, the Agrobacteria were pelleted by centrifugation for 10 min at 5,500.times.g at 20.degree. C. The pellet was resuspended in liquid CCM to the desired density (OD.sub.600 0.5-0.8) and placed at room temperature at least 30 min before use.

3.3—Explant Preparation and Co-Cultivation (Inoculation)

3.3.1 Method A: Explant Preparation on the Day of Transformation

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15.times.100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soyacv L00106CN, 93-41131 and Jack were germinated in ⅒ MS salts or a similar composition medium with or without cytokinins for 4.about.8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the construct of the invention and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for enhancing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong expression of the construct of the invention were recovered.

Soyplants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any pre-formed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soyexplants. Wrap five plates with Parafilm™ "M" (American National Can, Chicago, Ill., USA) and incubate for three to five days in the dark or light at 25.degree. C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soyexplants. Plates were wrapped with Parafilm™ "M" (American National Can, Chicago, Ill., USA) and incubated for two to three days in the dark at 25.degree. C.

3.4—Shoot Induction

After 3 to 5 days co-cultivation in the dark at 25.degree. C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol.—Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25.degree. C. under 18 h light/6 h dark cycle at 70-100.mu.E/m.sup.2s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium medium (shoot elongation medium, see Olhoft et al 2007 A novel *Agrobacterium rhizogenes*-mediated transformation method of soy using primary-node explants from seedlings. In Vitro Cell. Dev. Biol.—Plant (2007) 43:536-549) that stimulates shoot elongation of the shoot primordia. This medium may or may not contain a selection compound.

After every 2 to 3 weeks, the explants were transfer to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

Transient expression of the construct of the invention after 5 days of co-cultivation with *Agrobacterium tumefaciens* was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the construct of the invention was stable after 14 days on SIM, implying integration of the T-DNA into the soy genome. In addition, preliminary experiments resulted in the formation of positive shoots expressing the construct of the invention forming after 3 weeks on SIM.

For Method C, the average regeneration time of a soyplantlet using the propagated axillary meristem protocol was 14 weeks from explant inoculation. Therefore, this method has a quick regeneration time that leads to fertile, healthy soyplants.

Example 4: Pathogen Assay 4.1. Recovery of Clones 2-3 clones per T0 event were potted into small 6 cm pots. For recovery the clones were kept for 12-18 days in the Phytochamber (16 h-day-und 8 h-night-Rhythm at a temperature of 16° bis 22° C. und a humidity of 75% were grown).

4.2 Inoculation

The rust fungus is a wild isolate from Brazil. The plants were inoculated with *P. pachyrhizi*.

In order to obtain appropriate spore material for the inoculation, soyleaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×105 spores/ml. For the microscopy, a density of >5×105 spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5 Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1,5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae coul be recognized beneath the fungal appressorium by a green/yellow staining. The hypersensitive reaction (HR) was characterized by a whole cell fluorescence.

Example 6 Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account. (for scheme see FIG. 2)

6.1 Overexpression of ERF-1

T0 soybean plants expressing ERF-1 protein were inoculated with spores of *Phakopsora pachyrhizi*. The macroscopic disease symptoms of soy against *P. pachyrhizi* of 31 T0 soybean plants were scored 14 days after inoculation.

The average of the percentage of the leaf area showing fungal colonies or strong yellowing/browning on all leaves was considered as diseased leaf area. At all 31 soybean T0 plants expressing ERF-1 (expression checked by RT-PCR) were evaluated in parallel to non-transgenic control plants. Clones from non-transgenic soy plants were used as control. The median of the diseased leaf area is shown in FIG. 5 for plants expressing recombinant ERF-1 compared with wild-type plants. Overexpression of ERF-1 reduces the diseased leaf area in comparison to non-transgenic control plants by 40%. This data clearly indicate that the in planta expression of the ERF-1 expression vector construct lead to a lower disease scoring of transgenic plants compared to non-transgenic controls. So, the expression of ERF-1 and therefore the priming of the ethylene signaling pathway in soy enhances the resistance of soy against soybean rust.

6.2 Overexpression of Pti-4

T0 soybean plants expressing Pti-4 protein were inoculated with spores of *Phakopsora pachyrhizi*. The macroscopic disease symptoms of soy against *P. pachyrhizi* of 33 T0 soybean plants were scored 14 days after inoculation.

The average of the percentage of the leaf area showing fungal colonies or strong yellowing/browning on all leaves was considered as diseased leaf area. At all 31 soybean T0 plants expressing Pti-4 (expression checked by RT-PCR) were evaluated in parallel to non-transgenic control plants. Clones from non-transgenic soy plants were used as control. The median of the diseased leaf area is shown in FIG. 8 for plants expressing recombinant Pti-4 compared with wild-type plants. Overexpression of Pti-4 reduces the diseased leaf area in comparison to non-transgenic control plants by 28%. This data clearly indicate that the in planta expression of the Pti-4 expression vector construct lead to a lower disease scoring of transgenic plants compared to non-transgenic controls. So, the expression of Pti-4 and therefore the priming of the ethylene signaling pathway in soy enhances the resistance of soy against soybean rust.

6.3 Overexpression of Pti-5

T0 soybean plants expressing Pti-5 protein were inoculated with spores of *Phakopsora* pachyrhizi. The macroscopic disease symptoms of soy against *P. pachyrhizi* of 34 T0 soybean plants were scored 14 days after inoculation.

The average of the percentage of the leaf area showing fungal colonies or strong yellowing/browning on all leaves was considered as diseased leaf area. At all 34 soybean T0 plants expressing Pti-5 (expression checked by RT-PCR) were evaluated in parallel to non-transgenic control plants. Clones from non-transgenic soy plants were used as control. The median of the diseased leaf area is shown in FIG. 11 for plants expressing recombinant Pti-5 compared with wildtype plants. Overexpression of Pti-5 reduces the diseased leaf area in comparison to non-transgenic control plants by 43%. This data clearly indicate that the in planta expression of the Pti-4 expression vector construct lead to a lower disease scoring of transgenic plants compared to non-transgenic controls. So, the expression of Pti-4 and therefore the priming of the ethylene signaling pathway in soy enhance the resistance of soy against soybean rust.

6.4 Overexpression of ERF-2

T0 soybean plants expressing ERF-2 protein were inoculated with spores of Phakopsora pachyrhizi. The macroscopic disease symptoms of soy against *P. pachyrhizi* of 29 T0 soybean plants were scored 14 days after inoculation.

The average of the percentage of the leaf area showing fungal colonies or strong yellowing/browning on all leaves was considered as diseased leaf area. At all 29 soybean T0 plants expressing ERF-2 (expression checked by RT-PCR) were evaluated in parallel to non-transgenic control plants. Clones from non-transgenic soy plants were used as control. The median of the diseased leaf area is shown in FIG. 14 for plants expressing recombinant ERF-2 compared with wild-type plants. Overexpression of ERF-2 reduces the diseased leaf area in comparison to non-transgenic control plants by 45%. This data clearly indicate that the in planta expression of the ERF-2 expression vector construct lead to a lower disease scoring of transgenic plants compared to non-transgenic controls. So, the expression of ERF-2 and therefore the priming of the ethylene signaling pathway in soy enhance the resistance of soy against soybean rust.

6.5 Overexpression of ET-Pathway Inhibiting Enzymes CTR-1 and EBF-1

T0 soybean plants expressing the ET-pathway inhibiting proteins CTR-1 and EBF-1 were inoculated with spores of *Phakopsora pachyrhizi*. The macroscopic disease symptoms of soy against *P. pachyrhizi* of 27 respectively 28 T0 soybean plants were scored 14 days after inoculation. The average of the percentage of the leaf area showing fungal colonies or strong yellowing/browning on all leaves was considered as diseased leaf area. At all 27 CTR-1 overexpressing soybean T0 plants and 28 EBF-1 overexpressing soybean T0 were evaluated in parallel to non-transgenic control plants. Clones from non-transgenic soy plants were used as control. Overexpression of the ethylene signaling pathway inhibiting proteins CTR-1 and EBF-1 enhances the diseased leaf area in comparison to non-transgenic control plants. This data clearly indicate that the in planta inhibition of the ET pathway lead to a higher disease scoring of transgenic plants compared to non-transgenic controls. So, the inhibition of the ethylene signaling pathway in soy reduces the resistance of soy against soybean rust.

6.6 Priming of the Ethylene Signaling Pathway by Inhibiting Enzymes CTR-1 by RNAi Four sets of transgenic T0 soybean plants are produced expressing RNAi constructs targeting GmCTR1a (SEQ ID 13), GmCTR1b (SEQ ID 15) or GmCTR1c (SEQ ID 17) individually or all three homologous genes respectively. The RNAi constructs are synthesized and subsequently cloned into transformation vectors under the control of constitutive, pathogen inducible, leaf specific and/or epidermis specific promoters. The RNAi constructs are SEQ ID 25, targeting GmCTR1a, SEQ ID 26 targeting GmCTR1b, SEQ ID 27 targeting GmCTR1c and SEQ ID28 targeting GmCTR1 a, b and c.

The transgenic plants are analysed by RTqPCR for down-regulation of the respective gene/s. Plants showing strong repression of CTR1 expression are inoculated with spores of *Phakopsora pachyrhizi*. The macroscopic disease symptoms of soy against *P. pachyrhizi* of up to 30 T0 soybean plants per construct are scored 14 days after inoculation.

The average of the percentage of the leaf area showing fungal colonies or strong yellowing/browning on all leaves is considered as diseased leaf area. All soybean T0 plants exhibiting repression of CTR1a, b or c or CTR1 a and b and c are evaluated in parallel to non-transgenic control plants. Clones from non-transgenic soy plants are used as control. Repression of CTR1 expression reduces the diseased leaf area in comparison to non-transgenic control plants significantly. The repression of CTR1 expression and therefore the priming of the ethylene signaling pathway in soy enhance the resistance of soy against soybean rust.

6.7 Priming of the Ethylene Signaling Pathway by Inhibiting Enzymes CTR-1 by microRNA Expression Transgenic T0 soybean plants are produced expressing a recombinant microRNA precursor comprising a microRNA targeting all three homologous GmCTR1a (SEQ ID 13), GmCTR1b (SEQ ID 15) and GmCTR1c (SEQ ID 17) genes. The microRNA precursor is synthesized and subsequently cloned into transformation vectors under the control of constitutive, pathogen inducible, leaf specific and/or epidermis specific promoters. The microRNA precursor is shown in SEQ ID 33.

The transgenic plants are analyzed by RTqPCR for down-regulation of the CTR1 homologues. Plants showing strong repression of CTR1 expression are inoculated with spores of *Phakopsora pachyrhizi*. The macroscopic disease symptoms of soy against *P. pachyrhizi* of up to 30 T0 soybean plants are scored 14 days after inoculation.

The average of the percentage of the leaf area showing fungal colonies or strong yellowing/browning on all leaves is considered as diseased leaf area. All soybean T0 plants exhibiting repression of CTR1 are evaluated in parallel to non-transgenic control plants. Clones from non-transgenic soy plants are used as control. Repression of CTR1 expression reduces the diseased leaf area in comparison to non-transgenic control plants significantly. The repression of CTR1 expression and therefore the priming of the ethylene signaling pathway in soy enhance the resistance of soy against soybean rust.

6.8 Priming of the Ethylene Signaling Pathway by Inhibiting Enzymes EBF-1 by RNAi Three sets of transgenic T0 soybean plants are produced expressing RNAi constructs targeting GmEBF1a (SEQ ID 19), GmEBF1b (SEQ ID 21) or GmEBF1c (SEQ ID 23) individually. The RNAi constructs are synthesized and subsequently cloned into transformation vectors under the control of constitutive, pathogen inducible, leaf specific and/or epidermis specific promoters. The RNAi constructs are SEQ ID 29, targeting GmEBF1a, SEQ ID 30 targeting GmEBF1b, SEQ ID 31 targeting.

The transgenic plants are analyzed by RTqPCR for down-regulation of the respective gene. Plants showing strong repression of expression of the respective GmEBF1 gene are inoculated with spores of *Phakopsora pachyrhizi*. The macroscopic disease symptoms of soy against *P. pachyrhizi* of up to 30 T0 soybean plants per construct are scored 14 days after inoculation. The average of the percentage of the leaf area showing fungal colonies or strong yellowing/browning on all leaves is considered as diseased leaf area. All soybean T0 plants exhibiting repression of EBF1a, b or c respectively are evaluated in parallel to non-transgenic control plants. Clones from non-transgenic soy plants are used as control. Repression of EBF1 expression reduces the diseased leaf area in comparison to non-transgenic control plants significantly. The repression of EBF1 expression and therefore the priming of the ethylene signaling pathway in soy enhance the resistance of soy against soybean rust.

6.9 Priming of the Ethylene Signaling Pathway by Inhibiting Enzymes EBF-1 by microRNA Expression Transgenic T0 soybean plants are produced expressing a recombinant microRNA precursor comprising a microRNA targeting all three homologous GmEBF1a (SEQ ID 19), GmEBF1b (SEQ ID 21) and GmEBF1c (SEQ ID 23) genes. The microRNA precursor is synthesized and subsequently cloned into transformation vectors under the control of constitutive, pathogen inducible, leaf specific and/or epidermis specific promoters. The microRNA precursor is shown in SEQ ID 32.

The transgenic plants are analyzed by RTqPCR for down-regulation of the EBF1 homologues. Plants showing strong repression of EBF1 expression are inoculated with spores of Phakopsora pachyrhizi. The macroscopic disease symptoms of soy against P. pachyrhizi of up to 30 T0 soybean plants are scored 14 days after inoculation.

The average of the percentage of the leaf area showing fungal colonies or strong yellowing/browning on all leaves is considered as diseased leaf area. All soybean T0 plants exhibiting repression of EBF1 are evaluated in parallel to non-transgenic control plants. Clones from non-transgenic soy plants are used as control. Repression of EBF1 expression reduces the diseased leaf area in comparison to non-transgenic control plants significantly. The repression of EBF1 expression and therefore the priming of the ethylene signaling pathway in soy enhance the resistance of soy against soybean rust.

The invention claimed is:

1. A method for controlling soybean rust in a soybean plant, said method comprising providing a transgenic soybean plant comprising an exogenous nucleic acid encoding a protein having an amino acid sequence with at least 95% identity with SEQ ID NO: 6, wherein the nucleic acid is in functional linkage with a promoter, and wherein expression of the nucleic acid leads to increased soybean rust resistance in said soybean plant as compared to a wild type soybean plant such that soybean rust is controlled in the transgenic soybean plant.

2. The method of claim 1, wherein the promoter is a constitutive, pathogen-inducible promoter, a mesophyll-specific promoter and/or an epidermis-specific promoter.

3. The method of claim 1, wherein the soybean rust that is controlled is *Phakopsora meibomiae* and/or *Phakopsora pachyrhizi*.

4. A transgenic soybean plant, transgenic soybean plant part, or transgenic soybean plant cell comprising:

an expression cassette comprising an exogenous recombinant nucleic acid coding for a protein having an amino acid sequence having at least 95% identity with SEQ ID NO: 6, wherein the recombinant nucleic acid is in functional linkage with a promoter;

wherein expression of the recombinant nucleic acid leads to increased soybean rust resistance in said transgenic soybean plant, transgenic soybean plant part, or transgenic soybean plant cell as compared to a wild type soybean plant, wild type soybean plant part, or wild type soybean plant cell.

5. The transgenic soybean plant, transgenic soybean plant part, or transgenic soybean plant of claim 4, wherein the promoter is a constitutive, a pathogen-inducible promoter, a mesophyll-specific promoter and/or an epidermis-specific promoter.

6. A method for preventing, reducing, or delaying *Phakopsora* infection in a soybean plant, the method comprising:

(i) providing a transgenic soybean plant comprising an exogenous nucleic acid encoding a protein having an amino acid sequence with at least 95% identity to SEQ ID NO:6, wherein the protein confers increased resistance against *Phakopsora* thereto in comparison to a wild type soybean plant; and (ii) growing the transgenic soybean plant in the presence of a fungal pathogen of the genus *Phakopsora*, wherein *Phakopsora* infection is prevented, reduced, or delayed in the transgenic soybean plant as compared to a wild type soybean plant.

7. The method of claim 1, wherein the exogenous nucleic acid encodes a protein having an amino acid sequence with at least 98% identity with SEQ ID NO: 6.

8. The transgenic soybean plant, transgenic soybean plant part, or transgenic soybean plant cell of claim 4, wherein the exogenous nucleic acid encodes a protein having an amino acid sequence having at least 98% identity with SEQ ID NO: 6.

9. The method of claim 6, wherein the exogenous nucleic acid encodes a protein having an amino acid sequence with at least 98% identity with SEQ ID NO: 6.

10. The method of claim 1, wherein the exogenous nucleic acid encodes a protein having an amino acid sequence with at least 99% identity with SEQ ID NO: 6.

11. The transgenic soybean plant, transgenic soybean plant part, or transgenic soybean plant cell of claim 4, wherein the exogenous nucleic acid encodes a protein having an amino acid sequence having at least 99% identity with SEQ ID NO: 6.

12. The method of claim 6, wherein the exogenous nucleic acid encodes a protein having an amino acid sequence with at least 99% identity with SEQ ID NO: 6.

13. The method of claim 1, wherein the exogenous nucleic acid encodes a protein having 100% sequence identity with SEQ ID NO: 6.

14. The transgenic soybean plant, transgenic soybean plant part, or transgenic soybean plant cell of claim 4, wherein the exogenous nucleic acid encodes a protein having 100% sequence identity with SEQ ID NO: 6.

15. The method of claim 6, wherein the exogenous nucleic acid encodes a protein having 100% sequence identity with SEQ ID NO: 6.

* * * * *

SEQUENCE LISTING

```
<160> NUMBER OF SEQ ID NOS: 33

<210> SEQ ID NO 1
<211> LENGTH: 657
<212> TYPE: DNA
<213> ORGANISM: Arabidopsis thaliana
<220> FEATURE:
<221> NAME/KEY: CDS
<222> LOCATION: (1)..(657)
<223> OTHER INFORMATION: AtERF1

<400> SEQUENCE: 1 atg gat cca ttt tta att cag tcc cca ttc tcc ggc ttc tca ccg gaa         48
Met Asp Pro Phe Leu Ile Gln Ser Pro Phe Ser Gly Phe Ser Pro Glu
1               5                   10                  15 tat tct atc gga tct tct cca gat tct ttc tca tcc tct tct tct aac         96
Tyr Ser Ile Gly Ser Ser Pro Asp Ser Phe Ser Ser Ser Ser Ser Asn
            20                  25                  30 aat tac tct ctt ccc ttc aac gag aac gac tca gag gaa atg ttt ctc        144
Asn Tyr Ser Leu Pro Phe Asn Glu Asn Asp Ser Glu Glu Met Phe Leu
        35                  40                  45 tac ggt cta atc gag cag tcc acg caa caa acc tat att gac tcg gat        192
Tyr Gly Leu Ile Glu Gln Ser Thr Gln Gln Thr Tyr Ile Asp Ser Asp
    50                  55                  60 agt caa gac ctt ccg atc aaa tcc gta agc tca aga aag tca gag aag        240
Ser Gln Asp Leu Pro Ile Lys Ser Val Ser Ser Arg Lys Ser Glu Lys
65                  70                  75                  80 tct tac aga ggc gta aga cga cgg cca tgg ggg aaa ttc gcg gcg gag        288
Ser Tyr Arg Gly Val Arg Arg Arg Pro Trp Gly Lys Phe Ala Ala Glu
                85                  90                  95 ata aga gat tcg act aga aac ggt att agg gtt tgg ctc ggg acg ttc        336
Ile Arg Asp Ser Thr Arg Asn Gly Ile Arg Val Trp Leu Gly Thr Phe
            100                 105                 110 gaa agc gcg gaa gag gcg gct tta gcc tac gat caa gct gct ttc tcg        384
Glu Ser Ala Glu Glu Ala Ala Leu Ala Tyr Asp Gln Ala Ala Phe Ser
        115                 120                 125 atg aga ggg tcc tcg gcg att ctc aat ttt tcg gcg gag aga gtt caa        432
Met Arg Gly Ser Ser Ala Ile Leu Asn Phe Ser Ala Glu Arg Val Gln
    130                 135                 140 gag tcg ctt tcg gag att aaa tat acc tac gag gat ggt tgt tct ccg        480
Glu Ser Leu Ser Glu Ile Lys Tyr Thr Tyr Glu Asp Gly Cys Ser Pro
145                 150                 155                 160 gtt gtg gcg ttg aag agg aaa cac tcg atg aga cgg aga atg acc aat        528
Val Val Ala Leu Lys Arg Lys His Ser Met Arg Arg Arg Met Thr Asn
                165                 170                 175 aag aag acg aaa gat agt gac ttt gat cac cgc tcc gtg aag tta gat        576
```

```
Lys Lys Thr Lys Asp Ser Asp Phe Asp His Arg Ser Val Lys Leu Asp
        180                 185                 190 aat gta gtt gtc ttt gag gat ttg gga gaa cag tac ctt gag gag ctt       624
Asn Val Val Val Phe Glu Asp Leu Gly Glu Gln Tyr Leu Glu Glu Leu
            195                 200                 205 ttg ggg tct tct gaa aat agt ggg act tgg tga                           657
Leu Gly Ser Ser Glu Asn Ser Gly Thr Trp
        210                 215
```

<210> SEQ ID NO 2
<211> LENGTH: 218
<212> TYPE: PRT
<213> ORGANISM: Arabidopsis thaliana

<400> SEQUENCE: 2

```
Met Asp Pro Phe Leu Ile Gln Ser Pro Phe Ser Gly Phe Ser Pro Glu
1               5                   10                  15

Tyr Ser Ile Gly Ser Ser Pro Asp Ser Phe Ser Ser Ser Ser Ser Asn
            20                  25                  30

Asn Tyr Ser Leu Pro Phe Asn Glu Asn Asp Ser Glu Glu Met Phe Leu
        35                  40                  45

Tyr Gly Leu Ile Glu Gln Ser Thr Gln Gln Thr Tyr Ile Asp Ser Asp
    50                  55                  60

Ser Gln Asp Leu Pro Ile Lys Ser Val Ser Ser Arg Lys Ser Glu Lys
65                  70                  75                  80

Ser Tyr Arg Gly Val Arg Arg Pro Trp Gly Lys Phe Ala Ala Glu
            85                  90                  95

Ile Arg Asp Ser Thr Arg Asn Gly Ile Arg Val Trp Leu Gly Thr Phe
            100                 105                 110

Glu Ser Ala Glu Glu Ala Ala Leu Ala Tyr Asp Gln Ala Ala Phe Ser
        115                 120                 125

Met Arg Gly Ser Ser Ala Ile Leu Asn Phe Ser Ala Glu Arg Val Gln
    130                 135                 140

Glu Ser Leu Ser Glu Ile Lys Tyr Thr Tyr Glu Asp Gly Cys Ser Pro
145                 150                 155                 160

Val Val Ala Leu Lys Arg Lys His Ser Met Arg Arg Met Thr Asn
            165                 170                 175

Lys Lys Thr Lys Asp Ser Asp Phe Asp His Arg Ser Val Lys Leu Asp
        180                 185                 190

Asn Val Val Val Phe Glu Asp Leu Gly Glu Gln Tyr Leu Glu Glu Leu
    195                 200                 205

Leu Gly Ser Ser Glu Asn Ser Gly Thr Trp
        210                 215
```

<210> SEQ ID NO 3
<211> LENGTH: 705
<212> TYPE: DNA
<213> ORGANISM: Lycopersicon esculentum
<220> FEATURE:
<221> NAME/KEY: CDS
<222> LOCATION: (1)..(705)
<223> OTHER INFORMATION: SlPti4

<400> SEQUENCE: 3

```
atg gat caa caa ctt cca cca act aac ttc cca gtt gac ttc cca gtt       48
Met Asp Gln Gln Leu Pro Pro Thr Asn Phe Pro Val Asp Phe Pro Val
1               5                   10                  15 tac aga aga aac tcc agc ttc tct agg ctt att cca tgc ctt act gag       96
Tyr Arg Arg Asn Ser Ser Phe Ser Arg Leu Ile Pro Cys Leu Thr Glu
```

|   |   |   |   |   |   |   |   |   |   |   |   |   |   |   |   |     |
|---|---|---|---|---|---|---|---|---|---|---|---|---|---|---|---|-----|
|   |   |   | 20 |   |   |   |   | 25 |   |   |   |   | 30 |   |   |     |
| aag | tgg | gga | gat | ctt | cca | ctt | aag | gtg | gac | gat | tct | gag | gat | atg | gtg | 144 |
| Lys | Trp | Gly | Asp | Leu | Pro | Leu | Lys | Val | Asp | Asp | Ser | Glu | Asp | Met | Val |     |
|   |   |   | 35 |   |   |   |   | 40 |   |   |   |   | 45 |   |   |     |
| atc | tac | gga | ctt | ctt | aag | gat | gct | ctt | tct | gtt | gga | tgg | tcc | cca | ttc | 192 |
| Ile | Tyr | Gly | Leu | Leu | Lys | Asp | Ala | Leu | Ser | Val | Gly | Trp | Ser | Pro | Phe |     |
|   |   |   | 50 |   |   |   |   | 55 |   |   |   |   | 60 |   |   |     |
| aac | ttc | act | gct | ggt | gaa | gtt | aag | tct | gag | cca | agg | gaa | gag | att | gaa | 240 |
| Asn | Phe | Thr | Ala | Gly | Glu | Val | Lys | Ser | Glu | Pro | Arg | Glu | Glu | Ile | Glu |     |
| 65 |   |   |   |   | 70 |   |   |   |   | 75 |   |   |   |   | 80 |     |
| tct | tct | cca | gag | ttc | tct | cca | tct | cca | gct | gaa | act | act | gct | gct | cca | 288 |
| Ser | Ser | Pro | Glu | Phe | Ser | Pro | Ser | Pro | Ala | Glu | Thr | Thr | Ala | Ala | Pro |     |
|   |   |   |   | 85 |   |   |   |   | 90 |   |   |   |   | 95 |   |     |
| gct | gct | gaa | act | cca | aag | gga | agg | cat | tat | agg | gga | gtt | aga | caa | aga | 336 |
| Ala | Ala | Glu | Thr | Pro | Lys | Gly | Arg | His | Tyr | Arg | Gly | Val | Arg | Gln | Arg |     |
|   |   |   | 100 |   |   |   |   | 105 |   |   |   |   | 110 |   |   |     |
| cct | tgg | gga | aag | ttc | gct | gct | gaa | att | aga | gat | cca | gct | aag | aac | ggt | 384 |
| Pro | Trp | Gly | Lys | Phe | Ala | Ala | Glu | Ile | Arg | Asp | Pro | Ala | Lys | Asn | Gly |     |
|   |   |   | 115 |   |   |   |   | 120 |   |   |   |   | 125 |   |   |     |
| gct | aga | gtt | tgg | ctt | gga | act | tat | gag | act | gct | gaa | gag | gct | gct | att | 432 |
| Ala | Arg | Val | Trp | Leu | Gly | Thr | Tyr | Glu | Thr | Ala | Glu | Glu | Ala | Ala | Ile |     |
|   |   |   | 130 |   |   |   |   | 135 |   |   |   |   | 140 |   |   |     |
| gct | tat | gat | aag | gcc | gct | tac | aga | atg | aga | gga | tcc | aag | gct | cat | ctt | 480 |
| Ala | Tyr | Asp | Lys | Ala | Ala | Tyr | Arg | Met | Arg | Gly | Ser | Lys | Ala | His | Leu |     |
| 145 |   |   |   |   | 150 |   |   |   |   | 155 |   |   |   |   | 160 |     |
| aac | ttc | cca | cac | agg | att | gga | ctt | aac | gaa | cca | gag | cca | gtt | aga | gtt | 528 |
| Asn | Phe | Pro | His | Arg | Ile | Gly | Leu | Asn | Glu | Pro | Glu | Pro | Val | Arg | Val |     |
|   |   |   |   | 165 |   |   |   |   | 170 |   |   |   |   | 175 |   |     |
| act | gct | aag | aga | agg | gct | tct | cca | gaa | cca | gct | tct | tct | tct | gga | aac | 576 |
| Thr | Ala | Lys | Arg | Arg | Ala | Ser | Pro | Glu | Pro | Ala | Ser | Ser | Ser | Gly | Asn |     |
|   |   |   | 180 |   |   |   |   | 185 |   |   |   |   | 190 |   |   |     |
| gga | tcc | atg | aag | aga | aga | aga | aag | gct | gtt | caa | aag | tgc | gac | ggt | gaa | 624 |
| Gly | Ser | Met | Lys | Arg | Arg | Arg | Lys | Ala | Val | Gln | Lys | Cys | Asp | Gly | Glu |     |
|   |   |   | 195 |   |   |   |   | 200 |   |   |   |   | 205 |   |   |     |
| atg | gct | tct | aga | tct | tcc | gtt | atg | caa | gtg | gga | tgc | caa | att | gag | caa | 672 |
| Met | Ala | Ser | Arg | Ser | Ser | Val | Met | Gln | Val | Gly | Cys | Gln | Ile | Glu | Gln |     |
|   |   |   | 210 |   |   |   |   | 215 |   |   |   |   | 220 |   |   |     |
| ctt | acc | ggt | gtt | cat | cag | ctt | ctc | gtg | atc | taa |   |   |   |   |   | 705 |
| Leu | Thr | Gly | Val | His | Gln | Leu | Leu | Val | Ile |   |   |   |   |   |   |     |
| 225 |   |   |   |   | 230 |   |   |   |   |   |   |   |   |   |   |     |

<210> SEQ ID NO 4
<211> LENGTH: 234
<212> TYPE: PRT
<213> ORGANISM: Lycopersicon esculentum

<400> SEQUENCE: 4

Met Asp Gln Gln Leu Pro Pro Thr Asn Phe Pro Val Asp Phe Pro Val
1               5                   10                  15

Tyr Arg Arg Asn Ser Ser Phe Ser Arg Leu Ile Pro Cys Leu Thr Glu
                20                  25                  30

Lys Trp Gly Asp Leu Pro Leu Lys Val Asp Asp Ser Glu Asp Met Val
                35                  40                  45

Ile Tyr Gly Leu Leu Lys Asp Ala Leu Ser Val Gly Trp Ser Pro Phe
            50                  55                  60

Asn Phe Thr Ala Gly Glu Val Lys Ser Glu Pro Arg Glu Glu Ile Glu
65                  70                  75                  80

Ser Ser Pro Glu Phe Ser Pro Ser Pro Ala Glu Thr Thr Ala Ala Pro
                85                  90                  95

```
Ala Ala Glu Thr Pro Lys Gly Arg His Tyr Arg Gly Val Arg Gln Arg
            100                 105                 110

Pro Trp Gly Lys Phe Ala Ala Glu Ile Arg Asp Pro Ala Lys Asn Gly
        115                 120                 125

Ala Arg Val Trp Leu Gly Thr Tyr Glu Thr Ala Glu Glu Ala Ala Ile
    130                 135                 140

Ala Tyr Asp Lys Ala Ala Tyr Arg Met Arg Gly Ser Lys Ala His Leu
145                 150                 155                 160

Asn Phe Pro His Arg Ile Gly Leu Asn Glu Pro Glu Pro Val Arg Val
                165                 170                 175

Thr Ala Lys Arg Arg Ala Ser Pro Glu Pro Ala Ser Ser Ser Gly Asn
            180                 185                 190

Gly Ser Met Lys Arg Arg Arg Lys Ala Val Gln Lys Cys Asp Gly Glu
        195                 200                 205

Met Ala Ser Arg Ser Ser Val Met Gln Val Gly Cys Gln Ile Glu Gln
    210                 215                 220

Leu Thr Gly Val His Gln Leu Leu Val Ile
225                 230

<210> SEQ ID NO 5
<211> LENGTH: 486
<212> TYPE: DNA
<213> ORGANISM: Lycopersicon esculentum
<220> FEATURE:
<221> NAME/KEY: CDS
<222> LOCATION: (1)..(486)
<223> OTHER INFORMATION: SlPti5

<400> SEQUENCE: 5 atg gtt cca act cca cag tct gat ctt cca ctc aac gag aac gat tct      48
Met Val Pro Thr Pro Gln Ser Asp Leu Pro Leu Asn Glu Asn Asp Ser
1               5                   10                  15 caa gag atg gtt ctt tac gag gtt ttg aac gag gct aac gct ctt aac      96
Gln Glu Met Val Leu Tyr Glu Val Leu Asn Glu Ala Asn Ala Leu Asn
                20                  25                  30 att cca tac ctc cca caa aga aac cag ctt ctc cct agg aac aac att     144
Ile Pro Tyr Leu Pro Gln Arg Asn Gln Leu Leu Pro Arg Asn Asn Ile
            35                  40                  45 ctt agg cca ctt cag tgc att gga aag aag tac agg gga gtt aga aga     192
Leu Arg Pro Leu Gln Cys Ile Gly Lys Lys Tyr Arg Gly Val Arg Arg
        50                  55                  60 agg cct tgg gga aag tat gct gct gag att aga gat tct gct aga cat     240
Arg Pro Trp Gly Lys Tyr Ala Ala Glu Ile Arg Asp Ser Ala Arg His
65                  70                  75                  80 ggt gct aga gtt tgg ctt gga act ttc gaa act gct gaa gaa gct gct     288
Gly Ala Arg Val Trp Leu Gly Thr Phe Glu Thr Ala Glu Glu Ala Ala
                85                  90                  95 ctt gct tac gat aga gct gct ttc aga atg aga ggt gct aag gct ctt     336
Leu Ala Tyr Asp Arg Ala Ala Phe Arg Met Arg Gly Ala Lys Ala Leu
            100                 105                 110 ttg aac ttc cca tcc gag att gtg aac gct tct gtg tct gtg gat aag     384
Leu Asn Phe Pro Ser Glu Ile Val Asn Ala Ser Val Ser Val Asp Lys
        115                 120                 125 ctt tct ctt tgc tcc aac tct tac acc acc aac aac aac tct gat tct     432
Leu Ser Leu Cys Ser Asn Ser Tyr Thr Thr Asn Asn Asn Ser Asp Ser
130                 135                 140 agc ctt aac gag gtt tcc tct gga act aac gat gtt ttc gag tcc agg     480
Ser Leu Asn Glu Val Ser Ser Gly Thr Asn Asp Val Phe Glu Ser Arg
                150                 155                 160
145
```

```
tgc taa                                                              486
Cys <210> SEQ ID NO 6
<211> LENGTH: 161
<212> TYPE: PRT
<213> ORGANISM: Lycopersicon esculentum

<400> SEQUENCE: 6

Met Val Pro Thr Pro Gln Ser Asp Leu Pro Leu Asn Glu Asn Asp Ser
1               5                   10                  15

Gln Glu Met Val Leu Tyr Glu Val Leu Asn Glu Ala Asn Ala Leu Asn
            20                  25                  30

Ile Pro Tyr Leu Pro Gln Arg Asn Gln Leu Leu Pro Arg Asn Asn Ile
        35                  40                  45

Leu Arg Pro Leu Gln Cys Ile Gly Lys Lys Tyr Arg Gly Val Arg Arg
    50                  55                  60

Arg Pro Trp Gly Lys Tyr Ala Ala Glu Ile Arg Asp Ser Ala Arg His
65                  70                  75                  80

Gly Ala Arg Val Trp Leu Gly Thr Phe Glu Thr Ala Glu Glu Ala Ala
                85                  90                  95

Leu Ala Tyr Asp Arg Ala Ala Phe Arg Met Arg Gly Ala Lys Ala Leu
            100                 105                 110

Leu Asn Phe Pro Ser Glu Ile Val Asn Ala Ser Val Ser Val Asp Lys
        115                 120                 125

Leu Ser Leu Cys Ser Asn Ser Tyr Thr Thr Asn Asn Asn Ser Asp Ser
    130                 135                 140

Ser Leu Asn Glu Val Ser Ser Gly Thr Asn Asp Val Phe Glu Ser Arg
145                 150                 155                 160

Cys

<210> SEQ ID NO 7
<211> LENGTH: 732
<212> TYPE: DNA
<213> ORGANISM: Arabidopsis thaliana
<220> FEATURE:
<221> NAME/KEY: CDS
<222> LOCATION: (1)..(732)
<223> OTHER INFORMATION: AtERF2

<400> SEQUENCE: 7 atg tac gga cag tgc aat ata gaa tcc gac tac gct ttg ttg gag tcg   48
Met Tyr Gly Gln Cys Asn Ile Glu Ser Asp Tyr Ala Leu Leu Glu Ser
1               5                   10                  15 ata aca cgt cac ttg cta gga gga gga gga gag aac gag ctg cga ctc   96
Ile Thr Arg His Leu Leu Gly Gly Gly Gly Glu Asn Glu Leu Arg Leu
            20                  25                  30 aat gag tca aca ccg agt tcg tgt ttc aca gag agt tgg gga ggt ttg  144
Asn Glu Ser Thr Pro Ser Ser Cys Phe Thr Glu Ser Trp Gly Gly Leu
        35                  40                  45 cca ttg aaa gag aat gat tca gag gac atg ttg gtg tac gga ctc ctc  192
Pro Leu Lys Glu Asn Asp Ser Glu Asp Met Leu Val Tyr Gly Leu Leu
    50                  55                  60 aaa gat gcc ttc cat ttt gac acg tca tca tcg gac ttg agc tgt ctt  240
Lys Asp Ala Phe His Phe Asp Thr Ser Ser Ser Asp Leu Ser Cys Leu
65                  70                  75                  80 ttt gat ttt ccg gcg gtt aaa gtc gag cca act gag aac ttt acg gcg  288
Phe Asp Phe Pro Ala Val Lys Val Glu Pro Thr Glu Asn Phe Thr Ala
                85                  90                  95
```

```
atg gag gag aaa cca aag aaa gcg ata ccg gtt acg gag acg gca gtg    336
Met Glu Glu Lys Pro Lys Lys Ala Ile Pro Val Thr Glu Thr Ala Val
            100                 105                 110 aag gcg aag cat tac aga gga gtg agg cag aga ccg tgg ggg aaa ttc    384
Lys Ala Lys His Tyr Arg Gly Val Arg Gln Arg Pro Trp Gly Lys Phe
        115                 120                 125 gcg gcg gag ata cgt gat ccg gcg aag aat gga gct agg gtt tgg tta    432
Ala Ala Glu Ile Arg Asp Pro Ala Lys Asn Gly Ala Arg Val Trp Leu
130                 135                 140 ggg acg ttt gag acg gcg gaa gat gcg gct tta gct tac gat ata gct    480
Gly Thr Phe Glu Thr Ala Glu Asp Ala Ala Leu Ala Tyr Asp Ile Ala
145                 150                 155                 160 gct ttt agg atg cgt ggt tcc cgc gct tta ttg aat ttt ccg ttg agg    528
Ala Phe Arg Met Arg Gly Ser Arg Ala Leu Leu Asn Phe Pro Leu Arg
                165                 170                 175 gtt aat tcc ggt gaa cct gac ccg gtt cgg atc acg tct aag aga tct    576
Val Asn Ser Gly Glu Pro Asp Pro Val Arg Ile Thr Ser Lys Arg Ser
            180                 185                 190 tct tcg tcg tcg tcg tcg tcc tct tct acg tcg tcg tct gaa aac        624
Ser Ser Ser Ser Ser Ser Ser Ser Ser Thr Ser Ser Ser Glu Asn
        195                 200                 205 ggg aag ttg aaa cga agg aga aaa gca gag aat ctg acg tcg gag gtg    672
Gly Lys Leu Lys Arg Arg Arg Lys Ala Glu Asn Leu Thr Ser Glu Val
210                 215                 220 gtg cag gtg aag tgt gag gtt ggt gat gag aca cgt gtt gat gag tta    720
Val Gln Val Lys Cys Glu Val Gly Asp Glu Thr Arg Val Asp Glu Leu
225                 230                 235                 240 ttg gtt tca taa                                                    732
Leu Val Ser <210> SEQ ID NO 8
<211> LENGTH: 243
<212> TYPE: PRT
<213> ORGANISM: Arabidopsis thaliana

<400> SEQUENCE: 8

Met Tyr Gly Gln Cys Asn Ile Glu Ser Asp Tyr Ala Leu Leu Glu Ser
1               5                   10                  15

Ile Thr Arg His Leu Leu Gly Gly Gly Glu Asn Glu Leu Arg Leu
            20                  25                  30

Asn Glu Ser Thr Pro Ser Ser Cys Phe Thr Glu Ser Trp Gly Gly Leu
        35                  40                  45

Pro Leu Lys Glu Asn Asp Ser Glu Asp Met Leu Val Tyr Gly Leu Leu
    50                  55                  60

Lys Asp Ala Phe His Phe Asp Thr Ser Ser Ser Asp Leu Ser Cys Leu
65                  70                  75                  80

Phe Asp Phe Pro Ala Val Lys Val Glu Pro Thr Glu Asn Phe Thr Ala
                85                  90                  95

Met Glu Glu Lys Pro Lys Lys Ala Ile Pro Val Thr Glu Thr Ala Val
            100                 105                 110

Lys Ala Lys His Tyr Arg Gly Val Arg Gln Arg Pro Trp Gly Lys Phe
        115                 120                 125

Ala Ala Glu Ile Arg Asp Pro Ala Lys Asn Gly Ala Arg Val Trp Leu
    130                 135                 140

Gly Thr Phe Glu Thr Ala Glu Asp Ala Ala Leu Ala Tyr Asp Ile Ala
145                 150                 155                 160

Ala Phe Arg Met Arg Gly Ser Arg Ala Leu Leu Asn Phe Pro Leu Arg
```

```
                165                 170                 175
Val Asn Ser Gly Glu Pro Asp Pro Val Arg Ile Thr Ser Lys Arg Ser
            180                 185                 190

Ser Ser Ser Ser Ser Ser Ser Ser Thr Ser Ser Ser Glu Asn
        195                 200                 205

Gly Lys Leu Lys Arg Arg Lys Ala Glu Asn Leu Thr Ser Glu Val
    210                 215                 220

Val Gln Val Lys Cys Glu Val Gly Asp Glu Thr Arg Val Asp Glu Leu
225                 230                 235                 240

Leu Val Ser

<210> SEQ ID NO 9
<211> LENGTH: 2466
<212> TYPE: DNA
<213> ORGANISM: Arabidopsis thaliana
<220> FEATURE:
<221> NAME/KEY: CDS
<222> LOCATION: (1)..(2466)
<223> OTHER INFORMATION: AtCTR1

<400> SEQUENCE: 9 atg gaa atg ccc ggt aga aga tct aat tac act ttg ctt agt caa ttt     48
Met Glu Met Pro Gly Arg Arg Ser Asn Tyr Thr Leu Leu Ser Gln Phe
1               5                  10                  15 tct gac gat cag gtg tca gtt tcc gtc acc gga gct cct ccg cct cac     96
Ser Asp Asp Gln Val Ser Val Ser Val Thr Gly Ala Pro Pro Pro His
                20                  25                  30 tat gat tcc ttg tcg agc gaa aac agg agc aac cat aac agc ggg aac    144
Tyr Asp Ser Leu Ser Ser Glu Asn Arg Ser Asn His Asn Ser Gly Asn
            35                  40                  45 acc ggg aaa gct aag gcg gag aga ggc gga ttt gat tgg gat cct agc    192
Thr Gly Lys Ala Lys Ala Glu Arg Gly Gly Phe Asp Trp Asp Pro Ser
        50                  55                  60 ggt ggt ggt ggt ggt gat cat agg ttg aat aat caa ccg aat cgg gtt    240
Gly Gly Gly Gly Gly Asp His Arg Leu Asn Asn Gln Pro Asn Arg Val
65                  70                  75                  80 ggg aat aat atg tat gct tcg tct cta ggg ttg caa agg caa tcc agt    288
Gly Asn Asn Met Tyr Ala Ser Ser Leu Gly Leu Gln Arg Gln Ser Ser
                85                  90                  95 ggg agt agt ttc ggt gag agc tct ttg tct ggg gat tat tac atg cct    336
Gly Ser Ser Phe Gly Glu Ser Ser Leu Ser Gly Asp Tyr Tyr Met Pro
            100                 105                 110 acg ctt tct gcg gcg gct aac gag atc gaa tct gtt gga ttt cct caa    384
Thr Leu Ser Ala Ala Ala Asn Glu Ile Glu Ser Val Gly Phe Pro Gln
        115                 120                 125 gat gat ggg ttt agg ctt gga ttt ggt ggt ggt gga gga gat ttg agg    432
Asp Asp Gly Phe Arg Leu Gly Phe Gly Gly Gly Gly Gly Asp Leu Arg
130                 135                 140 ata cag atg gcg gcg gac tcc gct gga ggg tct tca tct ggg aag agc    480
Ile Gln Met Ala Ala Asp Ser Ala Gly Gly Ser Ser Ser Gly Lys Ser
145                 150                 155                 160 tgg gcg cag cag acg gag gag agt tat cag ctg cag ctt gca ttg gcg    528
Trp Ala Gln Gln Thr Glu Glu Ser Tyr Gln Leu Gln Leu Ala Leu Ala
                165                 170                 175 tta agg ctt tcg tcg gag gct act tgt gcc gac gat ccg aac ttt ctg    576
Leu Arg Leu Ser Ser Glu Ala Thr Cys Ala Asp Asp Pro Asn Phe Leu
            180                 185                 190 gat cct gta ccg gac gag tct gct tta cgg act tcg cca agt tca gcc    624
Asp Pro Val Pro Asp Glu Ser Ala Leu Arg Thr Ser Pro Ser Ser Ala
        195                 200                 205
```

```
gaa acc gtt tca cat cgt ttc tgg gtt aat ggc tgc tta tcg tac tat         672
Glu Thr Val Ser His Arg Phe Trp Val Asn Gly Cys Leu Ser Tyr Tyr
    210                 215                 220 gat aaa gtt cct gat ggg ttt tat atg atg aat ggt ctg gat ccc tat         720
Asp Lys Val Pro Asp Gly Phe Tyr Met Met Asn Gly Leu Asp Pro Tyr
225                 230                 235                 240 att tgg acc tta tgc atc gac ctg cat gaa agt ggt cgc atc cct tca         768
Ile Trp Thr Leu Cys Ile Asp Leu His Glu Ser Gly Arg Ile Pro Ser
                245                 250                 255 att gaa tca tta aga gct gtt gat tct ggt gtt gat tct tcg ctt gaa         816
Ile Glu Ser Leu Arg Ala Val Asp Ser Gly Val Asp Ser Ser Leu Glu
            260                 265                 270 gcg atc ata gtt gat agg cgt agt gat cca gcc ttc aag gaa ctt cac         864
Ala Ile Ile Val Asp Arg Arg Ser Asp Pro Ala Phe Lys Glu Leu His
        275                 280                 285 aat aga gtc cac gac ata tct tgt agc tgc att acc aca aaa gag gtt         912
Asn Arg Val His Asp Ile Ser Cys Ser Cys Ile Thr Thr Lys Glu Val
    290                 295                 300 gtt gat cag ctg gca aag ctt atc tgc aat cgt atg ggg ggt cca gtt         960
Val Asp Gln Leu Ala Lys Leu Ile Cys Asn Arg Met Gly Gly Pro Val
305                 310                 315                 320 atc atg ggg gaa gat gag ttg gtt ccc atg tgg aag gag tgc att gat        1008
Ile Met Gly Glu Asp Glu Leu Val Pro Met Trp Lys Glu Cys Ile Asp
                325                 330                 335 ggt cta aaa gaa atc ttt aaa gtg gtg gtt ccc ata ggt agc ctc tct        1056
Gly Leu Lys Glu Ile Phe Lys Val Val Val Pro Ile Gly Ser Leu Ser
            340                 345                 350 gtt gga ctc tgc aga cat cga gct tta ctc ttc aaa gta ctg gct gac        1104
Val Gly Leu Cys Arg His Arg Ala Leu Leu Phe Lys Val Leu Ala Asp
        355                 360                 365 ata att gat tta ccc tgt cga att gcc aaa gga tgt aaa tat tgt aat        1152
Ile Ile Asp Leu Pro Cys Arg Ile Ala Lys Gly Cys Lys Tyr Cys Asn
    370                 375                 380 aga gac gat gcc gct tcg tgc ctt gtc agg ttt ggg ctt gat agg gag        1200
Arg Asp Asp Ala Ala Ser Cys Leu Val Arg Phe Gly Leu Asp Arg Glu
385                 390                 395                 400 tac ctg gtt gat tta gta gga aag cca ggt cac tta tgg gag cct gat        1248
Tyr Leu Val Asp Leu Val Gly Lys Pro Gly His Leu Trp Glu Pro Asp
                405                 410                 415 tcc ttg cta aat ggt cct tca tct atc tca att tct tct cct ctg cgg        1296
Ser Leu Leu Asn Gly Pro Ser Ser Ile Ser Ile Ser Ser Pro Leu Arg
            420                 425                 430 ttt cca cga cca aag cca gtt gaa ccc gca gtc gat ttt agg tta cta        1344
Phe Pro Arg Pro Lys Pro Val Glu Pro Ala Val Asp Phe Arg Leu Leu
        435                 440                 445 gcc aaa caa tat ttc tcc gat agc cag tct ctt aat ctt gtt ttc gat        1392
Ala Lys Gln Tyr Phe Ser Asp Ser Gln Ser Leu Asn Leu Val Phe Asp
    450                 455                 460 cct gca tca gat gat atg gga ttc tca atg ttt cat agg caa tat gat        1440
Pro Ala Ser Asp Asp Met Gly Phe Ser Met Phe His Arg Gln Tyr Asp
465                 470                 475                 480 aat ccg ggt gga gag aat gac gca ttg gca gaa aat ggt ggt ggg tct        1488
Asn Pro Gly Gly Glu Asn Asp Ala Leu Ala Glu Asn Gly Gly Gly Ser
                485                 490                 495 ttg cca ccc agt gct aat atg cct cca cag aac atg atg cgt gcg tca        1536
Leu Pro Pro Ser Ala Asn Met Pro Pro Gln Asn Met Met Arg Ala Ser
            500                 505                 510 aat caa att gaa gca gca cct atg aat gcc cca cca atc agt cag cca        1584
Asn Gln Ile Glu Ala Ala Pro Met Asn Ala Pro Pro Ile Ser Gln Pro
```

-continued

|     | 515 |     |     | 520 |     |     |     | 525 |     |     |     |     |     |     |      |
|-----|-----|-----|-----|-----|-----|-----|-----|-----|-----|-----|-----|-----|-----|-----|------|
| gtt | cca | aac | agg | gca | aat | agg | gaa | ctt | gga | ctt | gat | ggt | gat | atg | 1632 |
| Val | Pro | Asn | Arg | Ala | Asn | Arg | Glu | Leu | Gly | Leu | Asp | Gly | Asp | Met |      |
|     | 530 |     |     |     | 535 |     |     |     |     | 540 |     |     |     |     |      |

| gac | atc | ccg | tgg | tgt | gat | ctt | aat | ata | aaa | gaa | aag | att | gga | gca | ggt | 1680 |
|-----|-----|-----|-----|-----|-----|-----|-----|-----|-----|-----|-----|-----|-----|-----|-----|------|
| Asp | Ile | Pro | Trp | Cys | Asp | Leu | Asn | Ile | Lys | Glu | Lys | Ile | Gly | Ala | Gly |      |
| 545 |     |     |     |     | 550 |     |     |     |     | 555 |     |     |     |     | 560 |      |

| tcc | ttt | ggc | act | gtc | cac | cgt | gct | gag | tgg | cat | ggc | tcg | gat | gtt | gct | 1728 |
|-----|-----|-----|-----|-----|-----|-----|-----|-----|-----|-----|-----|-----|-----|-----|-----|------|
| Ser | Phe | Gly | Thr | Val | His | Arg | Ala | Glu | Trp | His | Gly | Ser | Asp | Val | Ala |      |
|     |     |     |     | 565 |     |     |     |     | 570 |     |     |     |     | 575 |     |      |

| gtg | aaa | att | ctc | atg | gag | caa | gac | ttc | cat | gct | gag | cgt | gtt | aat | gag | 1776 |
|-----|-----|-----|-----|-----|-----|-----|-----|-----|-----|-----|-----|-----|-----|-----|-----|------|
| Val | Lys | Ile | Leu | Met | Glu | Gln | Asp | Phe | His | Ala | Glu | Arg | Val | Asn | Glu |      |
|     |     |     | 580 |     |     |     |     | 585 |     |     |     |     | 590 |     |     |      |

| ttc | tta | aga | gag | gtt | gcg | ata | atg | aaa | cgc | ctt | cgc | cac | cct | aac | att | 1824 |
|-----|-----|-----|-----|-----|-----|-----|-----|-----|-----|-----|-----|-----|-----|-----|-----|------|
| Phe | Leu | Arg | Glu | Val | Ala | Ile | Met | Lys | Arg | Leu | Arg | His | Pro | Asn | Ile |      |
|     |     | 595 |     |     |     |     | 600 |     |     |     |     | 605 |     |     |     |      |

| gtt | ctc | ttc | atg | ggt | gcg | gtc | act | caa | cct | cca | aat | ttg | tca | ata | gtg | 1872 |
|-----|-----|-----|-----|-----|-----|-----|-----|-----|-----|-----|-----|-----|-----|-----|-----|------|
| Val | Leu | Phe | Met | Gly | Ala | Val | Thr | Gln | Pro | Pro | Asn | Leu | Ser | Ile | Val |      |
|     + 610 |     |     |     |     | 615 |     |     |     |     | 620 |     |     |     |     |      |

| aca | gaa | tat | ttg | tca | aga | ggt | agt | tta | tac | aga | ctt | ttg | cat | aaa | agt | 1920 |
|-----|-----|-----|-----|-----|-----|-----|-----|-----|-----|-----|-----|-----|-----|-----|-----|------|
| Thr | Glu | Tyr | Leu | Ser | Arg | Gly | Ser | Leu | Tyr | Arg | Leu | Leu | His | Lys | Ser |      |
| 625 |     |     |     |     | 630 |     |     |     |     | 635 |     |     |     |     | 640 |      |

| gga | gca | agg | gag | caa | tta | gat | gag | aga | cgt | cgc | ctg | agt | atg | gct | tat | 1968 |
|-----|-----|-----|-----|-----|-----|-----|-----|-----|-----|-----|-----|-----|-----|-----|-----|------|
| Gly | Ala | Arg | Glu | Gln | Leu | Asp | Glu | Arg | Arg | Arg | Leu | Ser | Met | Ala | Tyr |      |
|     |     |     |     | 645 |     |     |     |     | 650 |     |     |     |     | 655 |     |      |

| gat | gtg | gct | aag | gga | atg | aat | tat | ctt | cac | aat | cgc | aat | cct | cca | att | 2016 |
|-----|-----|-----|-----|-----|-----|-----|-----|-----|-----|-----|-----|-----|-----|-----|-----|------|
| Asp | Val | Ala | Lys | Gly | Met | Asn | Tyr | Leu | His | Asn | Arg | Asn | Pro | Pro | Ile |      |
|     |     |     | 660 |     |     |     |     | 665 |     |     |     |     | 670 |     |     |      |

| gtg | cat | aga | gat | cta | aaa | tct | cca | aac | tta | ttg | gtt | gac | aaa | aaa | tat | 2064 |
|-----|-----|-----|-----|-----|-----|-----|-----|-----|-----|-----|-----|-----|-----|-----|-----|------|
| Val | His | Arg | Asp | Leu | Lys | Ser | Pro | Asn | Leu | Leu | Val | Asp | Lys | Lys | Tyr |      |
|     |     | 675 |     |     |     |     | 680 |     |     |     |     | 685 |     |     |     |      |

| aca | gtc | aag | gtt | tgt | gat | ttt | ggt | ctc | tcg | cga | ttg | aag | gcc | agc | acg | 2112 |
|-----|-----|-----|-----|-----|-----|-----|-----|-----|-----|-----|-----|-----|-----|-----|-----|------|
| Thr | Val | Lys | Val | Cys | Asp | Phe | Gly | Leu | Ser | Arg | Leu | Lys | Ala | Ser | Thr |      |
|     | 690 |     |     |     |     | 695 |     |     |     |     | 700 |     |     |     |     |      |

| ttt | ctt | tcc | tcg | aag | tca | gca | gct | gga | acc | ccc | gag | tgg | atg | gca | cca | 2160 |
|-----|-----|-----|-----|-----|-----|-----|-----|-----|-----|-----|-----|-----|-----|-----|-----|------|
| Phe | Leu | Ser | Ser | Lys | Ser | Ala | Ala | Gly | Thr | Pro | Glu | Trp | Met | Ala | Pro |      |
| 705 |     |     |     |     | 710 |     |     |     |     | 715 |     |     |     |     | 720 |      |

| gaa | gtc | ctg | cga | gat | gag | ccg | tct | aat | gaa | aag | tca | gat | gtg | tac | agc | 2208 |
|-----|-----|-----|-----|-----|-----|-----|-----|-----|-----|-----|-----|-----|-----|-----|-----|------|
| Glu | Val | Leu | Arg | Asp | Glu | Pro | Ser | Asn | Glu | Lys | Ser | Asp | Val | Tyr | Ser |      |
|     |     |     | 725 |     |     |     |     | 730 |     |     |     |     | 735 |     |     |      |

| ttc | ggg | gtc | atc | ttg | tgg | gag | ctt | gct | aca | ttg | caa | caa | cca | tgg | ggt | 2256 |
|-----|-----|-----|-----|-----|-----|-----|-----|-----|-----|-----|-----|-----|-----|-----|-----|------|
| Phe | Gly | Val | Ile | Leu | Trp | Glu | Leu | Ala | Thr | Leu | Gln | Gln | Pro | Trp | Gly |      |
|     |     |     | 740 |     |     |     |     | 745 |     |     |     |     | 750 |     |     |      |

| aac | tta | aat | ccg | gct | cag | gtt | gta | gct | gcg | gtt | ggt | ttc | aag | tgt | aaa | 2304 |
|-----|-----|-----|-----|-----|-----|-----|-----|-----|-----|-----|-----|-----|-----|-----|-----|------|
| Asn | Leu | Asn | Pro | Ala | Gln | Val | Val | Ala | Ala | Val | Gly | Phe | Lys | Cys | Lys |      |
|     |     | 755 |     |     |     |     | 760 |     |     |     |     | 765 |     |     |     |      |

| cgg | ctg | gag | atc | ccg | cgt | aat | ctg | aat | cct | cag | gtt | gca | gcc | ata | atc | 2352 |
|-----|-----|-----|-----|-----|-----|-----|-----|-----|-----|-----|-----|-----|-----|-----|-----|------|
| Arg | Leu | Glu | Ile | Pro | Arg | Asn | Leu | Asn | Pro | Gln | Val | Ala | Ala | Ile | Ile |      |
|     | 770 |     |     |     |     | 775 |     |     |     |     | 780 |     |     |     |     |      |

| gag | ggt | tgt | tgg | acc | aat | gag | cca | tgg | aag | cgt | cca | tca | ttt | gca | act | 2400 |
|-----|-----|-----|-----|-----|-----|-----|-----|-----|-----|-----|-----|-----|-----|-----|-----|------|
| Glu | Gly | Cys | Trp | Thr | Asn | Glu | Pro | Trp | Lys | Arg | Pro | Ser | Phe | Ala | Thr |      |
| 785 |     |     |     |     | 790 |     |     |     |     | 795 |     |     |     |     | 800 |      |

| ata | atg | gac | ttg | cta | aga | cca | ttg | atc | aaa | tca | gcg | gtt | cct | ccg | ccc | 2448 |
|-----|-----|-----|-----|-----|-----|-----|-----|-----|-----|-----|-----|-----|-----|-----|-----|------|
| Ile | Met | Asp | Leu | Leu | Arg | Pro | Leu | Ile | Lys | Ser | Ala | Val | Pro | Pro | Pro |      |
|     |     |     |     | 805 |     |     |     |     | 810 |     |     |     |     | 815 |     |      |

| aac | cgc | tcg | gat | ttg | taa |     |     |     |     |     |     |     |     |     |     | 2466 |
|-----|-----|-----|-----|-----|-----|-----|-----|-----|-----|-----|-----|-----|-----|-----|-----|------|
| Asn | Arg | Ser | Asp | Leu |     |     |     |     |     |     |     |     |     |     |     |      |
|     |     |     |     | 820 |     |     |     |     |     |     |     |     |     |     |     |      |

<210> SEQ ID NO 10
<211> LENGTH: 821
<212> TYPE: PRT
<213> ORGANISM: Arabidopsis thaliana

<400> SEQUENCE: 10

Met Glu Met Pro Gly Arg Arg Ser Asn Tyr Thr Leu Leu Ser Gln Phe
1               5                   10                  15

Ser Asp Asp Gln Val Ser Val Ser Val Thr Gly Ala Pro Pro Pro His
            20                  25                  30

Tyr Asp Ser Leu Ser Ser Glu Asn Arg Ser Asn His Asn Ser Gly Asn
        35                  40                  45

Thr Gly Lys Ala Lys Ala Glu Arg Gly Gly Phe Asp Trp Asp Pro Ser
    50                  55                  60

Gly Gly Gly Gly Gly Asp His Arg Leu Asn Asn Gln Pro Asn Arg Val
65                  70                  75                  80

Gly Asn Asn Met Tyr Ala Ser Ser Leu Gly Leu Gln Arg Gln Ser Ser
                85                  90                  95

Gly Ser Ser Phe Gly Glu Ser Ser Leu Ser Gly Asp Tyr Tyr Met Pro
            100                 105                 110

Thr Leu Ser Ala Ala Ala Asn Glu Ile Glu Ser Val Gly Phe Pro Gln
        115                 120                 125

Asp Asp Gly Phe Arg Leu Gly Phe Gly Gly Gly Gly Asp Leu Arg
    130                 135                 140

Ile Gln Met Ala Ala Asp Ser Ala Gly Gly Ser Ser Ser Gly Lys Ser
145                 150                 155                 160

Trp Ala Gln Gln Thr Glu Glu Ser Tyr Gln Leu Gln Leu Ala Leu Ala
                165                 170                 175

Leu Arg Leu Ser Ser Glu Ala Thr Cys Ala Asp Asp Pro Asn Phe Leu
            180                 185                 190

Asp Pro Val Pro Asp Glu Ser Ala Leu Arg Thr Ser Pro Ser Ser Ala
        195                 200                 205

Glu Thr Val Ser His Arg Phe Trp Val Asn Gly Cys Leu Ser Tyr Tyr
    210                 215                 220

Asp Lys Val Pro Asp Gly Phe Tyr Met Met Asn Gly Leu Asp Pro Tyr
225                 230                 235                 240

Ile Trp Thr Leu Cys Ile Asp Leu His Glu Ser Gly Arg Ile Pro Ser
                245                 250                 255

Ile Glu Ser Leu Arg Ala Val Asp Ser Gly Val Asp Ser Ser Leu Glu
            260                 265                 270

Ala Ile Ile Val Asp Arg Arg Ser Asp Pro Ala Phe Lys Glu Leu His
        275                 280                 285

Asn Arg Val His Asp Ile Ser Cys Ser Cys Ile Thr Thr Lys Glu Val
    290                 295                 300

Val Asp Gln Leu Ala Lys Leu Ile Cys Asn Arg Met Gly Gly Pro Val
305                 310                 315                 320

Ile Met Gly Glu Asp Glu Leu Val Pro Met Trp Lys Glu Cys Ile Asp
                325                 330                 335

Gly Leu Lys Glu Ile Phe Lys Val Val Pro Ile Gly Ser Leu Ser
            340                 345                 350

Val Gly Leu Cys Arg His Arg Ala Leu Leu Phe Lys Val Leu Ala Asp
        355                 360                 365

Ile Ile Asp Leu Pro Cys Arg Ile Ala Lys Gly Cys Lys Tyr Cys Asn
    370                 375                 380

```
Arg Asp Asp Ala Ala Ser Cys Leu Val Arg Phe Gly Leu Asp Arg Glu
385                 390                 395                 400

Tyr Leu Val Asp Leu Val Gly Lys Pro Gly His Leu Trp Pro Asp
            405                 410                 415

Ser Leu Leu Asn Gly Pro Ser Ser Ile Ser Ile Ser Ser Pro Leu Arg
            420                 425                 430

Phe Pro Arg Pro Lys Pro Val Glu Pro Ala Val Asp Phe Arg Leu Leu
            435                 440                 445

Ala Lys Gln Tyr Phe Ser Asp Ser Gln Ser Leu Asn Leu Val Phe Asp
450                 455                 460

Pro Ala Ser Asp Met Gly Phe Ser Met Phe His Arg Gln Tyr Asp
465             470                 475                 480

Asn Pro Gly Gly Glu Asn Asp Ala Leu Ala Glu Asn Gly Gly Ser
                485                 490                 495

Leu Pro Pro Ser Ala Asn Met Pro Pro Gln Asn Met Met Arg Ala Ser
            500                 505                 510

Asn Gln Ile Glu Ala Ala Pro Met Asn Ala Pro Ile Ser Gln Pro
            515                 520                 525

Val Pro Asn Arg Ala Asn Arg Glu Leu Gly Leu Asp Gly Asp Met
530                 535                 540

Asp Ile Pro Trp Cys Asp Leu Asn Ile Lys Glu Lys Ile Gly Ala Gly
545                 550                 555                 560

Ser Phe Gly Thr Val His Arg Ala Glu Trp His Gly Ser Asp Val Ala
                565                 570                 575

Val Lys Ile Leu Met Glu Gln Asp Phe His Ala Glu Arg Val Asn Glu
            580                 585                 590

Phe Leu Arg Glu Val Ala Ile Met Lys Arg Leu Arg His Pro Asn Ile
            595                 600                 605

Val Leu Phe Met Gly Ala Val Thr Gln Pro Pro Asn Leu Ser Ile Val
            610                 615                 620

Thr Glu Tyr Leu Ser Arg Gly Ser Leu Tyr Arg Leu Leu His Lys Ser
625                 630                 635                 640

Gly Ala Arg Glu Gln Leu Asp Glu Arg Arg Leu Ser Met Ala Tyr
            645                 650                 655

Asp Val Ala Lys Gly Met Asn Tyr Leu His Asn Arg Asn Pro Pro Ile
            660                 665                 670

Val His Arg Asp Leu Lys Ser Pro Asn Leu Leu Val Asp Lys Lys Tyr
            675                 680                 685

Thr Val Lys Val Cys Asp Phe Gly Leu Ser Arg Leu Lys Ala Ser Thr
            690                 695                 700

Phe Leu Ser Ser Lys Ser Ala Ala Gly Thr Pro Glu Trp Met Ala Pro
705                 710                 715                 720

Glu Val Leu Arg Asp Glu Pro Ser Asn Glu Lys Ser Asp Val Tyr Ser
                725                 730                 735

Phe Gly Val Ile Leu Trp Glu Leu Ala Thr Leu Gln Gln Pro Trp Gly
            740                 745                 750

Asn Leu Asn Pro Ala Gln Val Val Ala Val Gly Phe Lys Cys Lys
            755                 760                 765

Arg Leu Glu Ile Pro Arg Asn Leu Asn Pro Gln Val Ala Ala Ile Ile
            770                 775                 780

Glu Gly Cys Trp Thr Asn Glu Pro Trp Lys Arg Pro Ser Phe Ala Thr
785                 790                 795                 800

Ile Met Asp Leu Leu Arg Pro Leu Ile Lys Ser Ala Val Pro Pro Pro
```

```
                     805                 810                 815
Asn Arg Ser Asp Leu
            820

<210> SEQ ID NO 11
<211> LENGTH: 1887
<212> TYPE: DNA
<213> ORGANISM: Arabidopsis thaliana
<220> FEATURE:
<221> NAME/KEY: CDS
<222> LOCATION: (1)..(1887)
<223> OTHER INFORMATION: AtEBF1

<400> SEQUENCE: 11 atg tct cag atc ttt agt ttt gcc ggt gaa aat gat ttt tac cgt cgt      48
Met Ser Gln Ile Phe Ser Phe Ala Gly Glu Asn Asp Phe Tyr Arg Arg
1               5                   10                  15 ggc gca ata tac cca aac cca aag gat gct agt ctt ttg tta tcg ctt      96
Gly Ala Ile Tyr Pro Asn Pro Lys Asp Ala Ser Leu Leu Leu Ser Leu
            20                  25                  30 ggt agt ttc gct gat gtt tat ttc cct cca agc aag aga tca cgt gtt     144
Gly Ser Phe Ala Asp Val Tyr Phe Pro Pro Ser Lys Arg Ser Arg Val
        35                  40                  45 gtt gca cct acg atc ttc agt gct ttc gag aaa aag cca gtt tcc att     192
Val Ala Pro Thr Ile Phe Ser Ala Phe Glu Lys Lys Pro Val Ser Ile
50                  55                  60 gat gtg cta cca gat gag tgt ctt ttt gag atc ttt agg cgt ttg tct     240
Asp Val Leu Pro Asp Glu Cys Leu Phe Glu Ile Phe Arg Arg Leu Ser
65                  70                  75                  80 gga cca caa gag agg agt gct tgc gct ttt gtc tcc aaa cag tgg ctt     288
Gly Pro Gln Glu Arg Ser Ala Cys Ala Phe Val Ser Lys Gln Trp Leu
                85                  90                  95 acg ctt gta agt agc atc cgt caa aag gag att gat gtt cct tcc aag     336
Thr Leu Val Ser Ser Ile Arg Gln Lys Glu Ile Asp Val Pro Ser Lys
            100                 105                 110 ata act gaa gat ggt gat gat tgt gaa ggg tgt ttg tct agg agc tta     384
Ile Thr Glu Asp Gly Asp Asp Cys Glu Gly Cys Leu Ser Arg Ser Leu
        115                 120                 125 gat ggg aag aag gca aca gat gtt aga ttg gca gca att gct gtt gga     432
Asp Gly Lys Lys Ala Thr Asp Val Arg Leu Ala Ala Ile Ala Val Gly
130                 135                 140 act gct ggt cgt ggg gga ctt gga aaa ttg tcg att cga ggt agc aac     480
Thr Ala Gly Arg Gly Gly Leu Gly Lys Leu Ser Ile Arg Gly Ser Asn
145                 150                 155                 160 tct gct aaa gtt tca gat ctt ggt ctt cgg tct att ggt cgt agc tgc     528
Ser Ala Lys Val Ser Asp Leu Gly Leu Arg Ser Ile Gly Arg Ser Cys
                165                 170                 175 cct tct ctc ggg tct ctt tca ctg tgg aac gtt tct acc att act gac     576
Pro Ser Leu Gly Ser Leu Ser Leu Trp Asn Val Ser Thr Ile Thr Asp
            180                 185                 190 aat gga ctt ttg gag att gct gag ggt tgt gct caa ctt gag aag ctt     624
Asn Gly Leu Leu Glu Ile Ala Glu Gly Cys Ala Gln Leu Glu Lys Leu
        195                 200                 205 gag ctg aac cgc tgc tct aca atc act gac aag ggt ttg gta gct att     672
Glu Leu Asn Arg Cys Ser Thr Ile Thr Asp Lys Gly Leu Val Ala Ile
    210                 215                 220 gct aag agc tgc ccc aac ttg act gag ctg aca ttg gag gct tgt tca     720
Ala Lys Ser Cys Pro Asn Leu Thr Glu Leu Thr Leu Glu Ala Cys Ser
225                 230                 235                 240 aga att gga gat gag ggt ttg cta gcc att gca aga tcc tgc tcc aag     768
Arg Ile Gly Asp Glu Gly Leu Leu Ala Ile Ala Arg Ser Cys Ser Lys
```

-continued

|  |  |  |  |  |  |  |  |  |  |  |  |  |  |
|---|---|---|---|---|---|---|---|---|---|---|---|---|---|
|  |  | 245 |  |  |  | 250 |  |  |  | 255 |  |  |  |
| ctg | aag | tca | gtc | tcg | atc | aag | aac | tgt | cct | ctt | gtc | agg | gat caa gga |
| Leu | Lys | Ser | Val | Ser | Ile | Lys | Asn | Cys | Pro | Leu | Val | Arg | Asp Gln Gly |
|  |  | 260 |  |  |  | 265 |  |  |  | 270 |  |  |  |

816 atc gcc tct cta ctg tct aac acc acc tgt tcc ttg gca aaa ctt aag  864
Ile Ala Ser Leu Leu Ser Asn Thr Thr Cys Ser Leu Ala Lys Leu Lys
       275                 280                 285 ctt cag atg ctg aat gtc act gat gtg tct ctt gct gtt gtg ggt cat  912
Leu Gln Met Leu Asn Val Thr Asp Val Ser Leu Ala Val Val Gly His
    290                 295                 300 tac ggc ttg tcg atc act gat ctt gtg ctc gct gga tta tca cac gtg  960
Tyr Gly Leu Ser Ile Thr Asp Leu Val Leu Ala Gly Leu Ser His Val
305                 310                 315                 320 agc gag aag gga ttc tgg gtc atg gga aat ggt gtc ggg ctc caa aaa  1008
Ser Glu Lys Gly Phe Trp Val Met Gly Asn Gly Val Gly Leu Gln Lys
            325                 330                 335 tta aac tct ctg acc atc aca gcc tgc caa gga gtg act gac atg ggg  1056
Leu Asn Ser Leu Thr Ile Thr Ala Cys Gln Gly Val Thr Asp Met Gly
        340                 345                 350 ctt gaa tct gtt gga aag ggc tgc ccg aac atg aaa aag gcg atc atc  1104
Leu Glu Ser Val Gly Lys Gly Cys Pro Asn Met Lys Lys Ala Ile Ile
    355                 360                 365 agt aaa tcc cct ttg tta tct gac aac ggg ttg gtc tct ttt gca aaa  1152
Ser Lys Ser Pro Leu Leu Ser Asp Asn Gly Leu Val Ser Phe Ala Lys
370                 375                 380 gct tct tta tca ctt gag agt ctt cag ctt gaa gaa tgc cac agg gtt  1200
Ala Ser Leu Ser Leu Glu Ser Leu Gln Leu Glu Glu Cys His Arg Val
385                 390                 395                 400 acc caa ttt ggg ttt ttt ggt tcc ctt ttg aac tgt ggt gaa aag ttg  1248
Thr Gln Phe Gly Phe Phe Gly Ser Leu Leu Asn Cys Gly Glu Lys Leu
            405                 410                 415 aag gct ttc tct ctg gtg aac tgt ttg agt att aga gat ctc acc aca  1296
Lys Ala Phe Ser Leu Val Asn Cys Leu Ser Ile Arg Asp Leu Thr Thr
        420                 425                 430 gga ttg cct gct tca tct cat tgc agc gct ctg cgc tct ttg tct att  1344
Gly Leu Pro Ala Ser Ser His Cys Ser Ala Leu Arg Ser Leu Ser Ile
    435                 440                 445 cgt aac tgc cct ggc ttt ggt gat gca aat ctt gca gcc atc ggg aag  1392
Arg Asn Cys Pro Gly Phe Gly Asp Ala Asn Leu Ala Ala Ile Gly Lys
450                 455                 460 ttg tgc cct cag ctc gag gat att gat ctg tgt ggg ctc aag ggg ata  1440
Leu Cys Pro Gln Leu Glu Asp Ile Asp Leu Cys Gly Leu Lys Gly Ile
465                 470                 475                 480 aca gag tct ggt ttc cta cat ctg att cag agc tct ctt gtg aag atc  1488
Thr Glu Ser Gly Phe Leu His Leu Ile Gln Ser Ser Leu Val Lys Ile
            485                 490                 495 aac ttc agt ggt tgt tcc aat ttg act gat aga gtg atc tct gcc atc  1536
Asn Phe Ser Gly Cys Ser Asn Leu Thr Asp Arg Val Ile Ser Ala Ile
        500                 505                 510 act gct cgt aac ggg tgg act ctt gaa gtc tta aac atc gat gga tgt  1584
Thr Ala Arg Asn Gly Trp Thr Leu Glu Val Leu Asn Ile Asp Gly Cys
    515                 520                 525 tcc aat atc act gac gcc agc ctg gtc tcc att gca gca aac tgc cag  1632
Ser Asn Ile Thr Asp Ala Ser Leu Val Ser Ile Ala Ala Asn Cys Gln
530                 535                 540 att ctc agt gat ttg gat att tcg aaa tgc gca atc tca gat tca ggg  1680
Ile Leu Ser Asp Leu Asp Ile Ser Lys Cys Ala Ile Ser Asp Ser Gly
545                 550                 555                 560 att caa gca ttg gcc tcc tct gat aag ctc aaa ctg cag atc cta tca  1728

-continued

```
Ile Gln Ala Leu Ala Ser Ser Asp Lys Leu Lys Leu Gln Ile Leu Ser
                565                 570                 575 gtt gca ggt tgc tct atg gtt aca gac aag agc ttg cca gcc atc gtc    1776
Val Ala Gly Cys Ser Met Val Thr Asp Lys Ser Leu Pro Ala Ile Val
    580                 585                 590 ggg ttg ggt tcc act cta ttg gga tta aac ctc caa cag tgt cga tcc    1824
Gly Leu Gly Ser Thr Leu Leu Gly Leu Asn Leu Gln Gln Cys Arg Ser
595                 600                 605 att tcc aat tcc act gtc gac ttc tta gtc gag cgt ctt tac aaa tgt    1872
Ile Ser Asn Ser Thr Val Asp Phe Leu Val Glu Arg Leu Tyr Lys Cys
        610                 615                 620 gac atc ctc tcc tga                                                 1887
Asp Ile Leu Ser
625

<210> SEQ ID NO 12
<211> LENGTH: 628
<212> TYPE: PRT
<213> ORGANISM: Arabidopsis thaliana

<400> SEQUENCE: 12

Met Ser Gln Ile Phe Ser Phe Ala Gly Glu Asn Asp Phe Tyr Arg Arg
1               5                   10                  15

Gly Ala Ile Tyr Pro Asn Pro Lys Asp Ala Ser Leu Leu Ser Leu
            20                  25                  30

Gly Ser Phe Ala Asp Val Tyr Phe Pro Pro Ser Lys Arg Ser Arg Val
        35                  40                  45

Val Ala Pro Thr Ile Phe Ser Ala Phe Glu Lys Lys Pro Val Ser Ile
    50                  55                  60

Asp Val Leu Pro Asp Glu Cys Leu Phe Glu Ile Phe Arg Arg Leu Ser
65                  70                  75                  80

Gly Pro Gln Glu Arg Ser Ala Cys Ala Phe Val Ser Lys Gln Trp Leu
                85                  90                  95

Thr Leu Val Ser Ser Ile Arg Gln Lys Glu Ile Asp Val Pro Ser Lys
            100                 105                 110

Ile Thr Glu Asp Gly Asp Asp Cys Glu Gly Cys Leu Ser Arg Ser Leu
        115                 120                 125

Asp Gly Lys Lys Ala Thr Asp Val Arg Leu Ala Ala Ile Ala Val Gly
    130                 135                 140

Thr Ala Gly Arg Gly Gly Leu Gly Lys Leu Ser Ile Arg Gly Ser Asn
145                 150                 155                 160

Ser Ala Lys Val Ser Asp Leu Gly Leu Arg Ser Ile Gly Arg Ser Cys
                165                 170                 175

Pro Ser Leu Gly Ser Leu Ser Leu Trp Asn Val Ser Thr Ile Thr Asp
            180                 185                 190

Asn Gly Leu Leu Glu Ile Ala Glu Gly Cys Ala Gln Leu Glu Lys Leu
        195                 200                 205

Glu Leu Asn Arg Cys Ser Thr Ile Thr Asp Lys Gly Leu Val Ala Ile
    210                 215                 220

Ala Lys Ser Cys Pro Asn Leu Thr Glu Leu Thr Leu Glu Ala Cys Ser
225                 230                 235                 240

Arg Ile Gly Asp Glu Gly Leu Leu Ala Ile Ala Arg Ser Cys Ser Lys
                245                 250                 255

Leu Lys Ser Val Ser Ile Lys Asn Cys Pro Leu Val Arg Asp Gln Gly
            260                 265                 270

Ile Ala Ser Leu Leu Ser Asn Thr Thr Cys Ser Leu Ala Lys Leu Lys
```

```
                    275                 280                 285
Leu Gln Met Leu Asn Val Thr Asp Val Ser Leu Ala Val Val Gly His
            290                 295                 300

Tyr Gly Leu Ser Ile Thr Asp Leu Val Leu Ala Gly Leu Ser His Val
305                 310                 315                 320

Ser Glu Lys Gly Phe Trp Val Met Gly Asn Gly Val Gly Leu Gln Lys
                325                 330                 335

Leu Asn Ser Leu Thr Ile Thr Ala Cys Gln Gly Val Thr Asp Met Gly
            340                 345                 350

Leu Glu Ser Val Gly Lys Gly Cys Pro Asn Met Lys Lys Ala Ile Ile
        355                 360                 365

Ser Lys Ser Pro Leu Leu Ser Asp Asn Gly Leu Val Ser Phe Ala Lys
370                 375                 380

Ala Ser Leu Ser Leu Glu Ser Leu Gln Leu Glu Glu Cys His Arg Val
385                 390                 395                 400

Thr Gln Phe Gly Phe Phe Gly Ser Leu Leu Asn Cys Gly Glu Lys Leu
                405                 410                 415

Lys Ala Phe Ser Leu Val Asn Cys Leu Ser Ile Arg Asp Leu Thr Thr
            420                 425                 430

Gly Leu Pro Ala Ser Ser His Cys Ser Ala Leu Arg Ser Leu Ser Ile
        435                 440                 445

Arg Asn Cys Pro Gly Phe Gly Asp Ala Asn Leu Ala Ala Ile Gly Lys
450                 455                 460

Leu Cys Pro Gln Leu Glu Asp Ile Asp Leu Cys Gly Leu Lys Gly Ile
465                 470                 475                 480

Thr Glu Ser Gly Phe Leu His Leu Ile Gln Ser Ser Leu Val Lys Ile
                485                 490                 495

Asn Phe Ser Gly Cys Ser Asn Leu Thr Asp Arg Val Ile Ser Ala Ile
            500                 505                 510

Thr Ala Arg Asn Gly Trp Thr Leu Glu Val Leu Asn Ile Asp Gly Cys
        515                 520                 525

Ser Asn Ile Thr Asp Ala Ser Leu Val Ser Ile Ala Ala Asn Cys Gln
530                 535                 540

Ile Leu Ser Asp Leu Asp Ile Ser Lys Cys Ala Ile Ser Asp Ser Gly
545                 550                 555                 560

Ile Gln Ala Leu Ala Ser Ser Asp Lys Leu Lys Leu Gln Ile Leu Ser
                565                 570                 575

Val Ala Gly Cys Ser Met Val Thr Asp Lys Ser Leu Pro Ala Ile Val
            580                 585                 590

Gly Leu Gly Ser Thr Leu Leu Gly Leu Asn Leu Gln Gln Cys Arg Ser
        595                 600                 605

Ile Ser Asn Ser Thr Val Asp Phe Leu Val Glu Arg Leu Tyr Lys Cys
610                 615                 620

Asp Ile Leu Ser
625

<210> SEQ ID NO 13
<211> LENGTH: 1887
<212> TYPE: DNA
<213> ORGANISM: Glycine max
<220> FEATURE:
<221> NAME/KEY: CDS
<222> LOCATION: (1)..(1887)
<223> OTHER INFORMATION: GmCTR1a

<400> SEQUENCE: 13
```

-continued

```
atg tct cag atc ttt agt ttt gcc ggt gaa aat gat ttt tac cgt cgt      48
Met Ser Gln Ile Phe Ser Phe Ala Gly Glu Asn Asp Phe Tyr Arg Arg
 1               5                  10                  15 ggc gca ata tac cca aac cca aag gat gct agt ctt ttg tta tcg ctt      96
Gly Ala Ile Tyr Pro Asn Pro Lys Asp Ala Ser Leu Leu Leu Ser Leu
             20                  25                  30 ggt agt ttc gct gat gtt tat ttc cct cca agc aag aga tca cgt gtt     144
Gly Ser Phe Ala Asp Val Tyr Phe Pro Pro Ser Lys Arg Ser Arg Val
         35                  40                  45 gtt gca cct acg atc ttc agt gct ttc gag aaa aag cca gtt tcc att     192
Val Ala Pro Thr Ile Phe Ser Ala Phe Glu Lys Lys Pro Val Ser Ile
 50                  55                  60 gat gtg cta cca gat gag tgt ctt ttt gag atc ttt agg cgt ttg tct     240
Asp Val Leu Pro Asp Glu Cys Leu Phe Glu Ile Phe Arg Arg Leu Ser
65                   70                  75                  80 gga cca caa gag agg agt gct tgc gct ttt gtc tcc aaa cag tgg ctt     288
Gly Pro Gln Glu Arg Ser Ala Cys Ala Phe Val Ser Lys Gln Trp Leu
                 85                  90                  95 acg ctt gta agt agc atc cgt caa aag gag att gat gtt cct tcc aag     336
Thr Leu Val Ser Ser Ile Arg Gln Lys Glu Ile Asp Val Pro Ser Lys
             100                 105                 110 ata act gaa gat ggt gat gat tgt gaa ggg tgt ttg tct agg agc tta     384
Ile Thr Glu Asp Gly Asp Asp Cys Glu Gly Cys Leu Ser Arg Ser Leu
         115                 120                 125 gat ggg aag aag gca aca gat gtt aga ttg gca gca att gct gtt gga     432
Asp Gly Lys Lys Ala Thr Asp Val Arg Leu Ala Ala Ile Ala Val Gly
130                 135                 140 act gct ggt cgt ggg gga ctt gga aaa ttg tcg att cga ggt agc aac     480
Thr Ala Gly Arg Gly Gly Leu Gly Lys Leu Ser Ile Arg Gly Ser Asn
145                 150                 155                 160 tct gct aaa gtt tca gat ctt ggt ctt cgg tct att ggt cgt agc tgc     528
Ser Ala Lys Val Ser Asp Leu Gly Leu Arg Ser Ile Gly Arg Ser Cys
                 165                 170                 175 cct tct ctc ggg tct ctt tca ctg tgg aac gtt tct acc att act gac     576
Pro Ser Leu Gly Ser Leu Ser Leu Trp Asn Val Ser Thr Ile Thr Asp
             180                 185                 190 aat gga ctt ttg gag att gct gag ggt tgt gct caa ctt gag aag ctt     624
Asn Gly Leu Leu Glu Ile Ala Glu Gly Cys Ala Gln Leu Glu Lys Leu
         195                 200                 205 gag ctg aac cgc tgc tct aca atc act gac aag ggt ttg gta gct att     672
Glu Leu Asn Arg Cys Ser Thr Ile Thr Asp Lys Gly Leu Val Ala Ile
210                 215                 220 gct aag agc tgc ccc aac ttg act gag ctg aca ttg gag gct tgt tca     720
Ala Lys Ser Cys Pro Asn Leu Thr Glu Leu Thr Leu Glu Ala Cys Ser
225                 230                 235                 240 aga att gga gat gag ggt ttg cta gcc att gca aga tcc tgc tcc aag     768
Arg Ile Gly Asp Glu Gly Leu Leu Ala Ile Ala Arg Ser Cys Ser Lys
                 245                 250                 255 ctg aag tca gtc tcg atc aag aac tgt cct ctt gtc agg gat caa gga     816
Leu Lys Ser Val Ser Ile Lys Asn Cys Pro Leu Val Arg Asp Gln Gly
             260                 265                 270 atc gcc tct cta ctg tct aac acc acc tgt tcc ttg gca aaa ctt aag     864
Ile Ala Ser Leu Leu Ser Asn Thr Thr Cys Ser Leu Ala Lys Leu Lys
         275                 280                 285 ctt cag atg ctg aat gtc act gat gtg tct ctt gct gtt gtg ggt cat     912
Leu Gln Met Leu Asn Val Thr Asp Val Ser Leu Ala Val Val Gly His
     290                 295                 300 tac ggc ttg tcg atc act gat ctt gtg ctc gct gga tta tca cac gtg     960
Tyr Gly Leu Ser Ile Thr Asp Leu Val Leu Ala Gly Leu Ser His Val
```

-continued

```
                305                 310                 315                 320
agc gag aag gga ttc tgg gtc atg gga aat ggt gtc ggg ctg caa aaa        1008
Ser Glu Lys Gly Phe Trp Val Met Gly Asn Gly Val Gly Leu Gln Lys
                    325                 330                 335 tta aac tct ctg acc atc aca gcc tgc caa gga gtg act gac atg ggg        1056
Leu Asn Ser Leu Thr Ile Thr Ala Cys Gln Gly Val Thr Asp Met Gly
        340                 345                 350 ctt gaa tct gtt gga aag ggc tgc ccg aac atg aaa aag gcg atc atc        1104
Leu Glu Ser Val Gly Lys Gly Cys Pro Asn Met Lys Lys Ala Ile Ile
            355                 360                 365 agt aaa tcc cct ttg tta tct gac aac ggg ttg gtc tct ttt gca aaa        1152
Ser Lys Ser Pro Leu Leu Ser Asp Asn Gly Leu Val Ser Phe Ala Lys
370                 375                 380 gct tct tta tca ctt gag agt ctt cag ctt gaa gaa tgc cac agg gtt        1200
Ala Ser Leu Ser Leu Glu Ser Leu Gln Leu Glu Glu Cys His Arg Val
385                 390                 395                 400 acc caa ttt ggg ttt ttt ggt tcc ctt ttg aac tgt ggt gaa aag ttg        1248
Thr Gln Phe Gly Phe Phe Gly Ser Leu Leu Asn Cys Gly Glu Lys Leu
                    405                 410                 415 aag gct ttc tct ctg gtg aac tgt ttg agt att aga gat ctc acc aca        1296
Lys Ala Phe Ser Leu Val Asn Cys Leu Ser Ile Arg Asp Leu Thr Thr
            420                 425                 430 gga ttg cct gct tca tct cat tgc agc gct ctg cgc tct ttg tct att        1344
Gly Leu Pro Ala Ser Ser His Cys Ser Ala Leu Arg Ser Leu Ser Ile
        435                 440                 445 cgt aac tgc cct ggc ttt ggt gat gca aat ctt gca gcc atc ggg aag        1392
Arg Asn Cys Pro Gly Phe Gly Asp Ala Asn Leu Ala Ala Ile Gly Lys
    450                 455                 460 ttg tgc cct cag ctc gag gat att gat ctg tgt ggg ctc aag ggg ata        1440
Leu Cys Pro Gln Leu Glu Asp Ile Asp Leu Cys Gly Leu Lys Gly Ile
465                 470                 475                 480 aca gag tct ggt ttc cta cat ctg att cag agc tct ctt gtg aag atc        1488
Thr Glu Ser Gly Phe Leu His Leu Ile Gln Ser Ser Leu Val Lys Ile
                    485                 490                 495 aac ttc agt ggt tgt tcc aat ttg act gat aga gtg atc tct gcc atc        1536
Asn Phe Ser Gly Cys Ser Asn Leu Thr Asp Arg Val Ile Ser Ala Ile
            500                 505                 510 act gct cgt aac ggg tgg act ctt gaa gtc tta aac atc gat gga tgt        1584
Thr Ala Arg Asn Gly Trp Thr Leu Glu Val Leu Asn Ile Asp Gly Cys
        515                 520                 525 tcc aat atc act gac gcc agc ctg gtc tcc att gca gca aac tgc cag        1632
Ser Asn Ile Thr Asp Ala Ser Leu Val Ser Ile Ala Ala Asn Cys Gln
    530                 535                 540 att ctc agt gat ttg gat att tcg aaa tgc gca atc tca gat tca ggg        1680
Ile Leu Ser Asp Leu Asp Ile Ser Lys Cys Ala Ile Ser Asp Ser Gly
545                 550                 555                 560 att caa gca ttg gcc tcc tct gat aag ctc aaa ctg cag atc cta tca        1728
Ile Gln Ala Leu Ala Ser Ser Asp Lys Leu Lys Leu Gln Ile Leu Ser
                    565                 570                 575 gtt gca ggt tgc tct atg gtt aca gac aag agc ttg cca gcc atc gtc        1776
Val Ala Gly Cys Ser Met Val Thr Asp Lys Ser Leu Pro Ala Ile Val
            580                 585                 590 ggg ttg ggt tcc act cta ttg gga tta aac ctc caa cag tgt cga tcc        1824
Gly Leu Gly Ser Thr Leu Leu Gly Leu Asn Leu Gln Gln Cys Arg Ser
        595                 600                 605 att tcc aat tcc act gtc gac ttc tta gtc gag cgt ctt tac aaa tgt        1872
Ile Ser Asn Ser Thr Val Asp Phe Leu Val Glu Arg Leu Tyr Lys Cys
    610                 615                 620 gac atc ctc tcc tga                                                    1887
Asp Ile Leu Ser
```

Asp Ile Leu Ser
625

<210> SEQ ID NO 14
<211> LENGTH: 628
<212> TYPE: PRT
<213> ORGANISM: Glycine max

<400> SEQUENCE: 14

```
Met Ser Gln Ile Phe Ser Phe Ala Gly Glu Asn Asp Phe Tyr Arg Arg
1               5                   10                  15

Gly Ala Ile Tyr Pro Asn Pro Lys Asp Ala Ser Leu Leu Ser Leu
            20                  25                  30

Gly Ser Phe Ala Asp Val Tyr Phe Pro Pro Ser Lys Arg Ser Arg Val
                35                  40                  45

Val Ala Pro Thr Ile Phe Ser Ala Phe Glu Lys Lys Pro Val Ser Ile
        50                  55                  60

Asp Val Leu Pro Asp Glu Cys Leu Phe Glu Ile Phe Arg Arg Leu Ser
65                  70                  75                  80

Gly Pro Gln Glu Arg Ser Ala Cys Ala Phe Val Ser Lys Gln Trp Leu
                85                  90                  95

Thr Leu Val Ser Ser Ile Arg Gln Lys Glu Ile Asp Val Pro Ser Lys
            100                 105                 110

Ile Thr Glu Asp Gly Asp Asp Cys Glu Gly Cys Leu Ser Arg Ser Leu
        115                 120                 125

Asp Gly Lys Lys Ala Thr Asp Val Arg Leu Ala Ala Ile Ala Val Gly
130                 135                 140

Thr Ala Gly Arg Gly Gly Leu Gly Lys Leu Ser Ile Arg Gly Ser Asn
145                 150                 155                 160

Ser Ala Lys Val Ser Asp Leu Gly Leu Arg Ser Ile Gly Arg Ser Cys
                165                 170                 175

Pro Ser Leu Gly Ser Leu Ser Leu Trp Asn Val Ser Thr Ile Thr Asp
            180                 185                 190

Asn Gly Leu Leu Glu Ile Ala Glu Gly Cys Ala Gln Leu Glu Lys Leu
        195                 200                 205

Glu Leu Asn Arg Cys Ser Thr Ile Thr Asp Lys Gly Leu Val Ala Ile
    210                 215                 220

Ala Lys Ser Cys Pro Asn Leu Thr Glu Leu Thr Leu Glu Ala Cys Ser
225                 230                 235                 240

Arg Ile Gly Asp Glu Gly Leu Leu Ala Ile Ala Arg Ser Cys Ser Lys
                245                 250                 255

Leu Lys Ser Val Ser Ile Lys Asn Cys Pro Leu Val Arg Asp Gln Gly
            260                 265                 270

Ile Ala Ser Leu Leu Ser Asn Thr Thr Cys Ser Leu Ala Lys Leu Lys
        275                 280                 285

Leu Gln Met Leu Asn Val Thr Asp Val Ser Leu Ala Val Val Gly His
    290                 295                 300

Tyr Gly Leu Ser Ile Thr Asp Leu Val Leu Ala Gly Leu Ser His Val
305                 310                 315                 320

Ser Glu Lys Gly Phe Trp Val Met Gly Asn Gly Val Gly Leu Gln Lys
                325                 330                 335

Leu Asn Ser Leu Thr Ile Thr Ala Cys Gln Gly Val Thr Asp Met Gly
            340                 345                 350

Leu Glu Ser Val Gly Lys Gly Cys Pro Asn Met Lys Lys Ala Ile Ile
        355                 360                 365
```

```
Ser Lys Ser Pro Leu Ser Asp Asn Gly Leu Val Ser Phe Ala Lys
    370                 375                 380

Ala Ser Leu Ser Leu Glu Ser Leu Gln Leu Glu Glu Cys His Arg Val
385                 390                 395                 400

Thr Gln Phe Gly Phe Gly Ser Leu Leu Asn Cys Gly Glu Lys Leu
                405                 410                 415

Lys Ala Phe Ser Leu Val Asn Cys Leu Ser Ile Arg Asp Leu Thr Thr
                420                 425                 430

Gly Leu Pro Ala Ser Ser His Cys Ser Ala Leu Arg Ser Leu Ser Ile
                435                 440                 445

Arg Asn Cys Pro Gly Phe Gly Asp Ala Asn Leu Ala Ala Ile Gly Lys
    450                 455                 460

Leu Cys Pro Gln Leu Glu Asp Ile Asp Leu Cys Gly Leu Lys Gly Ile
465                 470                 475                 480

Thr Glu Ser Gly Phe Leu His Leu Ile Gln Ser Ser Leu Val Lys Ile
                485                 490                 495

Asn Phe Ser Gly Cys Ser Asn Leu Thr Asp Arg Val Ile Ser Ala Ile
                500                 505                 510

Thr Ala Arg Asn Gly Trp Thr Leu Glu Val Leu Asn Ile Asp Gly Cys
    515                 520                 525

Ser Asn Ile Thr Asp Ala Ser Leu Val Ser Ile Ala Ala Asn Cys Gln
    530                 535                 540

Ile Leu Ser Asp Leu Asp Ile Ser Lys Cys Ala Ile Ser Asp Ser Gly
545                 550                 555                 560

Ile Gln Ala Leu Ala Ser Ser Asp Lys Leu Lys Leu Gln Ile Leu Ser
                565                 570                 575

Val Ala Gly Cys Ser Met Val Thr Asp Lys Ser Leu Pro Ala Ile Val
                580                 585                 590

Gly Leu Gly Ser Thr Leu Leu Gly Leu Asn Leu Gln Gln Cys Arg Ser
                595                 600                 605

Ile Ser Asn Ser Thr Val Asp Phe Leu Val Glu Arg Leu Tyr Lys Cys
    610                 615                 620

Asp Ile Leu Ser
625
```

```
<210> SEQ ID NO 15
<211> LENGTH: 2382
<212> TYPE: DNA
<213> ORGANISM: Glycine max
<220> FEATURE:
<221> NAME/KEY: CDS
<222> LOCATION: (1)..(2382)
<223> OTHER INFORMATION: GmCTR1b

<400> SEQUENCE: 15
```

```
atg gaa atg cct gcc aga aga tcc aac tat tcg ctc ctc agc caa att      48
Met Glu Met Pro Ala Arg Arg Ser Asn Tyr Ser Leu Leu Ser Gln Ile
1               5                   10                  15 ccc gac gac cag ttc tcc tcc gcc gcc gct ccc tca tcc tcc ggc gac      96
Pro Asp Asp Gln Phe Ser Ser Ala Ala Ala Pro Ser Ser Ser Gly Asp
                20                  25                  30 ggc aag gcc ggc cgt gcc gga aag tcc gac cgt gcc gcc ttc gaa tgg     144
Gly Lys Ala Gly Arg Ala Gly Lys Ser Asp Arg Ala Ala Phe Glu Trp
            35                  40                  45 gac ctc gtc gct gat cac cgg gcc gcc aac cgg atc gga aac gtc tac     192
Asp Leu Val Ala Asp His Arg Ala Ala Asn Arg Ile Gly Asn Val Tyr
        50                  55                  60
```

-continued

| | | |
|---|---|---|
| tcc tcg ata ggc ctg cag cgc cag tcc agc ggg agc agc tac ggc gag<br>Ser Ser Ile Gly Leu Gln Arg Gln Ser Ser Gly Ser Ser Tyr Gly Glu<br>65                        70                    75                      80 | 240 |

```
tcc tcg ata ggc ctg cag cgc cag tcc agc ggg agc agc tac ggc gag      240
Ser Ser Ile Gly Leu Gln Arg Gln Ser Ser Gly Ser Ser Tyr Gly Glu
 65                  70                  75                  80 agc tcg ctc tcc ggc ggc ggc gac ttc tac gct ccg acg atc tcc acg      288
Ser Ser Leu Ser Gly Gly Gly Asp Phe Tyr Ala Pro Thr Ile Ser Thr
                 85                  90                  95 gcg gcg gcc agc gac gtc gac gcc ttc ggc tac ctc cac gac gag cga      336
Ala Ala Ala Ser Asp Val Asp Ala Phe Gly Tyr Leu His Asp Glu Arg
            100                 105                 110 agc aag ttc tcg gag gcg gcg ccg gcg agg atc gcc ggc tcc tcc tcc      384
Ser Lys Phe Ser Glu Ala Ala Pro Ala Arg Ile Ala Gly Ser Ser Ser
        115                 120                 125 ggg aag agc tgg gcg cag cag acg gag gag agc tac cag ctg cag ctc      432
Gly Lys Ser Trp Ala Gln Gln Thr Glu Glu Ser Tyr Gln Leu Gln Leu
130                 135                 140 gcg ctc gct ctg cgg ctc tcg tcc gac gcc acg tgc gcc gat gat ccc      480
Ala Leu Ala Leu Arg Leu Ser Ser Asp Ala Thr Cys Ala Asp Asp Pro
145                 150                 155                 160 aat ttc ctc gat ccg ttg ttg cat gaa tta tgt tta aga gga aaa aat      528
Asn Phe Leu Asp Pro Leu Leu His Glu Leu Cys Leu Arg Gly Lys Asn
                165                 170                 175 atc cct tca ctc ttt att cta ctc cat ttt tct ttt ttg aaa atc atc      576
Ile Pro Ser Leu Phe Ile Leu Leu His Phe Ser Phe Leu Lys Ile Ile
            180                 185                 190 tct tgt ttt ccc tgg aaa gtt gag gga gga aac tgg aag ttg tac cgt      624
Ser Cys Phe Pro Trp Lys Val Glu Gly Gly Asn Trp Lys Leu Tyr Arg
        195                 200                 205 ttt gat ggc ttt tac cta att cac ggg atg gat tcc ttt gtc tgg acc      672
Phe Asp Gly Phe Tyr Leu Ile His Gly Met Asp Ser Phe Val Trp Thr
210                 215                 220 atg tgc act gat ctg cat gaa aat gga cga att cca tca gtt gat atg      720
Met Cys Thr Asp Leu His Glu Asn Gly Arg Ile Pro Ser Val Asp Met
225                 230                 235                 240 ctg aag tct gtg aat ccc tgt gtc gtt cct tca ctc gaa gta gtt atg      768
Leu Lys Ser Val Asn Pro Cys Val Val Pro Ser Leu Glu Val Val Met
                245                 250                 255 gtg gat cga tgc agt gac ccc agc tta aga gat ctg caa aat agt gtt      816
Val Asp Arg Cys Ser Asp Pro Ser Leu Arg Asp Leu Gln Asn Ser Val
            260                 265                 270 cat aac att tct ttc act agc ata aca aca aca gat gtt gta gat aaa      864
His Asn Ile Ser Phe Thr Ser Ile Thr Thr Thr Asp Val Val Asp Lys
        275                 280                 285 ctt tcc aag ctg gtt tgc aac cgt atg ggg ggt tca gct tct gtt ggg      912
Leu Ser Lys Leu Val Cys Asn Arg Met Gly Gly Ser Ala Ser Val Gly
290                 295                 300 gaa gat cac ttt ttt tcc atc tgg agg aat tgc agt aat gat ctg aaa      960
Glu Asp His Phe Phe Ser Ile Trp Arg Asn Cys Ser Asn Asp Leu Lys
305                 310                 315                 320 gat tgc tta gga tct gtt gtt att ccc ata ggt agt cta tct gtt ggc     1008
Asp Cys Leu Gly Ser Val Val Ile Pro Ile Gly Ser Leu Ser Val Gly
                325                 330                 335 ctc tgc cgg cat cgt gct ata tta ttc aaa gta cta gct gac gcc att     1056
Leu Cys Arg His Arg Ala Ile Leu Phe Lys Val Leu Ala Asp Ala Ile
            340                 345                 350 gat tta cca tgt cga att gct aag ggc tgt aaa tat tgc aaa agg gat     1104
Asp Leu Pro Cys Arg Ile Ala Lys Gly Cys Lys Tyr Cys Lys Arg Asp
        355                 360                 365 gat gct tca tct tgt ctt gtt cga ttt ggg att gag agg gag tat ctt     1152
Asp Ala Ser Ser Cys Leu Val Arg Phe Gly Ile Glu Arg Glu Tyr Leu
```

-continued

```
                370                 375                 380
gtt gat tta att gga aag cca gga aac tta tcc gag cct gat tcc ttg    1200
Val Asp Leu Ile Gly Lys Pro Gly Asn Leu Ser Glu Pro Asp Ser Leu
385                 390                 395                 400 ctc aat ggt cca tct tcc atc tca ttt tct tca ccc ttg cgc ttt cca    1248
Leu Asn Gly Pro Ser Ser Ile Ser Phe Ser Ser Pro Leu Arg Phe Pro
                405                 410                 415 cga ctt aaa cca gct gaa act acc att gat ttc agg tca ctg gcc aaa    1296
Arg Leu Lys Pro Ala Glu Thr Thr Ile Asp Phe Arg Ser Leu Ala Lys
        420                 425                 430 cag tat ttc tcg gac tgt gtg tct ctt gag ctt gtc ttt gac aac aat    1344
Gln Tyr Phe Ser Asp Cys Val Ser Leu Glu Leu Val Phe Asp Asn Asn
            435                 440                 445 tct gca gat tct cat cca agc tca cgg gaa caa ggt tcc gaa aca tat    1392
Ser Ala Asp Ser His Pro Ser Ser Arg Glu Gln Gly Ser Glu Thr Tyr
450                 455                 460 caa tca tgt aac cct cct cag aac att gta gac tcg act gtg gga aat    1440
Gln Ser Cys Asn Pro Pro Gln Asn Ile Val Asp Ser Thr Val Gly Asn
465                 470                 475                 480 caa ctg att cct agc aaa cat gct cga gag ctt aac ctt gac atg gag    1488
Gln Leu Ile Pro Ser Lys His Ala Arg Glu Leu Asn Leu Asp Met Glu
                485                 490                 495 gat ttg gac ata cca tgg tgc gat ctt gtt tta aga gag aaa ata ggg    1536
Asp Leu Asp Ile Pro Trp Cys Asp Leu Val Leu Arg Glu Lys Ile Gly
        500                 505                 510 tca ggt tct ttt gga act gta cat cgt gct gag tgg aat ggc tcg gac    1584
Ser Gly Ser Phe Gly Thr Val His Arg Ala Glu Trp Asn Gly Ser Asp
            515                 520                 525 gtt gct gtg aaa att ttg atg gaa cag gat ttt ctt gct gag cgc ttc    1632
Val Ala Val Lys Ile Leu Met Glu Gln Asp Phe Leu Ala Glu Arg Phe
530                 535                 540 aag gaa ttc cta agg gag gtt gca ata atg aaa cgt tta cgg cat cca    1680
Lys Glu Phe Leu Arg Glu Val Ala Ile Met Lys Arg Leu Arg His Pro
545                 550                 555                 560 aac att gtt ttg ttt atg ggg gca gtc act cag cct cct aac tta tca    1728
Asn Ile Val Leu Phe Met Gly Ala Val Thr Gln Pro Pro Asn Leu Ser
                565                 570                 575 att gtc aca gaa tat tta tca agg ttg ggt agc tta tat agg ctg ttg    1776
Ile Val Thr Glu Tyr Leu Ser Arg Leu Gly Ser Leu Tyr Arg Leu Leu
        580                 585                 590 cat agg tct ggt gcc aaa gaa gta ttg gat gag cgg cgt agg ctt ggt    1824
His Arg Ser Gly Ala Lys Glu Val Leu Asp Glu Arg Arg Arg Leu Gly
            595                 600                 605 atg gct tat gac gtg gca aag ggg atg aat tat ctt cat aaa cgt aat    1872
Met Ala Tyr Asp Val Ala Lys Gly Met Asn Tyr Leu His Lys Arg Asn
610                 615                 620 ccc ccc att gtt cat aga gat ctg aaa tct cca aac ctt ctt gtt gac    1920
Pro Pro Ile Val His Arg Asp Leu Lys Ser Pro Asn Leu Leu Val Asp
625                 630                 635                 640 aag aaa tat aca gtg aag gtt tgt gat ttt ggg ctt tca cgt ctg aag    1968
Lys Lys Tyr Thr Val Lys Val Cys Asp Phe Gly Leu Ser Arg Leu Lys
                645                 650                 655 gcc aat aca ttt ctc tca tcc aaa tca gct gct ggg act cct gag tgg    2016
Ala Asn Thr Phe Leu Ser Ser Lys Ser Ala Ala Gly Thr Pro Glu Trp
        660                 665                 670 atg gct cca gag gtt ctt cgt gat gag cca tcg aat gag aag tct gat    2064
Met Ala Pro Glu Val Leu Arg Asp Glu Pro Ser Asn Glu Lys Ser Asp
            675                 680                 685 gtt tac agc ttt ggt gta atc tta tgg gag ctt gca aca ttg caa cag    2112
```

```
Val Tyr Ser Phe Gly Val Ile Leu Trp Glu Leu Ala Thr Leu Gln Gln
        690                 695                 700 cca tgg att aat tta aat cca gca cag gtt gtg gca gct gtt ggc ttt    2160
Pro Trp Ile Asn Leu Asn Pro Ala Gln Val Val Ala Ala Val Gly Phe
705                 710                 715                 720 aag ggg aaa agg cta gag atc cca cat gat gtg aat cct caa gta gct    2208
Lys Gly Lys Arg Leu Glu Ile Pro His Asp Val Asn Pro Gln Val Ala
                725                 730                 735 gca cta att gat gct tgc tgg gcg aat gag cct tgg aaa cgt cct tct    2256
Ala Leu Ile Asp Ala Cys Trp Ala Asn Glu Pro Trp Lys Arg Pro Ser
            740                 745                 750 ttt gcc agt att atg gat tct ttg agg cca ttg ctc aaa ccc cct aca    2304
Phe Ala Ser Ile Met Asp Ser Leu Arg Pro Leu Leu Lys Pro Pro Thr
        755                 760                 765 cct caa cct ggt tct ttt cat gca cat atg aca gga ttt tat tgg tct    2352
Pro Gln Pro Gly Ser Phe His Ala His Met Thr Gly Phe Tyr Trp Ser
770                 775                 780 ttg atg tct aac aag att aca ctg ctt tag                            2382
Leu Met Ser Asn Lys Ile Thr Leu Leu
785                 790

<210> SEQ ID NO 16
<211> LENGTH: 793
<212> TYPE: PRT
<213> ORGANISM: Glycine max

<400> SEQUENCE: 16

Met Glu Met Pro Ala Arg Arg Ser Asn Tyr Ser Leu Leu Ser Gln Ile
1               5                   10                  15

Pro Asp Asp Gln Phe Ser Ser Ala Ala Pro Ser Ser Ser Gly Asp
            20                  25                  30

Gly Lys Ala Gly Arg Ala Gly Lys Ser Asp Arg Ala Ala Phe Glu Trp
        35                  40                  45

Asp Leu Val Ala Asp His Arg Ala Ala Asn Arg Ile Gly Asn Val Tyr
    50                  55                  60

Ser Ser Ile Gly Leu Gln Arg Gln Ser Gly Ser Ser Tyr Gly Glu
65                  70                  75                  80

Ser Ser Leu Ser Gly Gly Asp Phe Tyr Ala Pro Thr Ile Ser Thr
                85                  90                  95

Ala Ala Ala Ser Asp Val Asp Ala Phe Gly Tyr Leu His Asp Glu Arg
            100                 105                 110

Ser Lys Phe Ser Glu Ala Ala Pro Ala Arg Ile Ala Gly Ser Ser Ser
        115                 120                 125

Gly Lys Ser Trp Ala Gln Gln Thr Glu Glu Ser Tyr Gln Leu Gln Leu
    130                 135                 140

Ala Leu Ala Leu Arg Leu Ser Ser Asp Ala Thr Cys Ala Asp Asp Pro
145                 150                 155                 160

Asn Phe Leu Asp Pro Leu Leu His Glu Leu Cys Leu Arg Gly Lys Asn
                165                 170                 175

Ile Pro Ser Leu Phe Ile Leu Leu His Phe Ser Phe Leu Lys Ile Ile
            180                 185                 190

Ser Cys Phe Pro Trp Lys Val Glu Gly Gly Asn Trp Lys Leu Tyr Arg
        195                 200                 205

Phe Asp Gly Phe Tyr Leu Ile His Gly Met Asp Ser Phe Val Trp Thr
    210                 215                 220

Met Cys Thr Asp Leu His Glu Asn Gly Arg Ile Pro Ser Val Asp Met
225                 230                 235                 240
```

```
Leu Lys Ser Val Asn Pro Cys Val Pro Ser Leu Glu Val Met
            245                 250                 255

Val Asp Arg Cys Ser Asp Pro Ser Leu Arg Asp Leu Gln Asn Ser Val
            260                 265                 270

His Asn Ile Ser Phe Thr Ser Ile Thr Thr Thr Asp Val Val Asp Lys
            275                 280                 285

Leu Ser Lys Leu Val Cys Asn Arg Met Gly Ser Ala Ser Val Gly
            290                 295                 300

Glu Asp His Phe Phe Ser Ile Trp Arg Asn Cys Ser Asn Asp Leu Lys
305                     310                 315                 320

Asp Cys Leu Gly Ser Val Val Ile Pro Ile Gly Ser Leu Ser Val Gly
                    325                 330                 335

Leu Cys Arg His Arg Ala Ile Leu Phe Lys Val Leu Ala Asp Ala Ile
                    340                 345                 350

Asp Leu Pro Cys Arg Ile Ala Lys Gly Cys Lys Tyr Cys Lys Arg Asp
                355                 360                 365

Asp Ala Ser Ser Cys Leu Val Arg Phe Gly Ile Glu Arg Glu Tyr Leu
            370                 375                 380

Val Asp Leu Ile Gly Lys Pro Gly Asn Leu Ser Glu Pro Asp Ser Leu
385                     390                 395                 400

Leu Asn Gly Pro Ser Ser Ile Ser Phe Ser Ser Pro Leu Arg Phe Pro
                    405                 410                 415

Arg Leu Lys Pro Ala Glu Thr Thr Ile Asp Phe Arg Ser Leu Ala Lys
                    420                 425                 430

Gln Tyr Phe Ser Asp Cys Val Ser Leu Glu Leu Val Phe Asp Asn Asn
                435                 440                 445

Ser Ala Asp Ser His Pro Ser Ser Arg Glu Gln Gly Ser Glu Thr Tyr
            450                 455                 460

Gln Ser Cys Asn Pro Pro Gln Asn Ile Val Asp Ser Thr Val Gly Asn
465                     470                 475                 480

Gln Leu Ile Pro Ser Lys His Ala Arg Glu Leu Asn Leu Asp Met Glu
                    485                 490                 495

Asp Leu Asp Ile Pro Trp Cys Asp Leu Val Leu Arg Glu Lys Ile Gly
                    500                 505                 510

Ser Gly Ser Phe Gly Thr Val His Arg Ala Glu Trp Asn Gly Ser Asp
                515                 520                 525

Val Ala Val Lys Ile Leu Met Glu Gln Asp Phe Leu Ala Glu Arg Phe
            530                 535                 540

Lys Glu Phe Leu Arg Glu Val Ala Ile Met Lys Arg Leu Arg His Pro
545                     550                 555                 560

Asn Ile Val Leu Phe Met Gly Ala Val Thr Gln Pro Pro Asn Leu Ser
                    565                 570                 575

Ile Val Thr Glu Tyr Leu Ser Arg Leu Gly Ser Leu Tyr Arg Leu Leu
                    580                 585                 590

His Arg Ser Gly Ala Lys Glu Val Leu Asp Glu Arg Arg Arg Leu Gly
                595                 600                 605

Met Ala Tyr Asp Val Ala Lys Gly Met Asn Tyr Leu His Lys Arg Asn
            610                 615                 620

Pro Pro Ile Val His Arg Asp Leu Lys Ser Pro Asn Leu Leu Val Asp
625                     630                 635                 640

Lys Lys Tyr Thr Val Lys Val Cys Asp Phe Gly Leu Ser Arg Leu Lys
                    645                 650                 655
```

```
Ala Asn Thr Phe Leu Ser Ser Lys Ser Ala Ala Gly Thr Pro Glu Trp
            660                 665                 670

Met Ala Pro Glu Val Leu Arg Asp Pro Ser Asn Glu Lys Ser Asp
        675                 680                 685

Val Tyr Ser Phe Gly Val Ile Leu Trp Glu Leu Ala Thr Leu Gln Gln
    690                 695                 700

Pro Trp Ile Asn Leu Asn Pro Ala Gln Val Val Ala Ala Val Gly Phe
705                 710                 715                 720

Lys Gly Lys Arg Leu Glu Ile Pro His Asp Val Asn Pro Gln Val Ala
                725                 730                 735

Ala Leu Ile Asp Ala Cys Trp Ala Asn Glu Pro Trp Lys Arg Pro Ser
            740                 745                 750

Phe Ala Ser Ile Met Asp Ser Leu Arg Pro Leu Leu Lys Pro Pro Thr
        755                 760                 765

Pro Gln Pro Gly Ser Phe His Ala His Met Thr Gly Phe Tyr Trp Ser
    770                 775                 780

Leu Met Ser Asn Lys Ile Thr Leu Leu
785                 790

<210> SEQ ID NO 17
<211> LENGTH: 2412
<212> TYPE: DNA
<213> ORGANISM: Glycine max
<220> FEATURE:
<221> NAME/KEY: CDS
<222> LOCATION: (1)..(2412)
<223> OTHER INFORMATION: GmCTR1c

<400> SEQUENCE: 17 atg gaa atg cct gcc aga aga tcc ggc aac tac acc ctc ctc agt caa    48
Met Glu Met Pro Ala Arg Arg Ser Gly Asn Tyr Thr Leu Leu Ser Gln
1               5                   10                  15 act cct gac gac aac tta acg gcg ccg ttg ttc ggt tgc tcc tcc ggc    96
Thr Pro Asp Asp Asn Leu Thr Ala Pro Leu Phe Gly Cys Ser Ser Gly
                20                  25                  30 gac ggt caa atc aac agc agc aag ttc gag aga gtc tcc gat tgg gac   144
Asp Gly Gln Ile Asn Ser Ser Lys Phe Glu Arg Val Ser Asp Trp Asp
            35                  40                  45 tcc ggc gtc gaa cac cga cag ggg aat cgg atc ggg aat ttg cac tcc   192
Ser Gly Val Glu His Arg Gln Gly Asn Arg Ile Gly Asn Leu His Ser
        50                  55                  60 tcg ttc ggg atg cag cgg cag tcc agc gag ggc agt ttc ggc gag agc   240
Ser Phe Gly Met Gln Arg Gln Ser Ser Glu Gly Ser Phe Gly Glu Ser
65                  70                  75                  80 tct ctc tcc ggc gag ttc tac gcg ccg act ctg tcg gct atc gcg gcg   288
Ser Leu Ser Gly Glu Phe Tyr Ala Pro Thr Leu Ser Ala Ile Ala Ala
                85                  90                  95 aat gag atc gac gga ttc aga ggc acg ttt gcg gga aat tcg gcg gcg   336
Asn Glu Ile Asp Gly Phe Arg Gly Thr Phe Ala Gly Asn Ser Ala Ala
                100                 105                 110 agg agc gga ggt tcc tcc ggc aag agc tgg gcg cag cag acg gag gag   384
Arg Ser Gly Gly Ser Ser Gly Lys Ser Trp Ala Gln Gln Thr Glu Glu
            115                 120                 125 agt tac caa tta cag ttg gca ctg gct ctt cgg ctt tcc tcg gag gcc   432
Ser Tyr Gln Leu Gln Leu Ala Leu Ala Leu Arg Leu Ser Ser Glu Ala
        130                 135                 140 acg tgt gct gat gat ccc aat ttt ctg gat ccc gtg ccc gac gaa tcc   480
Thr Cys Ala Asp Asp Pro Asn Phe Leu Asp Pro Val Pro Asp Glu Ser
145                 150                 155                 160
```

```
gcg ttg agg tct tta tcc tcg ttt tcc gca gag gca gtg tcg cat agg      528
Ala Leu Arg Ser Leu Ser Ser Phe Ser Ala Glu Ala Val Ser His Arg
            165                 170                 175 ttt tgg gtg aag gga tgc cta tta tac ttc gac aaa att cct gat ggc      576
Phe Trp Val Lys Gly Cys Leu Leu Tyr Phe Asp Lys Ile Pro Asp Gly
        180                 185                 190 ttt tat cta att cat ggg atg gat ccc tat gta tgg act gtg tgc acc      624
Phe Tyr Leu Ile His Gly Met Asp Pro Tyr Val Trp Thr Val Cys Thr
    195                 200                 205 aat ctt cag gaa aat ggc cga att cct tcg ctt gag aca cta aaa tct      672
Asn Leu Gln Glu Asn Gly Arg Ile Pro Ser Leu Glu Thr Leu Lys Ser
210                 215                 220 ata aat cct tct gat tct tca ctt gaa gta gtt ttt gtg gat aga cgt      720
Ile Asn Pro Ser Asp Ser Ser Leu Glu Val Val Phe Val Asp Arg Arg
225                 230                 235                 240 aat gat cct agc tta cga gaa ctg caa aac aaa gta caa gac att tct      768
Asn Asp Pro Ser Leu Arg Glu Leu Gln Asn Lys Val Gln Asp Ile Ser
                245                 250                 255 tgt tgc tgc ata gca aca act gat gtt gta gac cag ctt gcg aag ctg      816
Cys Cys Cys Ile Ala Thr Thr Asp Val Val Asp Gln Leu Ala Lys Leu
            260                 265                 270 gtt tgc aat tgt atg ggg ggc tca gct tct gta tgg gaa gat gat ctt      864
Val Cys Asn Cys Met Gly Gly Ser Ala Ser Val Trp Glu Asp Asp Leu
        275                 280                 285 ttt cct ata tgg agg gag cgc att aat gat cta aga gat tgc tta gga      912
Phe Pro Ile Trp Arg Glu Arg Ile Asn Asp Leu Arg Asp Cys Leu Gly
    290                 295                 300 tct gtc gtt gta cca att gga agt cta tct act gga ctt tgc agg cat      960
Ser Val Val Val Pro Ile Gly Ser Leu Ser Thr Gly Leu Cys Arg His
305                 310                 315                 320 cgt gct gta tta ttc aaa gta cta gct gac acc att gat ttg cca tgc     1008
Arg Ala Val Leu Phe Lys Val Leu Ala Asp Thr Ile Asp Leu Pro Cys
                325                 330                 335 cga att gct aag ggc tgt aaa tat tgt tca aga gat gat gcc tcc tca     1056
Arg Ile Ala Lys Gly Cys Lys Tyr Cys Ser Arg Asp Asp Ala Ser Ser
            340                 345                 350 tgt ctt gtt cga ttt gga ctt gac agg gaa tac atg gtt gat ctt att     1104
Cys Leu Val Arg Phe Gly Leu Asp Arg Glu Tyr Met Val Asp Leu Ile
        355                 360                 365 ggg aag ccg ggt tgc tta tgc gag cct gat tcc ttg gtc aat ggt cca     1152
Gly Lys Pro Gly Cys Leu Cys Glu Pro Asp Ser Leu Val Asn Gly Pro
    370                 375                 380 tct tcc att tca ttt tct tca ccc ttg tgc ttt ccg aga cat aaa cca     1200
Ser Ser Ile Ser Phe Ser Ser Pro Leu Cys Phe Pro Arg His Lys Pro
385                 390                 395                 400 gct gaa cct acc att gat ttc agg tca ctg gcc aaa caa tat ttc tcg     1248
Ala Glu Pro Thr Ile Asp Phe Arg Ser Leu Ala Lys Gln Tyr Phe Ser
                405                 410                 415 gat tgt atg tct gct gag ctt gtc ttc gat agt agt tct gca gat ttt     1296
Asp Cys Met Ser Ala Glu Leu Val Phe Asp Ser Ser Ser Ala Asp Phe
            420                 425                 430 gga ttc tcc att cca gaa cag tat gaa agg cag tac agg gac agg aac     1344
Gly Phe Ser Ile Pro Glu Gln Tyr Glu Arg Gln Tyr Arg Asp Arg Asn
        435                 440                 445 cct ggg tca att cca aat gat aac aac aga agt tct ctc gtt cct ctg     1392
Pro Gly Ser Ile Pro Asn Asp Asn Asn Arg Ser Ser Leu Val Pro Leu
    450                 455                 460 cat cca caa cct tat cgt tca agt aag cct cct cag aat gct gta gag     1440
His Pro Gln Pro Tyr Arg Ser Ser Lys Pro Pro Gln Asn Ala Val Glu
465                 470                 475                 480
```

-continued

| | |
|---|---|
| ccg acc atg aca agc cgg gat tca ttg cct tta aag cat aac cgt cct<br>Pro Thr Met Thr Ser Arg Asp Ser Leu Pro Leu Lys His Asn Arg Pro<br>                    485                        490                        495 | 1488 |
| ggt cat aga gat aca cag acc cga cta ctg att cct agc aaa cca act<br>Gly His Arg Asp Thr Gln Thr Arg Leu Leu Ile Pro Ser Lys Pro Thr<br>     500                       505                   510 | 1536 |
| aga gag ttt tcc ctt gat atg gag gat ttg gac ata tcg tgg act gat<br>Arg Glu Phe Ser Leu Asp Met Glu Asp Leu Asp Ile Ser Trp Thr Asp<br>        515                    520                   525 | 1584 |
| ctt gtt ttg aaa ggg aga att gga tca ggt tct ttt gga act gta cat<br>Leu Val Leu Lys Gly Arg Ile Gly Ser Gly Ser Phe Gly Thr Val His<br>530                      535                   540 | 1632 |
| cac gca gag tgg aat ggc tcg gag gtt gct gtg aaa att ctg atg gaa<br>His Ala Glu Trp Asn Gly Ser Glu Val Ala Val Lys Ile Leu Met Glu<br>545                    550                555                   560 | 1680 |
| caa gac ttc aaa ggt gaa cgc ttc aag gaa ttc ctg agg gag gtt gca<br>Gln Asp Phe Lys Gly Glu Arg Phe Lys Glu Phe Leu Arg Glu Val Ala<br>                    565                   570                   575 | 1728 |
| ata atg aaa ggc tta cgg cat cca aac att gtt tta ctt atg ggt gca<br>Ile Met Lys Gly Leu Arg His Pro Asn Ile Val Leu Leu Met Gly Ala<br>                580                   585                   590 | 1776 |
| gtc act aag cct cct aat tta tca att gtc acg gaa tat ttg tca agg<br>Val Thr Lys Pro Pro Asn Leu Ser Ile Val Thr Glu Tyr Leu Ser Arg<br>     595                       600                   605 | 1824 |
| ggt agc ttg tac agg ctg ttg cat aaa cct ggc gct aca gag atg ttg<br>Gly Ser Leu Tyr Arg Leu Leu His Lys Pro Gly Ala Thr Glu Met Leu<br>          610                     615                   620 | 1872 |
| gat gag aga cgt agg ctt agt atg gct tat gat gtg gct aag gga atg<br>Asp Glu Arg Arg Arg Leu Ser Met Ala Tyr Asp Val Ala Lys Gly Met<br>625                      630                   635                   640 | 1920 |
| aat tat ctt cat aaa cgc aat cct ccc att gtt cat aga gat ctg aaa<br>Asn Tyr Leu His Lys Arg Asn Pro Pro Ile Val His Arg Asp Leu Lys<br>                    645                   650                   655 | 1968 |
| tct cca aac ctt ctt gtt gac aag aaa tat aca gtg aag gtt ggt gat<br>Ser Pro Asn Leu Leu Val Asp Lys Lys Tyr Thr Val Lys Val Gly Asp<br>                660                   665                   670 | 2016 |
| ttt ggg ctt tcc cga cta aag gca aat aca ttt ctc tca tcc aag tca<br>Phe Gly Leu Ser Arg Leu Lys Ala Asn Thr Phe Leu Ser Ser Lys Ser<br>     675                       680                   685 | 2064 |
| gct gct ggg act cct gag tgg atg gct cca gaa gtt ctt cgt gac gag<br>Ala Ala Gly Thr Pro Glu Trp Met Ala Pro Glu Val Leu Arg Asp Glu<br>          690                     695                   700 | 2112 |
| cca tcc aat gag aag tca gat gtt tac agc ttt ggt gtc atc ttg tgg<br>Pro Ser Asn Glu Lys Ser Asp Val Tyr Ser Phe Gly Val Ile Leu Trp<br>705                      710                   715                   720 | 2160 |
| gag atc gca aca ttg caa cag cct tgg agt aat ttg aat cca cca cag<br>Glu Ile Ala Thr Leu Gln Gln Pro Trp Ser Asn Leu Asn Pro Pro Gln<br>                    725                   730                   735 | 2208 |
| gtt gtg gca gct gtt ggc ttt aag gga aaa aga ctt gag ata cca cgt<br>Val Val Ala Ala Val Gly Phe Lys Gly Lys Arg Leu Glu Ile Pro Arg<br>                740                   745                   750 | 2256 |
| gat tta aat cct caa tta gcc tct ata att gag tct tgt tgg gcc aat<br>Asp Leu Asn Pro Gln Leu Ala Ser Ile Ile Glu Ser Cys Trp Ala Asn<br>                    755                   760                   765 | 2304 |
| gaa ccc tgg aaa cgc cct tct ttt tca agt ata atg gat tct ttg aaa<br>Glu Pro Trp Lys Arg Pro Ser Phe Ser Ser Ile Met Asp Ser Leu Lys<br>770                      775                   780 | 2352 |
| gta ttg ctc aag ccc cct atg cct caa cct ggt cgt cca agc atg tca<br>Val Leu Leu Lys Pro Pro Met Pro Gln Pro Gly Arg Pro Ser Met Ser | 2400 |

```
                785                 790                 795                 800
tta ctg acc tga                                                                      2412
Leu Leu Thr <210> SEQ ID NO 18
<211> LENGTH: 803
<212> TYPE: PRT
<213> ORGANISM: Glycine max

<400> SEQUENCE: 18

Met Glu Met Pro Ala Arg Arg Ser Gly Asn Tyr Thr Leu Leu Ser Gln
1               5                   10                  15

Thr Pro Asp Asp Asn Leu Thr Ala Pro Leu Phe Gly Cys Ser Ser Gly
            20                  25                  30

Asp Gly Gln Ile Asn Ser Ser Lys Phe Glu Arg Val Ser Asp Trp Asp
        35                  40                  45

Ser Gly Val Glu His Arg Gln Gly Asn Arg Ile Gly Asn Leu His Ser
    50                  55                  60

Ser Phe Gly Met Gln Arg Gln Ser Ser Glu Gly Ser Phe Gly Glu Ser
65                  70                  75                  80

Ser Leu Ser Gly Glu Phe Tyr Ala Pro Thr Leu Ser Ala Ile Ala Ala
                85                  90                  95

Asn Glu Ile Asp Gly Phe Arg Gly Thr Phe Ala Gly Asn Ser Ala Ala
            100                 105                 110

Arg Ser Gly Gly Ser Ser Gly Lys Ser Trp Ala Gln Gln Thr Glu Glu
        115                 120                 125

Ser Tyr Gln Leu Gln Leu Ala Leu Ala Leu Arg Leu Ser Ser Glu Ala
    130                 135                 140

Thr Cys Ala Asp Pro Asn Phe Leu Asp Pro Val Pro Asp Glu Ser
145                 150                 155                 160

Ala Leu Arg Ser Leu Ser Ser Phe Ser Ala Glu Ala Val Ser His Arg
                165                 170                 175

Phe Trp Val Lys Gly Cys Leu Leu Tyr Phe Asp Lys Ile Pro Asp Gly
            180                 185                 190

Phe Tyr Leu Ile His Gly Met Asp Pro Tyr Val Trp Thr Val Cys Thr
        195                 200                 205

Asn Leu Gln Glu Asn Gly Arg Ile Pro Ser Leu Glu Thr Leu Lys Ser
    210                 215                 220

Ile Asn Pro Ser Asp Ser Ser Leu Glu Val Val Phe Val Asp Arg Arg
225                 230                 235                 240

Asn Asp Pro Ser Leu Arg Glu Leu Gln Asn Lys Val Gln Asp Ile Ser
                245                 250                 255

Cys Cys Cys Ile Ala Thr Thr Asp Val Val Asp Gln Leu Ala Lys Leu
            260                 265                 270

Val Cys Asn Cys Met Gly Gly Ser Ala Ser Val Trp Glu Asp Leu
        275                 280                 285

Phe Pro Ile Trp Arg Glu Arg Ile Asn Asp Leu Arg Asp Cys Leu Gly
    290                 295                 300

Ser Val Val Pro Ile Gly Ser Leu Ser Thr Gly Leu Cys Arg His
305                 310                 315                 320

Arg Ala Val Leu Phe Lys Val Leu Ala Asp Thr Ile Asp Leu Pro Cys
                325                 330                 335

Arg Ile Ala Lys Gly Cys Lys Tyr Cys Ser Arg Asp Asp Ala Ser Ser
            340                 345                 350
```

```
Cys Leu Val Arg Phe Gly Leu Asp Arg Glu Tyr Met Val Asp Leu Ile
            355                 360                 365
Gly Lys Pro Gly Cys Leu Cys Glu Pro Asp Ser Leu Val Asn Gly Pro
        370                 375                 380
Ser Ser Ile Ser Phe Ser Ser Pro Leu Cys Phe Pro Arg His Lys Pro
385                 390                 395                 400
Ala Glu Pro Thr Ile Asp Phe Arg Ser Leu Ala Lys Gln Tyr Phe Ser
                405                 410                 415
Asp Cys Met Ser Ala Glu Leu Val Phe Asp Ser Ser Ala Asp Phe
            420                 425                 430
Gly Phe Ser Ile Pro Glu Gln Tyr Glu Arg Gln Tyr Arg Asp Arg Asn
            435                 440                 445
Pro Gly Ser Ile Pro Asn Asp Asn Arg Ser Ser Leu Val Pro Leu
    450                 455                 460
His Pro Gln Pro Tyr Arg Ser Ser Lys Pro Pro Gln Asn Ala Val Glu
465                 470                 475                 480
Pro Thr Met Thr Ser Arg Asp Ser Leu Pro Leu Lys His Asn Arg Pro
                485                 490                 495
Gly His Arg Asp Thr Gln Thr Arg Leu Leu Ile Pro Ser Lys Pro Thr
            500                 505                 510
Arg Glu Phe Ser Leu Asp Met Glu Asp Leu Asp Ile Ser Trp Thr Asp
            515                 520                 525
Leu Val Leu Lys Gly Arg Ile Gly Ser Gly Ser Phe Gly Thr Val His
        530                 535                 540
His Ala Glu Trp Asn Gly Ser Glu Val Ala Val Lys Ile Leu Met Glu
545                 550                 555                 560
Gln Asp Phe Lys Gly Glu Arg Phe Lys Glu Phe Leu Arg Glu Val Ala
                565                 570                 575
Ile Met Lys Gly Leu Arg His Pro Asn Ile Val Leu Leu Met Gly Ala
            580                 585                 590
Val Thr Lys Pro Pro Asn Leu Ser Ile Val Thr Glu Tyr Leu Ser Arg
        595                 600                 605
Gly Ser Leu Tyr Arg Leu Leu His Lys Pro Gly Ala Thr Glu Met Leu
    610                 615                 620
Asp Glu Arg Arg Arg Leu Ser Met Ala Tyr Asp Val Ala Lys Gly Met
625                 630                 635                 640
Asn Tyr Leu His Lys Arg Asn Pro Pro Ile Val His Arg Asp Leu Lys
                645                 650                 655
Ser Pro Asn Leu Leu Val Asp Lys Lys Tyr Thr Val Lys Val Gly Asp
            660                 665                 670
Phe Gly Leu Ser Arg Leu Lys Ala Asn Thr Phe Leu Ser Ser Lys Ser
        675                 680                 685
Ala Ala Gly Thr Pro Glu Trp Met Ala Pro Glu Val Leu Arg Asp Glu
    690                 695                 700
Pro Ser Asn Glu Lys Ser Asp Val Tyr Ser Phe Gly Val Ile Leu Trp
705                 710                 715                 720
Glu Ile Ala Thr Leu Gln Gln Pro Trp Ser Asn Leu Asn Pro Pro Gln
                725                 730                 735
Val Val Ala Ala Val Gly Phe Lys Gly Lys Arg Leu Glu Ile Pro Arg
            740                 745                 750
Asp Leu Asn Pro Gln Leu Ala Ser Ile Ile Glu Ser Cys Trp Ala Asn
        755                 760                 765
Glu Pro Trp Lys Arg Pro Ser Phe Ser Ser Ile Met Asp Ser Leu Lys
```

-continued

```
            770               775              780
Val Leu Leu Lys Pro Pro Met Pro Gln Pro Gly Arg Pro Ser Met Ser
785                 790              795              800

Leu Leu Thr

<210> SEQ ID NO 19
<211> LENGTH: 1917
<212> TYPE: DNA
<213> ORGANISM: Glycine max
<220> FEATURE:
<221> NAME/KEY: CDS
<222> LOCATION: (1)..(1917)
<223> OTHER INFORMATION: GmEBF1a

<400> SEQUENCE: 19 atg tct aaa gtt ttc agc ttt acc gga aat gat gat ttc tac cat ggg      48
Met Ser Lys Val Phe Ser Phe Thr Gly Asn Asp Asp Phe Tyr His Gly
1               5                   10                  15 ggc cct att tat cct aac ccg aag gaa cca tgt ctc ttc ttg tct ctt      96
Gly Pro Ile Tyr Pro Asn Pro Lys Glu Pro Cys Leu Phe Leu Ser Leu
                20                  25                  30 ggc cgt caa gtt gat gtt tac ctt cct ctt cag aag agg tct cgc ttc     144
Gly Arg Gln Val Asp Val Tyr Leu Pro Leu Gln Lys Arg Ser Arg Phe
            35                  40                  45 agt gtt cca ttt gat atc agc gga gaa tgg ttt gag cag aag cag aag     192
Ser Val Pro Phe Asp Ile Ser Gly Glu Trp Phe Glu Gln Lys Gln Lys
        50                  55                  60 cca aag aca tct att gaa tct ttg cca gat gaa tgc ctc ttt gag atc     240
Pro Lys Thr Ser Ile Glu Ser Leu Pro Asp Glu Cys Leu Phe Glu Ile
65                  70                  75                  80 ctt aga agg ctg cct gca ggc caa gat agg agt gtc tgt gct tct gta     288
Leu Arg Arg Leu Pro Ala Gly Gln Asp Arg Ser Val Cys Ala Ser Val
                85                  90                  95 tcc aag cgc tgg ctt atg ctt ctg agc agt att tgc aag act gaa atc     336
Ser Lys Arg Trp Leu Met Leu Leu Ser Ser Ile Cys Lys Thr Glu Ile
                100                 105                 110 cac agc tac gga agt act gga aat gaa aac cag gaa att agt gac gaa     384
His Ser Tyr Gly Ser Thr Gly Asn Glu Asn Gln Glu Ile Ser Asp Glu
            115                 120                 125 gga tac cta tcc cga agc ttg gag gga aag aag gca aca gat gtt aga     432
Gly Tyr Leu Ser Arg Ser Leu Glu Gly Lys Lys Ala Thr Asp Val Arg
        130                 135                 140 ctt gct gcc att gcc gtt ggg aca gcc tct cga gga ggg ttg ggg aag     480
Leu Ala Ala Ile Ala Val Gly Thr Ala Ser Arg Gly Gly Leu Gly Lys
145                 150                 155                 160 ctt aca att cgt gga tgc aat tca gat cgt ggg gtg act aat gta ggt     528
Leu Thr Ile Arg Gly Cys Asn Ser Asp Arg Gly Val Thr Asn Val Gly
                165                 170                 175 ctc aag gca att gct cat ggg tgt cct tct cta aag gtt tgc tct cta     576
Leu Lys Ala Ile Ala His Gly Cys Pro Ser Leu Lys Val Cys Ser Leu
                180                 185                 190 tgg gat gtc gct act gtt ggt gat gta ggc ctg att gag att gct agt     624
Trp Asp Val Ala Thr Val Gly Asp Val Gly Leu Ile Glu Ile Ala Ser
            195                 200                 205 ggg tgc cat cag tta gag aag ctt gac cta tgc aag tgt cct aat att     672
Gly Cys His Gln Leu Glu Lys Leu Asp Leu Cys Lys Cys Pro Asn Ile
        210                 215                 220 tct gac aag act tta ata gca gtt gcg aag aac tgt ccg aat ctg gct     720
Ser Asp Lys Thr Leu Ile Ala Val Ala Lys Asn Cys Pro Asn Leu Ala
225                 230                 235                 240
```

| | | |
|---|---|---|
| gag tta tcc ata gag tca tgt ccc aac att ggt aat gaa ggt cta caa<br>Glu Leu Ser Ile Glu Ser Cys Pro Asn Ile Gly Asn Glu Gly Leu Gln<br>245 250 255 | | 768 |
| gct att ggg aag tgt ccc aat ctg agg tca atc tca atc aag aat tgc<br>Ala Ile Gly Lys Cys Pro Asn Leu Arg Ser Ile Ser Ile Lys Asn Cys<br>260 265 270 | | 816 |
| tcc ggg gtt ggt gat cag gga gtt gct ggc ctc ttg tct tca gct tct<br>Ser Gly Val Gly Asp Gln Gly Val Ala Gly Leu Leu Ser Ser Ala Ser<br>275 280 285 | | 864 |
| ttt gct cta aca aag gtg aag ctt gag tca ctg act gtt tct gat ctc<br>Phe Ala Leu Thr Lys Val Lys Leu Glu Ser Leu Thr Val Ser Asp Leu<br>290 295 300 | | 912 |
| tct cta gca gtg att ggg cat tat ggt gtt gca gtt acc gat ctt gtc<br>Ser Leu Ala Val Ile Gly His Tyr Gly Val Ala Val Thr Asp Leu Val<br>305 310 315 320 | | 960 |
| cta agt tgc ctc cca aat gtc agc gag aaa ggg ttc tgg gtt atg ggt<br>Leu Ser Cys Leu Pro Asn Val Ser Glu Lys Gly Phe Trp Val Met Gly<br>325 330 335 | | 1008 |
| aat ggc cac gga ctg cag aaa cta act tca atc aca atc aat tgc tgc<br>Asn Gly His Gly Leu Gln Lys Leu Thr Ser Ile Thr Ile Asn Cys Cys<br>340 345 350 | | 1056 |
| caa gga gtg aca gat gtt ggg ctt gaa gct att gga agg ggt tgt cca<br>Gln Gly Val Thr Asp Val Gly Leu Glu Ala Ile Gly Arg Gly Cys Pro<br>355 360 365 | | 1104 |
| aat gtg caa aac ttg aag ctt cgt aag agt gct ttt ctg tca gac aag<br>Asn Val Gln Asn Leu Lys Leu Arg Lys Ser Ala Phe Leu Ser Asp Lys<br>370 375 380 | | 1152 |
| gga tta gta tca ttt gcc agg gct gct cca tca gtt gag agc ctg caa<br>Gly Leu Val Ser Phe Ala Arg Ala Ala Pro Ser Val Glu Ser Leu Gln<br>385 390 395 400 | | 1200 |
| ttg caa gag tgc cac aga att acc caa att ggg ctc ttt ggt gtc ttt<br>Leu Gln Glu Cys His Arg Ile Thr Gln Ile Gly Leu Phe Gly Val Phe<br>405 410 415 | | 1248 |
| ttt aac tgt ggt gca aaa ttg aag gtt ctt act ctg att agc tgc tat<br>Phe Asn Cys Gly Ala Lys Leu Lys Val Leu Thr Leu Ile Ser Cys Tyr<br>420 425 430 | | 1296 |
| ggg atc aaa gat ctc aat atg gat ttg cca gca ata tct cct tct gaa<br>Gly Ile Lys Asp Leu Asn Met Asp Leu Pro Ala Ile Ser Pro Ser Glu<br>435 440 445 | | 1344 |
| tca att tgg tca tta aca atc cat gac tgc cct gga ttt ggc aat gct<br>Ser Ile Trp Ser Leu Thr Ile His Asp Cys Pro Gly Phe Gly Asn Ala<br>450 455 460 | | 1392 |
| aac ctt gcc tta ctt gga aag ctg tgt cct cgg ctt cag cat gtt gaa<br>Asn Leu Ala Leu Leu Gly Lys Leu Cys Pro Arg Leu Gln His Val Glu<br>465 470 475 480 | | 1440 |
| ttg agt gga ctt cag gga gta aca gat gca ggg ttt ctt cca ttg ctg<br>Leu Ser Gly Leu Gln Gly Val Thr Asp Ala Gly Phe Leu Pro Leu Leu<br>485 490 495 | | 1488 |
| gag agc tct gag gct ggt ctg gtt aaa gtt aat cta aat ggc tgt gta<br>Glu Ser Ser Glu Ala Gly Leu Val Lys Val Asn Leu Asn Gly Cys Val<br>500 505 510 | | 1536 |
| aat ctt tca gac aga gta gtt ttg tcc atg gtc aac tca cat gga tgg<br>Asn Leu Ser Asp Arg Val Val Leu Ser Met Val Asn Ser His Gly Trp<br>515 520 525 | | 1584 |
| act ctc gag gtg cta agc ctt gat ggt tgt aaa aga gtt ggt gat gct<br>Thr Leu Glu Val Leu Ser Leu Asp Gly Cys Lys Arg Val Gly Asp Ala<br>530 535 540 | | 1632 |
| agc ttg atg gca att gca ggc agt tgc cca ttg ctt gct gat ctc gat<br>Ser Leu Met Ala Ile Ala Gly Ser Cys Pro Leu Leu Ala Asp Leu Asp<br>545 550 555 560 | | 1680 |

```
gtt tcc agg tgt gca atc act gat aca ggt atc gca gcc ctt gca cgc      1728
Val Ser Arg Cys Ala Ile Thr Asp Thr Gly Ile Ala Ala Leu Ala Arg
                565                 570                 575 gga aag cag att aac ctt gag gta ctt tct ttg gca ggt tgt gca ttg      1776
Gly Lys Gln Ile Asn Leu Glu Val Leu Ser Leu Ala Gly Cys Ala Leu
            580                 585                 590 gtt tca gac aag agc gtg cct gcc ttg aaa aaa atg ggc tgt tcc ctt      1824
Val Ser Asp Lys Ser Val Pro Ala Leu Lys Lys Met Gly Cys Ser Leu
        595                 600                 605 gct gga tta aat atc aag cgt tgc aaa gga atc agc agc cgc tct gtc      1872
Ala Gly Leu Asn Ile Lys Arg Cys Lys Gly Ile Ser Ser Arg Ser Val
    610                 615                 620 aac aag ctt cag gaa cat ctc tgc atg tgt gac atc ctc tac tga          1917
Asn Lys Leu Gln Glu His Leu Cys Met Cys Asp Ile Leu Tyr
625                 630                 635
```

<210> SEQ ID NO 20
<211> LENGTH: 638
<212> TYPE: PRT
<213> ORGANISM: Glycine max

<400> SEQUENCE: 20

```
Met Ser Lys Val Phe Ser Phe Thr Gly Asn Asp Asp Phe Tyr His Gly
1               5                   10                  15

Gly Pro Ile Tyr Pro Asn Pro Lys Glu Pro Cys Leu Phe Leu Ser Leu
            20                  25                  30

Gly Arg Gln Val Asp Val Tyr Leu Pro Leu Gln Lys Arg Ser Arg Phe
        35                  40                  45

Ser Val Pro Phe Asp Ile Ser Gly Glu Trp Phe Glu Gln Lys Gln Lys
    50                  55                  60

Pro Lys Thr Ser Ile Glu Ser Leu Pro Asp Glu Cys Leu Phe Glu Ile
65                  70                  75                  80

Leu Arg Arg Leu Pro Ala Gly Gln Asp Arg Ser Val Cys Ala Ser Val
                85                  90                  95

Ser Lys Arg Trp Leu Met Leu Leu Ser Ser Ile Cys Lys Thr Glu Ile
            100                 105                 110

His Ser Tyr Gly Ser Thr Gly Asn Glu Asn Gln Glu Ile Ser Asp Glu
        115                 120                 125

Gly Tyr Leu Ser Arg Ser Leu Glu Gly Lys Lys Ala Thr Asp Val Arg
    130                 135                 140

Leu Ala Ala Ile Ala Val Gly Thr Ala Ser Arg Gly Leu Gly Lys
145                 150                 155                 160

Leu Thr Ile Arg Gly Cys Asn Ser Asp Arg Gly Val Thr Asn Val Gly
                165                 170                 175

Leu Lys Ala Ile Ala His Gly Cys Pro Ser Leu Lys Val Cys Ser Leu
            180                 185                 190

Trp Asp Val Ala Thr Val Gly Asp Val Gly Leu Ile Glu Ile Ala Ser
        195                 200                 205

Gly Cys His Gln Leu Glu Lys Leu Asp Leu Cys Lys Cys Pro Asn Ile
    210                 215                 220

Ser Asp Lys Thr Leu Ile Ala Val Ala Lys Asn Cys Pro Asn Leu Ala
225                 230                 235                 240

Glu Leu Ser Ile Glu Ser Cys Pro Asn Ile Gly Asn Glu Gly Leu Gln
                245                 250                 255

Ala Ile Gly Lys Cys Pro Asn Leu Arg Ser Ile Ser Ile Lys Asn Cys
            260                 265                 270
```

Ser Gly Val Gly Asp Gln Gly Val Ala Gly Leu Leu Ser Ala Ser
            275                 280                 285

Phe Ala Leu Thr Lys Val Lys Leu Glu Ser Leu Thr Val Ser Asp Leu
290                 295                 300

Ser Leu Ala Val Ile Gly His Tyr Gly Val Ala Val Thr Asp Leu Val
305                 310                 315                 320

Leu Ser Cys Leu Pro Asn Val Ser Glu Lys Gly Phe Trp Val Met Gly
                325                 330                 335

Asn Gly His Gly Leu Gln Lys Leu Thr Ser Ile Thr Ile Asn Cys Cys
            340                 345                 350

Gln Gly Val Thr Asp Val Gly Leu Glu Ala Ile Gly Arg Gly Cys Pro
        355                 360                 365

Asn Val Gln Asn Leu Lys Leu Arg Lys Ser Ala Phe Leu Ser Asp Lys
    370                 375                 380

Gly Leu Val Ser Phe Ala Arg Ala Ala Pro Ser Val Glu Ser Leu Gln
385                 390                 395                 400

Leu Gln Glu Cys His Arg Ile Thr Gln Ile Gly Leu Phe Gly Val Phe
                405                 410                 415

Phe Asn Cys Gly Ala Lys Leu Lys Val Leu Thr Leu Ile Ser Cys Tyr
            420                 425                 430

Gly Ile Lys Asp Leu Asn Met Asp Leu Pro Ala Ile Ser Pro Ser Glu
        435                 440                 445

Ser Ile Trp Ser Leu Thr Ile His Asp Cys Pro Gly Phe Gly Asn Ala
    450                 455                 460

Asn Leu Ala Leu Leu Gly Lys Leu Cys Pro Arg Leu Gln His Val Glu
465                 470                 475                 480

Leu Ser Gly Leu Gln Gly Val Thr Asp Ala Gly Phe Leu Pro Leu Leu
                485                 490                 495

Glu Ser Ser Glu Ala Gly Leu Val Lys Val Asn Leu Asn Gly Cys Val
            500                 505                 510

Asn Leu Ser Asp Arg Val Val Leu Ser Met Val Asn Ser His Gly Trp
        515                 520                 525

Thr Leu Glu Val Leu Ser Leu Asp Gly Cys Lys Arg Val Gly Asp Ala
    530                 535                 540

Ser Leu Met Ala Ile Ala Gly Ser Cys Pro Leu Leu Ala Asp Leu Asp
545                 550                 555                 560

Val Ser Arg Cys Ala Ile Thr Asp Thr Gly Ile Ala Ala Leu Ala Arg
                565                 570                 575

Gly Lys Gln Ile Asn Leu Glu Val Leu Ser Leu Ala Gly Cys Ala Leu
            580                 585                 590

Val Ser Asp Lys Ser Val Pro Ala Leu Lys Lys Met Gly Cys Ser Leu
        595                 600                 605

Ala Gly Leu Asn Ile Lys Arg Cys Lys Gly Ile Ser Ser Arg Ser Val
    610                 615                 620

Asn Lys Leu Gln Glu His Leu Cys Met Cys Asp Ile Leu Tyr
625                 630                 635

<210> SEQ ID NO 21
<211> LENGTH: 1935
<212> TYPE: DNA
<213> ORGANISM: Glycine max
<220> FEATURE:
<221> NAME/KEY: CDS
<222> LOCATION: (1)..(1935)
<223> OTHER INFORMATION: GmEBF1b

<400> SEQUENCE: 21

```
atg tcc aaa gtt ctc ggc ttt tcc gga gtt gac gat ttt tgc cct atg      48
Met Ser Lys Val Leu Gly Phe Ser Gly Val Asp Asp Phe Cys Pro Met
1               5                   10                  15 gga tca ata tac gcc aac ccc aag gaa gca agt ttc ttc ttg tcc ctt      96
Gly Ser Ile Tyr Ala Asn Pro Lys Glu Ala Ser Phe Phe Leu Ser Leu
            20                  25                  30 ggc cct caa gtt gat gta tac ttt cct cct cgg aag aga tcg cgt gtc     144
Gly Pro Gln Val Asp Val Tyr Phe Pro Pro Arg Lys Arg Ser Arg Val
        35                  40                  45 aat gct cca ttc gtt ttt gat gga gaa tgg ttc gag caa aag cag aaa     192
Asn Ala Pro Phe Val Phe Asp Gly Glu Trp Phe Glu Gln Lys Gln Lys
    50                  55                  60 acc tct att gaa gcc ttg cca gat gag tgt ctc ttt gag atc ttt aga     240
Thr Ser Ile Glu Ala Leu Pro Asp Glu Cys Leu Phe Glu Ile Phe Arg
65                  70                  75                  80 agg ttg cct gct ggc gaa gac agg agt gca tgt gcc tgt gtt tcc aag     288
Arg Leu Pro Ala Gly Glu Asp Arg Ser Ala Cys Ala Cys Val Ser Lys
                85                  90                  95 cgc tgg ctt atg ctt cta agc agt att tgc aaa agt gaa atc tct gtt     336
Arg Trp Leu Met Leu Leu Ser Ser Ile Cys Lys Ser Glu Ile Ser Val
            100                 105                 110 aac aaa aat acc aca gta gag aac cct gaa aag gag ggt gat gat gta     384
Asn Lys Asn Thr Thr Val Glu Asn Pro Glu Lys Glu Gly Asp Asp Val
        115                 120                 125 gaa ttt gga ggt aag gga tac ctc tct cga agc ttg gaa gga aag aag     432
Glu Phe Gly Gly Lys Gly Tyr Leu Ser Arg Ser Leu Glu Gly Lys Lys
    130                 135                 140 gca aca gat gtt aga ctg gct gcc ata gct gtt ggg act tca tct cga     480
Ala Thr Asp Val Arg Leu Ala Ala Ile Ala Val Gly Thr Ser Ser Arg
145                 150                 155                 160 gga gga ttg ggg aag ctc tca atc cgt gga agc aac atg gtt cgt ggg     528
Gly Gly Leu Gly Lys Leu Ser Ile Arg Gly Ser Asn Met Val Arg Gly
                165                 170                 175 gtg act agt cat ggt ctc aag gct gtt gct cgt gga tgc cct tct ttg     576
Val Thr Ser His Gly Leu Lys Ala Val Ala Arg Gly Cys Pro Ser Leu
            180                 185                 190 aag gct ctt tct cta tgg aat gtt gct acc gtt ggt gat gag ggc cta     624
Lys Ala Leu Ser Leu Trp Asn Val Ala Thr Val Gly Asp Glu Gly Leu
        195                 200                 205 att gag att gct aat gga tgc cac cag cta gag aag ctt gat ctt tgc     672
Ile Glu Ile Ala Asn Gly Cys His Gln Leu Glu Lys Leu Asp Leu Cys
    210                 215                 220 aag tgc cct gca att act gat aag gct ttg gtt gca att gca aag aac     720
Lys Cys Pro Ala Ile Thr Asp Lys Ala Leu Val Ala Ile Ala Lys Asn
225                 230                 235                 240 tgc cag aat ctg act gag ttg tca ttt gaa tct tgc cct aac att ggt     768
Cys Gln Asn Leu Thr Glu Leu Ser Phe Glu Ser Cys Pro Asn Ile Gly
                245                 250                 255 aat gaa ggt cta cga gct att ggg aag ttg tgc tcc aat ctg aag tcc     816
Asn Glu Gly Leu Arg Ala Ile Gly Lys Leu Cys Ser Asn Leu Lys Ser
            260                 265                 270 ata tcc atc aag gac tgc act ggt gtt agt gat cac gga att gct gga     864
Ile Ser Ile Lys Asp Cys Thr Gly Val Ser Asp His Gly Ile Ala Gly
        275                 280                 285 ttg ctt tct tca act tct ttg gtt cta tca aag gtg aag ctc cag gca     912
Leu Leu Ser Ser Thr Ser Leu Val Leu Ser Lys Val Lys Leu Gln Ala
    290                 295                 300
```

| | | |
|---|---|---|
| ttg act gtt tca gat ctc tct cta gct gtt att ggt cat tat ggc aag<br>Leu Thr Val Ser Asp Leu Ser Leu Ala Val Ile Gly His Tyr Gly Lys<br>305                     310                     315                  320 | 960 |
| tca gtt act gat ctt gtc ctt aat tgc ctc cca aat gtc agc gag agg<br>Ser Val Thr Asp Leu Val Leu Asn Cys Leu Pro Asn Val Ser Glu Arg<br>                   325                   330                   335 | 1008 |
| ggg ttc tgg gtc atg ggt aat ggt aat gga ttg cag aag cta aaa tca<br>Gly Phe Trp Val Met Gly Asn Gly Asn Gly Leu Gln Lys Leu Lys Ser<br>                340                     345                   350 | 1056 |
| ctt aca gtt gca tct tgc aga gga gta aca gat att ggg ctt gaa gct<br>Leu Thr Val Ala Ser Cys Arg Gly Val Thr Asp Ile Gly Leu Glu Ala<br>          355                     360                   365 | 1104 |
| gtt gga aag ggt tgt cca aat ctg aaa att gca cac ctt cac aag tgt<br>Val Gly Lys Gly Cys Pro Asn Leu Lys Ile Ala His Leu His Lys Cys<br>370                     375                     380 | 1152 |
| gca ttt ctg tca gac aat ggg ttg ata tca ttt gcc aag gct gct tca<br>Ala Phe Leu Ser Asp Asn Gly Leu Ile Ser Phe Ala Lys Ala Ala Ser<br>385                     390                     395                  400 | 1200 |
| tca ctt gag agc cta cga ttg gaa gag tgc cac cga att acc caa ctt<br>Ser Leu Glu Ser Leu Arg Leu Glu Glu Cys His Arg Ile Thr Gln Leu<br>                     405                   410                   415 | 1248 |
| ggg ttt ttt ggt gtc ctt ttt aac tgt ggt gca aaa ttg aag gct atc<br>Gly Phe Phe Gly Val Leu Phe Asn Cys Gly Ala Lys Leu Lys Ala Ile<br>                420                     425                   430 | 1296 |
| tct ttg gtg agc tgc tac ggg atc aaa gat ctg aac ttg gtg ttg cca<br>Ser Leu Val Ser Cys Tyr Gly Ile Lys Asp Leu Asn Leu Val Leu Pro<br>          435                     440                   445 | 1344 |
| aca gta tct cca tgt gaa tca ctt cgg tct tta tct atc agt aat tgc<br>Thr Val Ser Pro Cys Glu Ser Leu Arg Ser Leu Ser Ile Ser Asn Cys<br>450                     455                     460 | 1392 |
| cct gga ttt ggc aat gcc tcc ctc tct gta ttg gga aag ctg tgc cct<br>Pro Gly Phe Gly Asn Ala Ser Leu Ser Val Leu Gly Lys Leu Cys Pro<br>465                     470                     475                  480 | 1440 |
| cag ctt cag cat gtt gaa ttg agt gga ctc gag gga gtg aca gat gca<br>Gln Leu Gln His Val Glu Leu Ser Gly Leu Glu Gly Val Thr Asp Ala<br>                     485                   490                   495 | 1488 |
| ggg ctt ctt cca ctc ctt gag agt tcc gag gct ggt ttg gtt aaa gtg<br>Gly Leu Leu Pro Leu Leu Glu Ser Ser Glu Ala Gly Leu Val Lys Val<br>                500                     505                   510 | 1536 |
| aac ctt agt ggg tgc aca aac gtt acc aat aaa gta gtt tcg tcc ttg<br>Asn Leu Ser Gly Cys Thr Asn Val Thr Asn Lys Val Val Ser Ser Leu<br>          515                     520                   525 | 1584 |
| gcc aat ctg cat ggt tgg act ctt gag aat cta aac ctt gat ggt tgc<br>Ala Asn Leu His Gly Trp Thr Leu Glu Asn Leu Asn Leu Asp Gly Cys<br>530                     535                     540 | 1632 |
| aaa aac atc agt gat gct agc ttg atg gca att gct gaa aac tgt gca<br>Lys Asn Ile Ser Asp Ala Ser Leu Met Ala Ile Ala Glu Asn Cys Ala<br>545                     550                     555                  560 | 1680 |
| ttg cta tgt gat ctc gat gtc tcc aag tgt gct ata acc gat gct ggg<br>Leu Leu Cys Asp Leu Asp Val Ser Lys Cys Ala Ile Thr Asp Ala Gly<br>                     565                   570                   575 | 1728 |
| att gaa gcc ctg gca cat gct aaa cag att aat ctg caa gtt ctt tct<br>Ile Glu Ala Leu Ala His Ala Lys Gln Ile Asn Leu Gln Val Leu Ser<br>                580                     585                   590 | 1776 |
| ttg tca ggt tgc act ttg gtc tca gac agg agc ttg cct gcg ttg aga<br>Leu Ser Gly Cys Thr Leu Val Ser Asp Arg Ser Leu Pro Ala Leu Arg<br>          595                     600                   605 | 1824 |
| gaa ttg ggt cac acc ctt ttg gga cta aac atc cag cac tgc aat gca<br>Glu Leu Gly His Thr Leu Leu Gly Leu Asn Ile Gln His Cys Asn Ala<br>610                     615                     620 | 1872 |

```
atc aac agc agt acg gtt gac aca ctt gtg gag ctt ctc tgg agg tgt    1920
Ile Asn Ser Ser Thr Val Asp Thr Leu Val Glu Leu Leu Trp Arg Cys
625                 630                 635                 640 gac atc ctc tcc tga                                                 1935
Asp Ile Leu Ser
```

<210> SEQ ID NO 22
<211> LENGTH: 644
<212> TYPE: PRT
<213> ORGANISM: Glycine max

<400> SEQUENCE: 22

```
Met Ser Lys Val Leu Gly Phe Ser Gly Val Asp Asp Phe Cys Pro Met
1               5                   10                  15

Gly Ser Ile Tyr Ala Asn Pro Lys Glu Ala Ser Phe Phe Leu Ser Leu
            20                  25                  30

Gly Pro Gln Val Asp Val Tyr Phe Pro Arg Lys Arg Ser Arg Val
        35                  40                  45

Asn Ala Pro Phe Val Phe Asp Gly Glu Trp Phe Glu Gln Lys Gln Lys
50                  55                  60

Thr Ser Ile Glu Ala Leu Pro Asp Glu Cys Leu Phe Glu Ile Phe Arg
65                  70                  75                  80

Arg Leu Pro Ala Gly Glu Asp Arg Ser Ala Cys Ala Cys Val Ser Lys
                85                  90                  95

Arg Trp Leu Met Leu Leu Ser Ser Ile Cys Lys Ser Glu Ile Ser Val
            100                 105                 110

Asn Lys Asn Thr Thr Val Glu Asn Pro Glu Lys Glu Gly Asp Asp Val
        115                 120                 125

Glu Phe Gly Gly Lys Gly Tyr Leu Ser Arg Ser Leu Glu Gly Lys Lys
130                 135                 140

Ala Thr Asp Val Arg Leu Ala Ala Ile Ala Val Gly Thr Ser Ser Arg
145                 150                 155                 160

Gly Gly Leu Gly Lys Leu Ser Ile Arg Gly Ser Asn Met Val Arg Gly
                165                 170                 175

Val Thr Ser His Gly Leu Lys Ala Val Ala Arg Gly Cys Pro Ser Leu
            180                 185                 190

Lys Ala Leu Ser Leu Trp Asn Val Ala Thr Val Gly Asp Glu Gly Leu
        195                 200                 205

Ile Glu Ile Ala Asn Gly Cys His Gln Leu Glu Lys Leu Asp Leu Cys
210                 215                 220

Lys Cys Pro Ala Ile Thr Asp Lys Ala Leu Val Ala Ile Ala Lys Asn
225                 230                 235                 240

Cys Gln Asn Leu Thr Glu Leu Ser Phe Glu Ser Cys Pro Asn Ile Gly
                245                 250                 255

Asn Glu Gly Leu Arg Ala Ile Gly Lys Leu Cys Ser Asn Leu Lys Ser
            260                 265                 270

Ile Ser Ile Lys Asp Cys Thr Gly Val Ser Asp His Gly Ile Ala Gly
        275                 280                 285

Leu Leu Ser Ser Thr Ser Leu Val Leu Ser Lys Val Lys Leu Gln Ala
290                 295                 300

Leu Thr Val Ser Asp Leu Ser Leu Ala Val Ile Gly His Tyr Gly Lys
305                 310                 315                 320

Ser Val Thr Asp Leu Val Leu Asn Cys Leu Pro Asn Val Ser Glu Arg
                325                 330                 335
```

```
Gly Phe Trp Val Met Gly Asn Gly Asn Gly Leu Gln Lys Leu Lys Ser
                340                 345                 350

Leu Thr Val Ala Ser Cys Arg Gly Val Thr Asp Ile Gly Leu Glu Ala
            355                 360                 365

Val Gly Lys Gly Cys Pro Asn Leu Lys Ile Ala His Leu His Lys Cys
    370                 375                 380

Ala Phe Leu Ser Asp Asn Gly Leu Ile Ser Phe Ala Lys Ala Ala Ser
385                 390                 395                 400

Ser Leu Glu Ser Leu Arg Leu Glu Glu Cys His Arg Ile Thr Gln Leu
                405                 410                 415

Gly Phe Phe Gly Val Leu Phe Asn Cys Gly Ala Lys Leu Lys Ala Ile
            420                 425                 430

Ser Leu Val Ser Cys Tyr Gly Ile Lys Asp Leu Asn Leu Val Leu Pro
        435                 440                 445

Thr Val Ser Pro Cys Glu Ser Leu Arg Ser Leu Ser Ile Ser Asn Cys
    450                 455                 460

Pro Gly Phe Gly Asn Ala Ser Leu Ser Val Leu Gly Lys Leu Cys Pro
465                 470                 475                 480

Gln Leu Gln His Val Glu Leu Ser Gly Leu Glu Gly Val Thr Asp Ala
                485                 490                 495

Gly Leu Leu Pro Leu Leu Glu Ser Ser Glu Ala Gly Leu Val Lys Val
            500                 505                 510

Asn Leu Ser Gly Cys Thr Asn Val Thr Asn Lys Val Val Ser Ser Leu
        515                 520                 525

Ala Asn Leu His Gly Trp Thr Leu Glu Asn Leu Asn Leu Asp Gly Cys
    530                 535                 540

Lys Asn Ile Ser Asp Ala Ser Leu Met Ala Ile Ala Glu Asn Cys Ala
545                 550                 555                 560

Leu Leu Cys Asp Leu Asp Val Ser Lys Cys Ala Ile Thr Asp Ala Gly
                565                 570                 575

Ile Glu Ala Leu Ala His Ala Lys Gln Ile Asn Leu Gln Val Leu Ser
            580                 585                 590

Leu Ser Gly Cys Thr Leu Val Ser Asp Arg Ser Leu Pro Ala Leu Arg
        595                 600                 605

Glu Leu Gly His Thr Leu Leu Gly Leu Asn Ile Gln His Cys Asn Ala
    610                 615                 620

Ile Asn Ser Ser Thr Val Asp Thr Leu Val Glu Leu Leu Trp Arg Cys
625                 630                 635                 640

Asp Ile Leu Ser

<210> SEQ ID NO 23
<211> LENGTH: 1917
<212> TYPE: DNA
<213> ORGANISM: Glycine max
<220> FEATURE:
<221> NAME/KEY: CDS
<222> LOCATION: (1)..(1917)
<223> OTHER INFORMATION: GmEBF1c

<400> SEQUENCE: 23 atg cct gcc ctt gtc aat tac agt ggt gat gat gaa ctg tac cct ggg      48
Met Pro Ala Leu Val Asn Tyr Ser Gly Asp Asp Glu Leu Tyr Pro Gly
1               5                   10                  15 ggt tct ttt tgc cca aat cca atg gag ttg ggt cgc ttg tac act act      96
Gly Ser Phe Cys Pro Asn Pro Met Glu Leu Gly Arg Leu Tyr Thr Thr
            20                  25                  30
```

| | | | | | | | | | | | | | | | | |
|---|---|---|---|---|---|---|---|---|---|---|---|---|---|---|---|---|
| att | ggc | tcc | aat | ttg | gat | atg | tac | tac | cct | cct | act | aag | aga | cca | cgc | 144 |
| Ile | Gly | Ser | Asn | Leu | Asp | Met | Tyr | Tyr | Pro | Pro | Thr | Lys | Arg | Pro | Arg | |
| | | 35 | | | | 40 | | | | | 45 | | | | | |
| tcc | atc | ttt | gaa | gct | att | gag | cgt | gag | cag | tat | tat | caa | gac | cct | ggt | 192 |
| Ser | Ile | Phe | Glu | Ala | Ile | Glu | Arg | Glu | Gln | Tyr | Tyr | Gln | Asp | Pro | Gly | |
| | 50 | | | | | 55 | | | | | 60 | | | | | |
| att | gag | gtt | ctt | cca | gat | gaa | tgc | ctc | ttt | gag | ata | ttc | aga | cgc | ctc | 240 |
| Ile | Glu | Val | Leu | Pro | Asp | Glu | Cys | Leu | Phe | Glu | Ile | Phe | Arg | Arg | Leu | |
| 65 | | | | | 70 | | | | | 75 | | | | | 80 | |
| cct | agt | ggc | aaa | gag | aga | agc | tca | tgt | gcc | tgt | gta | tct | aaa | cgg | tgg | 288 |
| Pro | Ser | Gly | Lys | Glu | Arg | Ser | Ser | Cys | Ala | Cys | Val | Ser | Lys | Arg | Trp | |
| | | | | 85 | | | | 90 | | | | | 95 | | | |
| ctt | atg | ctt | atg | agc | act | atc | tgt | aaa | gat | gag | att | gag | ggg | act | act | 336 |
| Leu | Met | Leu | Met | Ser | Thr | Ile | Cys | Lys | Asp | Glu | Ile | Glu | Gly | Thr | Thr | |
| | | | 100 | | | | | 105 | | | | | 110 | | | |
| tct | gtt | gct | gaa | act | gtt | tct | tct | gat | gag | aat | caa | gat | att | gat | gat | 384 |
| Ser | Val | Ala | Glu | Thr | Val | Ser | Ser | Asp | Glu | Asn | Gln | Asp | Ile | Asp | Asp | |
| | | | 115 | | | | 120 | | | | | 125 | | | | |
| gat | ggc | tac | ctt | aca | agg | tgt | cta | gat | ggg | aag | aaa | gcc | act | gat | gtg | 432 |
| Asp | Gly | Tyr | Leu | Thr | Arg | Cys | Leu | Asp | Gly | Lys | Lys | Ala | Thr | Asp | Val | |
| | 130 | | | | | 135 | | | | | 140 | | | | | |
| agg | ctt | gct | gca | att | gca | gtt | ggg | act | agt | agc | cgt | ggc | ggt | cta | ggg | 480 |
| Arg | Leu | Ala | Ala | Ile | Ala | Val | Gly | Thr | Ser | Ser | Arg | Gly | Gly | Leu | Gly | |
| 145 | | | | | 150 | | | | | 155 | | | | | 160 | |
| aag | ctt | tca | atc | aga | gga | agc | aac | tct | gag | cgt | ggt | gtc | aca | aac | ctt | 528 |
| Lys | Leu | Ser | Ile | Arg | Gly | Ser | Asn | Ser | Glu | Arg | Gly | Val | Thr | Asn | Leu | |
| | | | | 165 | | | | | 170 | | | | | 175 | | |
| ggc | ctc | tct | gca | gtt | gct | cat | ggt | tgc | cct | tct | ctc | aga | tca | ctt | tct | 576 |
| Gly | Leu | Ser | Ala | Val | Ala | His | Gly | Cys | Pro | Ser | Leu | Arg | Ser | Leu | Ser | |
| | | | 180 | | | | | 185 | | | | | 190 | | | |
| tta | tgg | aat | gta | tct | acc | att | ggg | gat | gag | ggt | ctg | tct | cag | gta | gca | 624 |
| Leu | Trp | Asn | Val | Ser | Thr | Ile | Gly | Asp | Glu | Gly | Leu | Ser | Gln | Val | Ala | |
| | | 195 | | | | | 200 | | | | | 205 | | | | |
| aaa | gga | tgt | cat | atg | ttg | gag | aag | ctt | gac | ttg | tgt | cat | tgt | tcc | tca | 672 |
| Lys | Gly | Cys | His | Met | Leu | Glu | Lys | Leu | Asp | Leu | Cys | His | Cys | Ser | Ser | |
| | 210 | | | | | 215 | | | | | 220 | | | | | |
| atc | agc | aac | aag | ggt | ttg | att | gca | ata | gct | gaa | ggt | tgc | ccc | aac | ttg | 720 |
| Ile | Ser | Asn | Lys | Gly | Leu | Ile | Ala | Ile | Ala | Glu | Gly | Cys | Pro | Asn | Leu | |
| 225 | | | | | 230 | | | | | 235 | | | | | 240 | |
| acc | acc | tta | act | att | gaa | tca | tgc | cca | aat | att | gga | aat | gaa | ggc | ttg | 768 |
| Thr | Thr | Leu | Thr | Ile | Glu | Ser | Cys | Pro | Asn | Ile | Gly | Asn | Glu | Gly | Leu | |
| | | | | 245 | | | | | 250 | | | | | 255 | | |
| caa | gct | act | gca | agg | cta | tgc | ccc | aag | ctg | cag | tcc | atc | tca | atc | aag | 816 |
| Gln | Ala | Thr | Ala | Arg | Leu | Cys | Pro | Lys | Leu | Gln | Ser | Ile | Ser | Ile | Lys | |
| | | | 260 | | | | | 265 | | | | | 270 | | | |
| gat | tgc | cct | ctt | gtt | ggg | gat | cat | gga | gtg | tct | agt | ctt | ttg | gca | tcg | 864 |
| Asp | Cys | Pro | Leu | Val | Gly | Asp | His | Gly | Val | Ser | Ser | Leu | Leu | Ala | Ser | |
| | | 275 | | | | | 280 | | | | | 285 | | | | |
| gct | tca | aat | tta | tca | agg | gtt | aag | ctt | cag | act | ttg | aac | atc | aca | gat | 912 |
| Ala | Ser | Asn | Leu | Ser | Arg | Val | Lys | Leu | Gln | Thr | Leu | Asn | Ile | Thr | Asp | |
| | 290 | | | | | 295 | | | | | 300 | | | | | |
| ttc | tct | ttg | gct | gtt | att | tgc | cat | tat | gga | aaa | gcg | ata | aca | aat | ctg | 960 |
| Phe | Ser | Leu | Ala | Val | Ile | Cys | His | Tyr | Gly | Lys | Ala | Ile | Thr | Asn | Leu | |
| 305 | | | | | 310 | | | | | 315 | | | | | 320 | |
| gtc | ctc | tct | ggt | cta | aaa | aat | gta | act | gaa | agg | ggg | ttc | tgg | gtc | atg | 1008 |
| Val | Leu | Ser | Gly | Leu | Lys | Asn | Val | Thr | Glu | Arg | Gly | Phe | Trp | Val | Met | |
| | | | | 325 | | | | | 330 | | | | | 335 | | |
| ggg | gct | gct | caa | ggt | ctg | cag | aaa | cta | ctg | tca | ctt | act | gtt | act | gcc | 1056 |
| Gly | Ala | Ala | Gln | Gly | Leu | Gln | Lys | Leu | Leu | Ser | Leu | Thr | Val | Thr | Ala | |
| | | | | 340 | | | | | 345 | | | | | 350 | | |

-continued

```
tgc agg ggg gta act gat aca agc att gaa gcc att ggt aaa ggt tgc      1104
Cys Arg Gly Val Thr Asp Thr Ser Ile Glu Ala Ile Gly Lys Gly Cys
        355                 360                 365 atc aac ctg aag cac ttg tgc ctt cgc cgg tgt tgt ttt gtg tct gac      1152
Ile Asn Leu Lys His Leu Cys Leu Arg Arg Cys Cys Phe Val Ser Asp
370                 375                 380 aat gga ttg gta gca ttt gcc aaa gct gca ata tct ctt gaa agt ttg      1200
Asn Gly Leu Val Ala Phe Ala Lys Ala Ala Ile Ser Leu Glu Ser Leu
385                 390                 395                 400 cag ctg gag gag tgc aac agg ttc act cag tct agg att att gtt gcc      1248
Gln Leu Glu Glu Cys Asn Arg Phe Thr Gln Ser Arg Ile Ile Val Ala
                405                 410                 415 ctt gca gac atc aaa acg aag ttg aaa tct ctt gcc ctt gtg aag tgc      1296
Leu Ala Asp Ile Lys Thr Lys Leu Lys Ser Leu Ala Leu Val Lys Cys
        420                 425                 430 atg gga gtc aaa gat atc gat atg gaa gtg tct atg ctt tct cca tgc      1344
Met Gly Val Lys Asp Ile Asp Met Glu Val Ser Met Leu Ser Pro Cys
            435                 440                 445 gag tct ctt caa tct tta gcc att caa aag tgc cct ggt ttt ggt agt      1392
Glu Ser Leu Gln Ser Leu Ala Ile Gln Lys Cys Pro Gly Phe Gly Ser
450                 455                 460 gct agc ctg gcc acg att gga aaa ttg tgt ccc caa ctt cag cat ctt      1440
Ala Ser Leu Ala Thr Ile Gly Lys Leu Cys Pro Gln Leu Gln His Leu
465                 470                 475                 480 aat ctg act gga ctc tat ggc ata act gat gct ggc ctt ctc ccc ctt      1488
Asn Leu Thr Gly Leu Tyr Gly Ile Thr Asp Ala Gly Leu Leu Pro Leu
                485                 490                 495 ttg gag aat tgt gag gct gga ctt gtc aat gta aac ctc act ggt tgc      1536
Leu Glu Asn Cys Glu Ala Gly Leu Val Asn Val Asn Leu Thr Gly Cys
                500                 505                 510 tgg aac ttg aca gat aat ata gtt tca gcc ttg gcc agg cta cat ggt      1584
Trp Asn Leu Thr Asp Asn Ile Val Ser Ala Leu Ala Arg Leu His Gly
        515                 520                 525 gga acc ctc gaa gta cta aat ctt gat gga tgc tgg aaa att act gat      1632
Gly Thr Leu Glu Val Leu Asn Leu Asp Gly Cys Trp Lys Ile Thr Asp
530                 535                 540 gca agc ttg gtt gca att gca aac aac ttc cta gtg ctt aat gat cta      1680
Ala Ser Leu Val Ala Ile Ala Asn Asn Phe Leu Val Leu Asn Asp Leu
545                 550                 555                 560 gat gtg tca aag tgt gca atc acc gat gcc ggt gta gct gtt ctc tca      1728
Asp Val Ser Lys Cys Ala Ile Thr Asp Ala Gly Val Ala Val Leu Ser
                565                 570                 575 agg gcc agt ctg cct agc ttg caa gtg ctt tcg ttg tct ggt tgt tct      1776
Arg Ala Ser Leu Pro Ser Leu Gln Val Leu Ser Leu Ser Gly Cys Ser
                580                 585                 590 gat gta tca aac aag agt gcg cct ttc ctg aca aaa ttg ggc cag acc      1824
Asp Val Ser Asn Lys Ser Ala Pro Phe Leu Thr Lys Leu Gly Gln Thr
            595                 600                 605 ttg ctg gga ttg aat ctt caa aac tgc aat tca att ggc agc agc aca      1872
Leu Leu Gly Leu Asn Leu Gln Asn Cys Asn Ser Ile Gly Ser Ser Thr
610                 615                 620 atg gag ttg cta gtg gag aag ttg tgg aga tgt gat att ctg gct           1917
Met Glu Leu Leu Val Glu Lys Leu Trp Arg Cys Asp Ile Leu Ala
625                 630                 635
```

<210> SEQ ID NO 24
<211> LENGTH: 639
<212> TYPE: PRT
<213> ORGANISM: Glycine max

<400> SEQUENCE: 24

```
Met Pro Ala Leu Val Asn Tyr Ser Gly Asp Asp Glu Leu Tyr Pro Gly
1               5                   10                  15
Gly Ser Phe Cys Pro Asn Pro Met Glu Leu Gly Arg Leu Tyr Thr Thr
            20                  25                  30
Ile Gly Ser Asn Leu Asp Met Tyr Tyr Pro Pro Thr Lys Arg Pro Arg
        35                  40                  45
Ser Ile Phe Glu Ala Ile Glu Arg Glu Gln Tyr Tyr Gln Asp Pro Gly
    50                  55                  60
Ile Glu Val Leu Pro Asp Glu Cys Leu Phe Glu Ile Phe Arg Arg Leu
65                  70                  75                  80
Pro Ser Gly Lys Glu Arg Ser Cys Ala Cys Val Ser Lys Arg Trp
                85                  90                  95
Leu Met Leu Met Ser Thr Ile Cys Lys Asp Glu Ile Glu Gly Thr Thr
                100                 105                 110
Ser Val Ala Glu Thr Val Ser Ser Asp Glu Asn Gln Asp Ile Asp Asp
            115                 120                 125
Asp Gly Tyr Leu Thr Arg Cys Leu Asp Gly Lys Lys Ala Thr Asp Val
        130                 135                 140
Arg Leu Ala Ala Ile Ala Val Gly Thr Ser Ser Arg Gly Gly Leu Gly
145                 150                 155                 160
Lys Leu Ser Ile Arg Gly Ser Asn Ser Glu Arg Gly Val Thr Asn Leu
                165                 170                 175
Gly Leu Ser Ala Val Ala His Gly Cys Pro Ser Leu Arg Ser Leu Ser
            180                 185                 190
Leu Trp Asn Val Ser Thr Ile Gly Asp Glu Gly Leu Ser Gln Val Ala
        195                 200                 205
Lys Gly Cys His Met Leu Glu Lys Leu Asp Leu Cys His Cys Ser Ser
210                 215                 220
Ile Ser Asn Lys Gly Leu Ile Ala Ile Ala Glu Gly Cys Pro Asn Leu
225                 230                 235                 240
Thr Thr Leu Thr Ile Glu Ser Cys Pro Asn Ile Gly Asn Glu Gly Leu
                245                 250                 255
Gln Ala Thr Ala Arg Leu Cys Pro Lys Leu Gln Ser Ile Ser Ile Lys
            260                 265                 270
Asp Cys Pro Leu Val Gly Asp His Gly Val Ser Ser Leu Leu Ala Ser
        275                 280                 285
Ala Ser Asn Leu Ser Arg Val Lys Leu Gln Thr Leu Asn Ile Thr Asp
    290                 295                 300
Phe Ser Leu Ala Val Ile Cys His Tyr Gly Lys Ala Ile Thr Asn Leu
305                 310                 315                 320
Val Leu Ser Gly Leu Lys Asn Val Thr Glu Arg Gly Phe Trp Val Met
                325                 330                 335
Gly Ala Ala Gln Gly Leu Gln Lys Leu Leu Ser Leu Thr Val Thr Ala
            340                 345                 350
Cys Arg Gly Val Thr Asp Thr Ser Ile Glu Ala Ile Gly Lys Gly Cys
        355                 360                 365
Ile Asn Leu Lys His Leu Cys Leu Arg Arg Cys Cys Phe Val Ser Asp
    370                 375                 380
Asn Gly Leu Val Ala Phe Ala Lys Ala Ala Ile Ser Leu Glu Ser Leu
385                 390                 395                 400
Gln Leu Glu Glu Cys Asn Arg Phe Thr Gln Ser Arg Ile Ile Val Ala
                405                 410                 415
```

Leu Ala Asp Ile Lys Thr Lys Leu Lys Ser Leu Ala Leu Val Lys Cys
            420                 425                 430

Met Gly Val Lys Asp Ile Asp Met Glu Val Ser Met Leu Ser Pro Cys
            435                 440                 445

Glu Ser Leu Gln Ser Leu Ala Ile Gln Lys Cys Pro Gly Phe Gly Ser
450                 455                 460

Ala Ser Leu Ala Thr Ile Gly Lys Leu Cys Pro Gln Leu Gln His Leu
465                 470                 475                 480

Asn Leu Thr Gly Leu Tyr Gly Ile Thr Asp Ala Gly Leu Leu Pro Leu
                485                 490                 495

Leu Glu Asn Cys Glu Ala Gly Leu Val Asn Val Asn Leu Thr Gly Cys
            500                 505                 510

Trp Asn Leu Thr Asp Asn Ile Val Ser Ala Leu Ala Arg Leu His Gly
            515                 520                 525

Gly Thr Leu Glu Val Leu Asn Leu Asp Gly Cys Trp Lys Ile Thr Asp
530                 535                 540

Ala Ser Leu Val Ala Ile Ala Asn Asn Phe Leu Val Leu Asn Asp Leu
545                 550                 555                 560

Asp Val Ser Lys Cys Ala Ile Thr Asp Ala Gly Val Ala Val Leu Ser
                565                 570                 575

Arg Ala Ser Leu Pro Ser Leu Gln Val Leu Ser Leu Ser Gly Cys Ser
            580                 585                 590

Asp Val Ser Asn Lys Ser Ala Pro Phe Leu Thr Lys Leu Gly Gln Thr
            595                 600                 605

Leu Leu Gly Leu Asn Leu Gln Asn Cys Asn Ser Ile Gly Ser Ser Thr
610                 615                 620

Met Glu Leu Leu Val Glu Lys Leu Trp Arg Cys Asp Ile Leu Ala
625                 630                 635

<210> SEQ ID NO 25
<211> LENGTH: 528
<212> TYPE: DNA
<213> ORGANISM: artificial
<220> FEATURE:
<223> OTHER INFORMATION: synthetic sequence

<400> SEQUENCE: 25
ttatgcttta ttggtggtgg atactttccc agagttgagt ctacaatgtt ctgaggagcg      60
ttacatgatt gatatgtttc agaaccttgt tcacgtgagc ttggatgaga atcttgcgga     120
tgcagaggaa ggtgagaact tctattgcta tcagacgaaa ttggcctagg gttactgctg     180
tctttgcact tcccatcaaa ctgttctgca gagttgttgt cgaagacaag ctcaagagac     240
acacaatccg agaaatactg tttggccaat gacctgaaat caatggtagg ttcagccggt     300
ttacttcgac aacaactctg cagaacagtt tgatgggaag tgcaaagaca gcagtaaccc     360
taggccaatt tcgtctgata gcaatagaag ttctcacctt cctctgcatc cgcaagattc     420
tcatccaagc tcacgtgaac aaggttctga acatatcaa tcatgtaacg ctcctcagaa      480
cattgtagac tcaactctgg aaagtatcc accaccaata aagcataa                   528

<210> SEQ ID NO 26
<211> LENGTH: 759
<212> TYPE: DNA
<213> ORGANISM: Artificial
<220> FEATURE:
<223> OTHER INFORMATION: Synthetic Sequence

<400> SEQUENCE: 26

```
ctcctccgtc tgctgcgccc agctcttccc ggaggaggag ccggcgatcc tcgccggcgc      60
cgcctccgag aacttgcttc gctcgtcgtg gaggtagccg aaggcgtcga cgtcgctggc     120
cgccgccgtg gagatcgtcg gagcgtagaa gtcgccgccg ccggagagcg agctctcgcc     180
gtagctgctc ccgctggact ggcgctgcag gcctatcgag gagtagacgt ttccgatccg     240
gttggcggcc cggtgatcag cgacgaggtc ccattcgaag gcggcacggt cggactttcc     300
ggcacggccg gccttgccgt cgccggagga tgagggagcg gcggcggagg agaactggtc     360
gtcgggaatt tggctgagga gcgaatagtt ggatcttctg gcaggcattt ccatgccgcc     420
gctccctcat cctccggcga cggcaaggcc ggccgtgccg gaaagtccga ccgtgccgcc     480
ttcgaatggg acctcgtcgc tgatcaccgg gccgccaacc ggatcggaaa cgtctactcc     540
tcgataggcc tgcagcgcca gtccagcggg agcagctacg gcgagagctc gctctccggc     600
ggcggcgact tctacgctcc gacgatctcc acggcggcgg ccagcgacgt cgacgccttc     660
ggctacctcc acgacgagcg aagcaagttc tcggaggcgg cgccggcgag gatcgccggc     720
tcctcctccg ggaagagctg ggcgcagcag acggaggag                            759
```

<210> SEQ ID NO 27
<211> LENGTH: 522
<212> TYPE: DNA
<213> ORGANISM: Artificial
<220> FEATURE:
<223> OTHER INFORMATION: Synthetic Sequence

<400> SEQUENCE: 27

```
acggttatgc tttaaaggca atgaatcccg gcttgtcatg gtcggctcta cagcattctg      60
aggaggctta cttgaacgat aaggttgtgg atgcagagga acgagagaac ttctgttgtt     120
atcatttgga attgacccag ggttcctgtc cctgtactgc ctttcatact gttctggaat     180
ggagaatcca aaatctgcag aactactatc gaagacaagc tcagcagaca tacaatccga     240
gaaatattgt ttggccagtg acctgaaatc aatggtaggt tcagctggtt tatgtctgct     300
gagcttgtct tcgatagtag ttctgcagat tttggattct ccattccaga acagtatgaa     360
aggcagtaca gggacaggaa ccctgggtca attccaaatg ataacaacag aagttctctc     420
gttcctctgc atccacaacc ttatcgttca agtaagcctc ctcagaatgc tgtagagccg     480
accatgacaa gccgggattc attgccttta aagcataacc gt                        522
```

<210> SEQ ID NO 28
<211> LENGTH: 699
<212> TYPE: DNA
<213> ORGANISM: Artificial
<220> FEATURE:
<223> OTHER INFORMATION: Synthetic Sequence

<400> SEQUENCE: 28

```
ttactccaag gctgttgcaa tgttgcgatc tcccacaaga tgacaccaaa gctgtaaaca      60
tctgacttct cattggatgg ctcatcacga agaacttctg gagccatcca ctcaggagtc     120
ccagcagctg acttggatga gagaaatgta ttggccttca gacgtgaaag cccaaaatca     180
caaaccttca ctgtatattt cttgtcaaca agaaggtttg gagatttcag atctctatga     240
acaatggggg gattgcgttt atgaagataa ttcatccccct tagccacatc ataagccata     300
ctaagcctac gtctctcatc caatatctct ttggcgccag atctatgcaa cagcctatac     360
aagctacccc ttgataaata ttccgtgaca attgataagt atggcttatg atgtggctaa     420
```

```
ggggatgaat tatcttcata aacgcaatcc ccccattgtt catagagatc tgaaatctcc    480
aaaccttctt gttgacaaga aatatacagt gaaggtttgt gattttgggc tttcacgtct    540
gaaggccaat acatttctct catccaagtc agctgctggg actcctgagt ggatggctcc    600
agaagttctt cgtgatgagc catccaatga aagtcagat gtttacagct ttggtgtcat    660
cttgtgggag atcgcaacat tgcaacagcc ttggagtaa                          699
```

<210> SEQ ID NO 29
<211> LENGTH: 729
<212> TYPE: DNA
<213> ORGANISM: Artificial
<220> FEATURE:
<223> OTHER INFORMATION: Synthetic Sequence

<400> SEQUENCE: 29

```
acacccatga gcaattgcct tgagacctac attagtcacc ccacgatctg aattgcatcc     60
acgaattgta agcttcccca accctcctcg agaggctgtc ccaacggcaa tggcagcaag    120
tctaacatct gttgccttct ttccctccaa gcttcgggat aggtatcctt cgtcactaat    180
ttcctggttt tcatttccag tacttccgta gctgtggatt tcagtcttgc aaatactgct    240
cagaagcata agccagcgct tggatacaga agcacagaca ctcctatctt ggcctgcagg    300
cagccttcta aggatctcaa agaggcattc atctggcaaa gattcaatag atgtctttgg    360
cttctgcttc tgctcaaacc attctccgct gatatcaaat ggaacactga gcgatcctt    420 agaaggctgc ctgcaggcca agataggagt gtctgtgctt ctgtatccaa gcgctggctt    480
atgcttctga gcagtatttg caagactgaa atccacagct acggaagtac tggaaatgaa    540
aaccaggaaa ttagtgacga aggatacct tcccgaagct tggagggaaa gaaggcaaca    600
gatgttagac ttgctgccat tgccgttggg acagcctctc gaggagggtt ggggaagctt    660
acaattcgtg gatgcaattc agatcgtggg gtgactaatg taggtctcaa ggcaattgct    720
catgggtgt                                                           729
```

<210> SEQ ID NO 30
<211> LENGTH: 729
<212> TYPE: DNA
<213> ORGANISM: Artificial
<220> FEATURE:
<223> OTHER INFORMATION: Synthetic Sequence

<400> SEQUENCE: 30

```
agccttgaga ccatgactag tcaccccacg aaccatgttg cttccacgga ttgagagctt     60
ccccaatcct cctcgagatg aagtcccaac agctatggca gccagtctaa catctgttgc    120
cttctttcct tccaagcttc gagagaggta tcccttacct ccaaattcta catcatcacc    180
ctccttttca gggttctcta ctgtggtatt tttgttaaca gagatttcac ttttgcaaat    240
actgcttaga agcataagcc agcgcttgga aacacaggca catgcactcc tgtcttcgcc    300
agcaggcaac cttctaaaga tctcaaagag acactcatct ggcaaggctt caatagaggt    360
tttctgcttt tgctcgaacc attctccatc aaaaacgaat ggagcattga cacgagaagg    420
ttgcctgctg gcgaagacag gagtgcatgt gcctgtgttt ccaagcgctg gcttatgctt    480
ctaagcagta tttgcaaaag tgaaatctct gttaacaaaa ataccacagt agagaaccct    540
gaaaaggagg gtgatgatgt agaatttgga ggtaagggat acctctctcg aagcttggaa    600
ggaaagaagg caacagatgt tagactggct gccatagctg ttgggacttc atctcgagga    660
```

```
ggattgggga agctctcaat ccgtggaagc aacatggttc gtgggggtgac tagtcatggt    720 ctcaaggct                                                             729
```

<210> SEQ ID NO 31
<211> LENGTH: 759
<212> TYPE: DNA
<213> ORGANISM: Artificial
<220> FEATURE:
<223> OTHER INFORMATION: Synthetic Sequence

<400> SEQUENCE: 31

```
aagagggcaa tccttgattg agatggactg cagcttgggg catagccttg cagtagcttg     60
caagccttca tttccaatat ttgggcatga ttcaatagtt aaggtggtca agttggggca    120
accttcagct attgcaatca aaccctttgtt gctgattgag gaacaatgac acaagtcaag   180
cttctccaac atatgacatc cttttgctac ctgagacaga ccctcatccc caatggtaga    240
tacattccat aaagaaagtg atctgagaga agggcaacca tgagcaactg cagagaggcc    300
aaggtttgtg acaccacgct cagagttgct tcctctgatt gaaagcttcc ctagaccgcc    360
acggctacta gtcccaactg caattgcagc aagcctcaca tcagtggctt tcttctttca    420
atcagaggaa gcaactctga gcgtggtgtc acaaaccttg gcctctctgc agttgctcat    480
ggttgccctt ctctcagatc actttcttta tggaatgtat ctaccattgg ggatgagggt    540
ctgtctcagg tagcaaaagg atgtcatatg ttggagaagc ttgacttgtg tcattgttcc    600
tcaatcagca acaagggttt gattgcaata gctgaaggtt gccccaactt gaccaccta    660 actattgaat catgcccaaa tattggaaat gaaggcttgc aagctactgc aaggctatgc    720
cccaagctgc agtccatctc aatcaaggat tgccctctt                           759
```

<210> SEQ ID NO 32
<211> LENGTH: 355
<212> TYPE: DNA
<213> ORGANISM: Artificial
<220> FEATURE:
<223> OTHER INFORMATION: Synthetic Sequence

<400> SEQUENCE: 32

```
tctcaaactc gtttgtgctg agagaaccaa gggtttcttc ccttgcagag aagaaaattt     60
ggatacatat ggttaagttt atttagatat cttgtttgtt cttcatctt tctcagatat     120 ggtttggaaa tgggagattg gggatgaatg atgctacctt ggtggcaaga aaaagctta     180 aaggttggat tttgaggcta tccctttatg tgatcttgcc accaagctag catcattcaa    240
ccttatctct ctctcttgag atcttctccc atggagggggt gatggcttat gtatataggt   300
ttcccagctg tagcatcttt agggtttgag attcctaacc atctttactt cctgt         355
```

<210> SEQ ID NO 33
<211> LENGTH: 355
<212> TYPE: DNA
<213> ORGANISM: Artificial
<220> FEATURE:
<223> OTHER INFORMATION: Synthetic Sequence

<400> SEQUENCE: 33

```
tctcaaactc gtttgtgctg agagaaccaa gggtttcttc ccttgcagag aagaaaattt     60
ggatacatat ggttaagttt atttagatat cttgtttgtt cttcatctt tctcagatat     120 ggtttggaaa tgggagattg gggatgattc tccaatcctt cttgttgaga aaaagctta     180 aaggttggat tttgaggcta tccctttatg tgatctcaac aagaaggttt ggagaatcaa    240
```

-continued

```
ccttatctct ctctcttgag atcttctccc atggaggggt gatggcttat gtatataggt    300
ttcccagctg tagcatcttt agggtttgag attcctaacc atctttactt cctgt         355
```